US012616678B2

(12) United States Patent
Robertson et al.

(10) Patent No.: US 12,616,678 B2
(45) Date of Patent: May 5, 2026

(54) METHODS TO OF ALDEHYDE DEHYDROGENASES FOR TREATMENT OF CANCER

(71) Applicant: THE PENN STATE RESEARCH FOUNDATION, University Park, PA (US)

(72) Inventors: Gavin P. Robertson, Hummelstown, PA (US); Venkata Saketh Sriram Dinavahi, Hershey, PA (US); Raghavendra Gowda Chandagalu Doreswamy, Plainsboro, PA (US); Todd Schell, Palmyra, PA (US); Kishore Punnath, Hershey, PA (US)

(73) Assignee: The Penn State Research Foundation, University Park (PA)

( * ) Notice: Subject to any disclaimer, the term of this patent is extended or adjusted under 35 U.S.C. 154(b) by 520 days.

(21) Appl. No.: 18/007,889

(22) PCT Filed: Jun. 10, 2021

(86) PCT No.: PCT/US2021/036793

§ 371 (c)(1),
(2) Date: Dec. 2, 2022

(87) PCT Pub. No.: WO2021/252749

PCT Pub. Date: Dec. 16, 2021

(65) Prior Publication Data

US 2023/0301965 A1 Sep. 28, 2023

Related U.S. Application Data

(60) Provisional application No. 63/037,328, filed on Jun. 10, 2020.

(51) Int. Cl.
*A61K 31/404* (2006.01)
*A61K 47/69* (2017.01)
*A61P 35/00* (2006.01)

(52) U.S. Cl.
CPC ........ *A61K 31/404* (2013.01); *A61K 47/6911* (2017.08); *A61P 35/00* (2018.01)

(58) Field of Classification Search
CPC .... A61K 31/404; A61K 47/6911; A61P 35/00
See application file for complete search history.

(56) References Cited

U.S. PATENT DOCUMENTS 4,897,355 A 1/1990 Eppstein et al.
5,208,036 A 5/1993 Eppstein et al.
(Continued)

FOREIGN PATENT DOCUMENTS

WO 2020219531 A1 10/2020

OTHER PUBLICATIONS

Ding et al. (Arch Pharm Chem Life Sci 2020; 353) (Year: 2020).*
(Continued)

*Primary Examiner* — Brandon J Fetterolf
(74) *Attorney, Agent, or Firm* — Meunier Carlin & Curfman LLC

(57) ABSTRACT

Disclosed are compositions and methods for inhibiting aldehyde dehydrogenases. In further aspects, treatment of cancers by inhibiting aldehyde dehydrogenases with the disclosed compositions are also disclosed.

30 Claims, 37 Drawing Sheets

(56) References Cited

U.S. PATENT DOCUMENTS

| | | | |
|---|---|---|---|
| 5,264,618 | A | 11/1993 | Felgner et al. |
| 5,279,833 | A | 1/1994 | Rose |
| 5,283,185 | A | 2/1994 | Epand et al. |
| 5,334,761 | A | 8/1994 | Gebeyehu et al. |
| 5,459,127 | A | 10/1995 | Felgner et al. |
| 5,648,097 | A | 7/1997 | Nuwayser |
| 5,736,392 | A | 4/1998 | Hawley-Nelson et al. |
| 5,753,613 | A | 5/1998 | Ansell et al. |
| 5,785,992 | A | 7/1998 | Ansell et al. |
| 6,376,248 | B1 | 4/2002 | Hawley-Nelson et al. |
| 6,534,535 | B1 | 3/2003 | Zhu et al. |
| 6,586,410 | B1 | 7/2003 | Wheeler et al. |
| 6,630,486 | B1 | 10/2003 | Royer |
| 6,733,777 | B2 | 5/2004 | Erbacher et al. |
| 7,145,039 | B2 | 12/2006 | Chu et al. |
| 2018/0162943 | A1 | 6/2018 | Antonia |
| 2022/0175723 | A1* | 6/2022 | Dinavahi et al. |

OTHER PUBLICATIONS

Luke and Hodi (Clin. Cancer Res; 18(1) Jan. 1, 2012) (Year: 2012).*

Webb et al. (J. Biomed Res, 2018, 32 (5)) (Year: 2018).*

Dinavahi et al. (European Journal of Medicinal Chemistry 187 (2020) 111962) (Year: 2019).*

Dinavahi et al., Design, synthesis characterization and biological evaluation of novel multi-isoform ALDH inhibitors as potential anticancer agents', European Journal of Medicinal Chemistry, Dec. 12, 2019, vol. 187, pp. 1-12.

Pubmed Compound Record for CID 3995650, '1-[2-[(5-Amino-1,3,4-thiadiazol-2-yl)sulfanyl]acetyl]indole-2,3-dione', U. S. National Library of Medicine, Sep. 12, 2005, pp. 1-6 (https://pubchem.ncbi.nlm.nih,gov/compound/3995650).

International Search Report and Written Opinion issued in International Application No. PCT/US2021/036793 mailed Nov. 3, 2021, 11 pages.

Berge, S. M. et al., Pharmaceutical Salts, J. Pharm. Sci., 66:1-19, 1977.

A. R. Gennaro, Remington: The Science and Practice of Pharmacy, Lippincott Williams & Wilkins, 21st ed., 2005, pp. 766-767.

Remington: The Science and Practice of Pharmacy, 21st Ed., Lippincott Williams & Wilkins, 2006, p. 880-882 and p. 886-888.

Parajuli, B., et al., Development of Selective Inhibitors for Human Aldehyde Dehydrogenase 3A1 (ALDH3A1) for the Enhancement of Cyclophosphamide Cytotoxicity, Chembiochem, 2014; 15(5):701-12.

Kimble-Hill, A.C., et al., Development of Selective Inhibitors for Aldehyde Dehydrogenases Based on Substituted Indole-2,3-diones, J Med Chem, 2014;57(3):714-22.

Parajuli, B., et al., Selective ALDH3A1 Inhibition by Benzimidazole Analogues Increase Mafosfamide Sensitivity in Cancer Cells, J Med Chem, 2014;57(2):449-61.

Pulla, VK, et al., Targeting NAMPT for Therapeutic Intervention in Cancer and Inflammation: Structure-Based Drug Design and Biological Screening. Chem Biol Drug Des 2015;86(4):881-94.

Pulla, VK, et al., Energy-Based Pharmacophore and Three-Dimensional Quantitative Structure—Activity Relationship (3D-QSAR) Modeling Combined with Virtual Screening to Identify Novel Small-Molecule Inhibitors of Silent Mating-Type Information Regulation 2 Homologue 1 (SIRT1). J Chem Inf Model 2016; 56(1):173-87.

Pulla, VK, et al., Structure-based drug design of small molecule SIRT1 modulators to treat cancer and metabolic disorders. J Mol Graph Model 2014; 52:46-56.

Luo Y, et al., ALDHIA isozymes are markers of human melanoma stem cells and potential therapeutic targets. Stem Cells 2012; 30(10):2100-13.

Yue, L, et al., Targeting ALDH1 to decrease tumorigenicity, growth and metastasis of human melanoma. Melanoma Res 2015; 25(2):138-48.

Durinikova E, et al., ALDH1A3 upregulation and spontaneous metastasis formation is associated with acquired chemoresistance in colorectal cancer cells. BMC Cancer 2018; 18(1):848.

Marcato P, et al., Aldehyde dehydrogenase: its role as a cancer stem cell marker comes down to the specific isoform. Cell Cycle 2011; 10(9):1378-84.

Matsui W, et al., Clonogenic multiple myeloma progenitors, stem cell properties, and drug resistance. Cancer research 2008; 68(1):190-7.

Deng S, et al., Distinct expression levels and patterns of stem cell marker, aldehyde dehydrogenase isoform 1 (ALDH1), in human epithelial cancers. PloS one 2010; 5(4):e10277.

Ginestier C, et al., ALDH1 is a marker of normal and malignant human mammary stem cells and a predictor of poor clinical outcome. Cell stem cell 2007; 1(5):555-67.

Yang Y, et al., NEK2 mediates ALDHIA1-dependent drug resistance in multiple myeloma. Oncotarget 2014;5(23):11986-97.

Rodriguez-Zavala JS, et al., Role of Aldehyde Dehydrogenases in Physiopathological Processes. Chem Res Toxicol 2019, 32, 405-420.

Grune T. Protein Oxidation Products as Biomarkers. Free Radic Biol Med 2014; 75 Suppl 1:S7.

Shoeb M, et al., 4-Hydroxynonenal in the pathogenesis and progression of human diseases. Curr Med Chem 2014; 21(2):230-7).

Rao PC, et al., Coptisine-induced cell cycle arrest at G2/M phase and reactive oxygen species-dependent mitochondria-mediated apoptosis in non-small-cell lung cancer A549 cells. Tumour Biol 2017; 39(3):1010428317694565.

Yagi K. Simple assay for the level of total lipid peroxides in serum or plasma. Methods Mol Biol 1998; 108:101-6.

Krishnegowda G, et al., Synthesis and biological evaluation of a novel class of isatin analogs as dual inhibitors of tubulin polymerization and Akt pathway. Bioorg Med Chem 2011; 19(20):6006-14.

Rao PC, et al., Cytotoxicity of withasteroids: withametelin induces cell cycle arrest at G2/M phase and mitochondria-mediated apoptosis in non-small cell lung cancer A549 cells. Tumour Biol 2016; 37(9):12579-87.

Dinavahi SS, et al., Combined inhibition of PDE4 and PI3Kdelta modulates the inflammatory component involved in the progression of chronic obstructive pulmonary disease. Drug Res (Stuttg) 2014; 64(4):214-9.

* cited by examiner

1
Isatin

2

3

4
KS100

Reagents and conditions: a) $Br_2$/EtOH; b) $K_2CO_3$, DMF, rt, $BrCH_2C_6H_4CH_2Br$, 8h; c) Thiourea, EtOH, 100°C, 4h.

| Compound | # | $R_1$ | $R_2$ | X | Docking scores ALDH1A1 | ALDH2 | ALDH3A1 |
|---|---|---|---|---|---|---|---|
| KS104 | 3a | H | H | S | −10.71 | −8.51 | −13.383 |
| KS108 | 3b | Br | H | S | −11.637 | −10.28 | −13.369 |
| KS110 | 3c | H | Br | S | −9.727 | −7.308 | −13.358 |
| KS112 | 3d | Cl | H | S | −11.938 | −11.024 | −13.666 |
| KS114 | 3e | H | Cl | S | −11.271 | −7.061 | −14.237 |
| KS116 | 3f | F | H | S | −11.056 | −11.03 | −12.157 |
| KS118 | 3g | H | F | S | −11.197 | −11.205 | −14.24 |
| KS106 | 3h | CF3 | H | S | −11.721 | −10.374 | −12.229 |
| KS122 | 3i | H | CF3 | S | −10.836 | −9.497 | −14.564 |
| KS100 | 3j | Br | Br | S | −10.247 | −8.716 | −13.851 |
| KS102 | 3k | Cl | Cl | S | −10.841 | −8.169 | −14.103 |
| KS120 | 3l | F | Br | S | −10.432 | −7.294 | −13.039 |
| KS105 | 4a | H | H | Se | −11.487 | −10.592 | −12.375 |
| KS109 | 4b | Br | H | Se | −10.149 | −6.82 | −14.441 |
| KS111 | 4c | H | Br | Se | −10.144 | −6.804 | −14.507 |
| KS113 | 4d | Cl | H | Se | −10.14 | −6.756 | −13.268 |
| KS115 | 4e | H | Cl | Se | −10.841 | −6.978 | −13.85 |
| KS117 | 4f | F | H | Se | −10.144 | −7.929 | −12.119 |
| KS119 | 4g | H | F | Se | −8.387 | −8.609 | −13.943 |
| KS107 | 4h | CF3 | H | Se | −9.988 | −11.146 | −14.229 |
| KS123 | 4i | H | CF3 | Se | −11.741 | −9.494 | −13.46 |
| KS101 | 4j | Br | Br | Se | −10.149 | −8.975 | −12.638 |
| KS103 | 4k | Cl | Cl | Se | −10.594 | −10.841 | −13.701 |
| KS121 | 4l | F | Br | Se | −7.495 | −9.792 | −12.567 |

| Compound | Enzyme inhibition - $IC_{50}$ (nM) | | |
|---|---|---|---|
| | ALDH1A1 | ALDH2 | ALDH3A1 |
| 3a | 4633 | >10000 | 4205 |
| 3b | 8524 | >10000 | 4878 |
| 3c | 1713 | >10000 | 6323 |
| 3d | >10000 | >10000 | 3067 |
| 3e | 177 | >10000 | 3586 |
| 3f | 5224 | >10000 | 2855 |
| 3g | 598 | >10000 | 241 |
| 3h | 334 | 2137 | 360 |
| 3i | 268 | 1783 | 246 |
| 3j | 230 | 1542 | 193 |
| 3k | 279 | 1642 | 219 |
| 3l | 285 | 1782 | 219 |
| 4a | >10000 | >10000 | 4007 |
| 4b | 333 | 939 | 344 |
| 4c | 360 | >10000 | >10000 |
| 4d | >10000 | >10000 | 2767 |
| 4e | >10000 | >10000 | >10000 |
| 4f | 5192 | >10000 | 2364 |
| 4g | 1054 | >10000 | 246 |
| 4h | 6492 | >10000 | 1520 |
| 4i | 657 | 3491 | 251 |
| 4j | 397 | 2012 | 333 |
| 4k | 384 | 1809 | 327 |
| 4l | 420 | 1917 | 368 |

Fig. 10

| Compound | $IC_{50}$ (μM)[a]/72 h | | | | | | | | | |
|---|---|---|---|---|---|---|---|---|---|---|
| | UACC 903[b] | 1205 Lu[b] | HCT116[c] | HT29[c] | NCIH929[d] | U266[d] | RPMI8226[d] | MM.1R[d] | MM.1S[d] | HF2441[e] |
| 3h | 5.7 ± 2.0 | 5.7 ± 1.5 | 5.7 ± 0.1 | 4.9 ± 1.1 | 1.5 ± 0.3 | 2.6 ± 0.6 | 1.6 ± 0.4 | 1.7 ± 0.4 | 2.2 ± 0.3 | 20.7 ± 1.3 |
| 3i | 3.7 ± 0.6 | 3.7 ± 0.8 | 4.5 ± 0.2 | 5.8 ± 0.1 | 1.5 ± 0.4 | 4.7 ± 1.2 | 4.4 ± 1.9 | 4.7 ± 0.2 | 4.9 ± 1.0 | 13.9 ± 0.1 |
| 3j | 3.7 ± 0.2 | 2.1 ± 0.6 | 2.9 ± 0.1 | 2.5 ± 0.2 | 0.3 ± 0.1 | 1.0 ± 0.3 | 1.2 ± 0.28 | 1.3 ± 0.6 | 2.1 ± 0.6 | 9.8 ± 0.5 |
| 3k | 3 ± 0.6 | 2.4 ± 0.3 | 3.2 ± 0.7 | 2.6 ± 0.3 | 0.7 ± 0.2 | 2.7 ± 0.6 | 1.3 ± 0.17 | 1.6 ± 0.3 | 1.6 ± 0.3 | 5.4 ± 0.2 |
| 3l | 3.9 ± 1.1 | 5.6 ± 1.5 | 5.8 ± 0.1 | 4.4 ± 0.7 | 1.6 ± 0.4 | 2.8 ± 0.4 | 1.5 ± 0.29 | 3.6 ± 0.4 | 3.1 ± 0.8 | 10 ± 0.9 |
| 3a | >100 | >100 | ND | ND | ND | ND | ND | ND | ND | >100 |
| Cpd 3 | >100 | >100 | ND | ND | ND | ND | ND | ND | ND | >100 |

[a] $IC_{50}$ = Compound concentration required to inhibit cell proliferation by 50%. Data are expressed as the mean ± SD from the dose-response curve of at least three independent experiments. ND-not determined.

[b] Melanoma.

[c] Colon cancer.

[d] Multiple myeloma.

[e] Normal human fibroblasts.

Fig. 11

| Compound | Day 1 | Day 7 | Day 14 | % of weight loss compared to control (at day 14) | P-value compared to DMSO |
|---|---|---|---|---|---|
| DMSO | 22.9 | 24.2 | 24.4 | - | - |
| 3h | 22.5 | 20.6 | 23.8 | 2% | 0.6006 |
| 3i | 23.1 | 20.7 | 20.9 | 11% | <0.0001 |
| 3j | 22.7 | 18.7 | 19.4 | 12% | <0.0001 |
| 3k | 22.4 | 19.6 | 20.3 | 10% | <0.0001 |
| 3l | 22.6 | 20.9 | 20.2 | 15% | <0.0001 |

A, B: Dose-response for ALDH1A1

C,D: Dose-response for ALDH2

E,F: Dose-response for ALDH3A1

METHODS TO OF ALDEHYDE DEHYDROGENASES FOR TREATMENT OF CANCER

CROSS REFERENCE TO RELATED APPLICATIONS

This application is a national stage application filed under 35 U.S.C. § 371 of PCT/US2021/036793, filed Jun. 10, 2021, which claims the benefit of priority to U.S. Provisional Application 63/037,328, filed Jun. 10, 2020, the contents of which are incorporated by reference herein in their entirety.

BACKGROUND

A major mechanism by which cancer cells develop resistance is through upregulation of the aldehyde dehydrogenases (ALDHs).

The 19 human ALDH isozymes are broadly defined as a superfamily of NAD(P)+-dependent enzymes and participate in aldehyde metabolism, catalyzing the oxidation of exogenous aldehydes (drugs and ethanol) and endogenous aldehydes (lipids, amino acids, or vitamins) into their corresponding carboxylic acids. The ALDHs confer a survival advantage to metabolically active cancer cells, by oxidizing aldehydes that accumulate and cause oxidative damage, into less toxic, more soluble carboxylic acids. Accordingly, ALDH overexpression is linked to poor overall and shorter recurrence-free survival in gastric, breast, lung, pancreatic and prostate carcinomas, head and neck squamous cell carcinomas (HNSCCs), and melanomas, among others.

There is a continuing need for ALDH inhibitors to inhibit tumors and treat cancer in a subject in need thereof. The subject matters disclosed herein addresses these and other needs.

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to compositions and methods for inhibiting aldehyde dehydrogenases. In further aspects, the disclosed subject matter relates to the treatment of cancers by inhibiting aldehyde dehydrogenases. In a further aspect, the disclosed subject matter relates to combinations of aldehyde dehydrogenase inhibitors and checkpoint inhibitors, such as PD-1 and PD-L1.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

FIG. 10. ALDH inhibitory activity of 3(a-l) and 4(a-l). Compounds 3(a-l) and 4(a-l) were evaluated for ALDH1A1, 2 and 3A1 inhibitory activity at 500 nM, 5 uM and 500 nM respectively. % inhibition was calculated for each compound and compared to DMSO control.

FIG. 11. Anti-proliferative effect of 3(h-l). Compounds 3(h-l) were evaluated for their anti-proliferative effects on melanoma, colon cancer, multiple myeloma and normal human fibroblasts (FF2441). Cells were treated with 3(h-l) at various concentrations for 72 hours, and $IC_{50}$s were calculated.

DETAILED DESCRIPTION

Figure 1A:
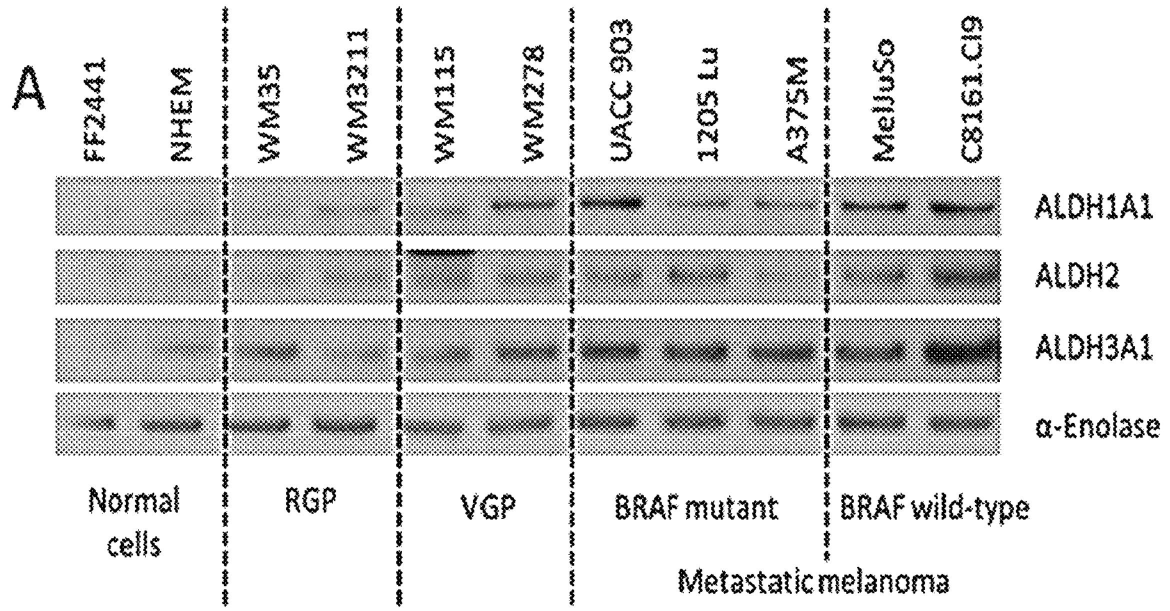
FIGS. 1A-1F. illustrate that the ALDH family is collectively important in melanoma. Western blot showing ALDH1A1, 2 and 3A1 expression levels in normal human fibroblasts (FF2441), melanocytes (NHEM), radial growth phase (RGP), vertical growth phase (VGP) and metastatic melanoma cell lines. ALDH expression in general increased during disease progression and was not dependent on BRAF mutational status. Alpha-enolase served as the loading control (FIG. 1A). Data from the TCGA database showing slightly better survival with ALDH1A1 and 2 overexpression (FIG. 1B) and worse survival with ALDH3A1 overexpression (FIG. 1C) in melanoma patients. The data are available through the UCSC Xena Cancer Browser. Individual siRNA knockdown of ALDH1A1, 2 and 3A1 did not significantly reduce the growth of UACC 903 cells after 72 hours in an MTS assay. siRNA to BRAF and ALDH18A1 served as positive controls. Scrambled siRNA served as the negative control (FIG. 1D). siRNA knockdown of ALDH1A1, 2, 3A1, 18A1 and BRAF in UACC 903 cells was confirmed via western blot. Alpha-enolase served as loading control (FIG. 1E). Pharmacological inhibition of ALDH1A1, 2 and 3A1 using ALDH isoform-specific inhibitors (Cpd 3, CVT10216 and CB7, respectively) and the multi-ALDH isoform inhibitor, DEAB, revealed multi-ALDH isoform inhibition was most effective in inhibiting UACC 903 cell growth (FIG. 1F).

The materials, compounds, compositions, and methods described herein may be understood more readily by reference to the following detailed description of specific aspects of the disclosed subject matter, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the compound" includes mixtures of two or more such compounds, and the like.

"Optional" or "optionally" means that the subsequently described event or circumstance can or cannot occur, and that the description includes instances where the event or circumstance occurs and instances where it does not.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The term "patient" or "subject" preferably refers to a human in need of treatment for any purpose, and more preferably a human in need of a treatment to treat cancer. However, the term "patient" can also refer to non-human animals, preferably mammals such as dogs, cats, horses, cows, pigs, sheep, goats, poultry, rodents, and non-human primates, among others, that are in need of treatment with a compound as disclosed herein.

A "pharmaceutically acceptable" component is one that is suitable for use with humans and/or animals without undue adverse side effects (such as toxicity, irritation, and allergic response) commensurate with a reasonable benefit/risk ratio.

A "pharmaceutically acceptable excipient" is an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "pharmaceutically acceptable salt" refers to salts which are suitable for use in a subject without undue toxicity or irritation to the subject and which are effective for their intended use. Pharmaceutically acceptable salts include pharmaceutically acceptable acid addition salts and base addition salts. Pharmaceutically acceptable salts are well-known in the art, such as those detailed in S. M. Berge et al., J. Pharm. Sci., 66:1-19, 1977. Exemplary pharmaceutically acceptable salts are those suitable for use in a subject without undue toxicity or irritation to the subject and which are effective for their intended use which are formed with inorganic acids such as hydrochloric acid, hydrobromic acid, hydroiodic acid, nitric acid, phosphoric acid, sulfuric acid and sulfamic acid; organic acids such as acetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, formic acid, fumaric acid, glutamic acid, glycolic acid, glycerophosphoric acid, hemisulfic acid, heptanoic acid, hexanoic acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, trichloroacetic acid, trifluoroacetic acid and undecanoic acid; inorganic bases such as ammonia, hydroxide, carbonate, and bicarbonate of ammonium; organic bases such as primary, secondary, tertiary and quaternary amine compounds ammonium, arginine, betaine, choline, caffeine, diolamine, diethylamine, diethanolamine, 2-dimethylaminoethanol, 2-diethylaminoethanol, dicyclohexylamine, dicyclohexylamine, dibenzylamine, N, N-dibenzylphenethylamine, 1-ephenamine, N, N'-dibenzylethylenediamine, ethanolamine, ethylamine, ethylenediamine, glucosamine, histidine, hydrabamine, isopropylamine, 1h-imidazole, lysine, methylamine, N-ethylpiperidine, N-methylpiperidine, N-methylmorpholine, N, N-dimethylaniline, piperazine, trolamine, methylglucamine, purines, piperidine, pyridine, theobromine, tetramethylammonium compounds, tetraethylammonium compounds, trimethylamine, triethylamine, tripropylamine and tributylamine and metal cations such as aluminum, calcium, copper, iron, lithium, magnesium, manganese, potassium, sodium, and zinc.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to infection, an effective amount comprises an amount sufficient to cause a cancer cell to shrink and/or to decrease the growth rate of the cancer cells or to prevent or delay tumor progression or metastasis. In some embodiments, an effective amount is an amount sufficient to delay development of cancer. In some embodiments, an effective amount is an amount sufficient to prevent or delay occurrence and/or recurrence of cancer. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell growth or infiltration; and/or (iv) relieve to some extent one or more of the symptoms associated with cancer.

Other scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; Engelke, D. R., RNA Interference (RNAi): Nuts and Bolts of RNAi Technology, DNA Press LLC, Eagleville, PA, 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808; Chu, E. and Devita, V. T., Eds., Physicians' Cancer Chemotherapy Drug Manual, Jones & Bartlett Publishers, 2005; J. M. Kirkwood et al., Eds., Current Cancer Therapeutics, 4th Ed., Current Medicine Group, 2001; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, PA: Lippincott, Williams & Wilkins, 2004; and L. Brunton et al., Goodman & Gilman's The Pharmacological Basis of Therapeutics, McGraw-Hill Professional, 12th Ed., 2011.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C{=}C(Z^3Z^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can have from 5 to 10 carbon atoms. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms, and up to 12 carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a shorthand notation for C=O, which is also referred to herein as a "carbonyl."

The terms "amine" or "amino" as used herein are represented by the formula $—NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is $—C(O)NZ^1Z^2$.

The term "carboxylic acid" as used herein is represented by the formula —C(O)OH. A "carboxylate" or "carboxyl" group as used herein is represented by the formula $—C(O)O^-$.

The term "ester" as used herein is represented by the formula $—OC(O)Z^1$ or $—C(O)OZ^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula $—NO_2$.

The term "silyl" as used herein is represented by the formula $—SiZ^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula $—S(O)_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula $—S(O)_2NH—$.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compositions

Disclosed herein are ALCH inhibitors of Formula I.

I

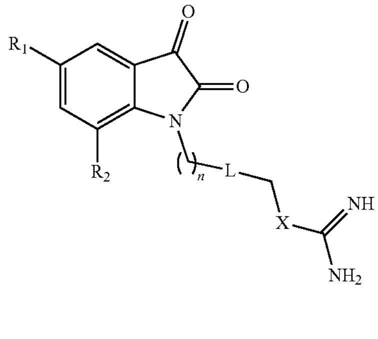

wherein,

X is S or Se;

L is a $C_1$-$C_8$ alkyl, $C_2$-$C_8$ alkenyl, $C_2$-$C_8$ alkynyl, $C_5$-$C_6$ cycloalkyl, $C_5$-$C_6$ heterocycloalkyl, phenyl, or heteroaryl any of which is optionally substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$;

n is 0, 1, 2, or 3;

$R_1$ and $R_2$ are each independently chosen from H, F, Cl, Br, I, $NO_2$, OH, $C_1$-$C_6$ alkyl, $C_1$-$C_6$ alkoxyl, and $C_1$-$C_6$ haloalkyl, or a pharmaceutically acceptable salt thereof.

In some examples, disclosed are compounds of Formula I where X is S. In other examples, disclosed are compounds of Formula I where X is Se.

In some examples, disclosed are compounds of Formula I where L is a $C_1$-$C_8$ alkyl that is unsubstituted or substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$.

In some examples, disclosed are compounds of Formula I where L is a $C_2$-$C_8$ alkenyl that is unsubstituted or substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$.

In some examples, disclosed are compounds of Formula I where L is a $C_2$-$C_8$ alkynyl that is unsubstituted or substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$.

In some examples, disclosed are compounds of Formula I where L is a $C_5$-$C_6$ cycloalkyl that is unsubstituted or substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$.

In some examples, disclosed are compounds of Formula I where L is a $C_5$-$C_6$ heterocycloalkyl that is unsubstituted or substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$. For example, L can be a tetrahydrofuranyl, tetrahydropyranyl, pyrrolidinyl, pyrazolinyl, imidazolidinyl, piperadinyl, piperazinyl, or morpholino.

In some examples, disclosed are compounds of Formula I where L is a phenyl that is unsubstituted or substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$. In specific examples, when n is 1, and L is a phenyl, compounds of Formula I can be shown by Formula II.

II

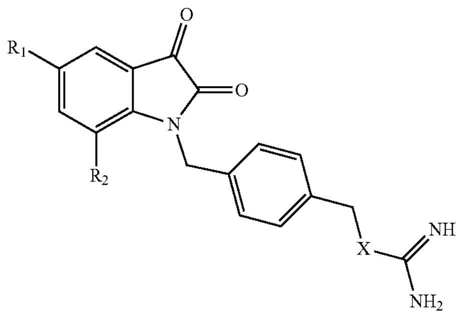

In some examples, disclosed are compounds of Formula I where L is a heteroaryl that is unsubstituted or substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$. Examples of heteroaryl can be pyridinyl, pyrimidinyl, pyrrolyl, and imidazolyl. In further examples, when n is 1 and L is a six membered heteroaryl group, compounds of Formula I can be shown by Formula III

III

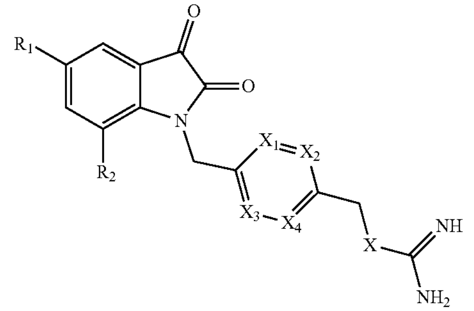

wherein $X_1$, $X_2$, $X_3$, and $X_4$ are independently chosen from CH or N, with at least one of $X_1$, $X_2$, $X_3$, and $X_4$ being N.

In some examples, disclosed are compounds of Formula I where n is 0. In other examples, n is 1. In still other examples, n is 2. Still further examples include when n is 3.

In some examples, $R_1$ is H, F, Cl, Br, I, $NO_2$, OH, $C_1$-$C_6$ alkyl, $C_1$-$C_6$ alkoxyl, and $C_1$-$C_6$ haloalkyl. In some examples, $R_2$ is H, F, Cl, Br, I, $NO_2$, OH, $C_1$-$C_6$ alkyl, $C_1$-$C_6$ alkoxyl, and $C_1$-$C_6$ haloalkyl. In some examples, at least one of $R_1$ and $R_2$ is a halogen. In some examples, both $R_1$ and $R_2$ are halogens. In some examples, at least one of $R_1$ and $R_2$ is H. In other examples, both $R_1$ and $R_2$ are H. In further examples, at least one of $R_1$ and $R_2$ is $CF_3$.

In some specific examples, disclosed are the hydrogen bromide salts of compounds of Formula I.

In a specific example, disclosed herein is a compound of Formula I called KS100, which has the structure:

(1)

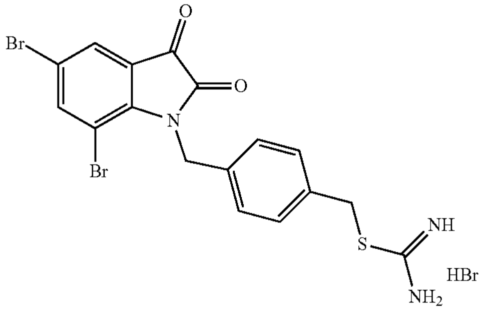

KS100

In further examples, disclosed herein are the following compounds: KS104 (3a): 2-[4-(2,3-Dioxo-2,3-dihydroindol-1-ylmethyl)benzyl]isothiourea hydrobromide; KS104FB: 2-[4-(2,3-Dioxo-2,3-dihydroindol-1-ylmethyl)benzyl]isothiourea; KS108 (3b):2-[4-(5-Bromo-2,3-dioxo-2,3-dihydroindol-1-ylmethyl)benzyl]isothiourea hydrobromide; KS100 FB: 2-[4-(5-Bromo-2,3-dioxo-2,3-dihydroindol-1-ylmethyl)benzyl]isothiourea; KS110 (3c): 2-[4-(7-Bromo-2,3-dioxo-2,3-dihydroindol-1-ylmethyl)benzyl]isothiourea hydrobromide; KS110 FB: 2-[4-(7-Bromo-2,3-dioxo-2,3-dihydroindol-1-ylmethyl)benzyl]isothiourea; KS112 (3d): 2-[4-(5-Chloro-2,3-dioxo-2,3-dihydroindol-1-ylmethyl)benzyl]isothiourea hydrobromide; KS112 FB: 2-[4-(5-Chloro-2,3-dioxo-2,3-dihydroindol-1-ylmethyl)benzyl]isothiourea; KS114 (3e): 2-[4-(7-Chloro-2,3-dioxo-2,3-dihydroindol-1-ylmethyl)benzyl]isothiourea hydrobromide; KS114 FB: 2-[4-(7-Chloro-2,3-dioxo-2,3-dihydroindol-1-ylmethyl)benzyl]isothiourea; KS116 (3f): 2-[4-(5-Fluoro-2,3-dioxo-2,3-dihydroindol-1-ylmethyl)benzyl]isothiourea hydrobromide; KS116 FB: 2-[4-(5-Fluoro-2,3-dioxo-2,3-dihydroindol-1-ylmethyl)benzyl]isothiourea; KS118 (3g): 2-[4-(7-Fluoro-2,3-dioxo-2,3-dihydroindol-1-ylmethyl)benzyl]isothiourea hydrobromide; KS118 FB: 2-[4-(7-Fluoro-2,3-dioxo-2,3-dihydroindol-1-ylmethyl)benzyl]isothiourea; KS106 (3h): 2-[4-(2,3-Dioxo-5-trifluoromethyl-2,3-dihydroindol-1-ylmethyl)benzyl]isothiourea hydrobromide; KS106 FB: 2-[4-(2,3-Dioxo-5-trifluoromethyl-2,3-dihydroindol-1-ylmethyl)benzyl]isothiourea; KS122 (3i): 2-[4-(2,3-Dioxo-7-trifluoromethyl-2,3-dihydroindol-1-ylmethyl)benzyl]isothiourea hydrobromide; KS122 FB: 2-[4-(2,3-Dioxo-7-trifluoromethyl-2,3-dihydroindol-1-ylmethyl)benzyl]isothiourea; KS100 (3j): 2-[4-(5, 7-Dibromo-2, 3-dioxo-2, 3-dihydroindol-1-ylmethyl)benzyl]isothiourea hydrobromide; KS100 FB: 2-[4-(5, 7-Dibromo-2, 3-dioxo-2, 3-dihydroindol-1-ylmethyl)benzyl]isothiourea; KS102 (3k): 2-[4-(5,7-Dichloro-2,3-dioxo-2,3-dihydroindol-1-ylmethyl)benzyl]isothiourea hydrobromide; KS102 FB: 2-[4-(5,7-Dichloro-2,3-dioxo-2,3-dihydroindol-1-ylmethyl)benzyl]isothiourea; KS120 (3l): 2-[4-(7-Bromo-5-fluoro-(2,3-dioxo-2,3-dihydroindol-1-ylmethyl)benzyl]isothiourea hydrobromide; KS120 FB: 2-[4-(7-Bromo-5-fluoro-2,3-dioxo-2,3-dihydroindol-1-ylmethyl)benzyl]isothiourea; KS105 (4a): 2-[4-(2,3-Dioxo-2,3-dihydroindol-1-ylmethyl)benzyl]isoselenourea hydrobromide; KS105 FB: 2-[4-(2,3-Dioxo-2,3-dihydroindol-1-ylmethyl)benzyl]isoselenourea; KS109 (4b): 2-[4-(5-Bromo-2,3-dioxo-2,3-dihydroindol-1-ylmethyl)benzyl]isoselenourea hydrobromide; KS109 FB: 2-[4-(5-Bromo-2,3-dioxo-2,3-dihydroindol-1-ylmethyl)benzyl]isoselenourea; KS111 (4c): 2-[4-(7-Bromo-2,3-dioxo-2,3-dihydroindol-1-ylmethyl)benzyl]isoselenourea hydrobromide; KS111 FB: 2-[4-(7-Bromo-2,3-dioxo-2,3-dihydroindol-1-ylmethyl)benzyl]isoselenourea; KS113 (4d): 2-[4-(5-Chloro-2,3-dioxo-2,3-dihydroindol-1-ylmethyl)benzyl]isoselenourea hydrobromide; KS113 FB: 2-[4-(5-Chloro-2,3-dioxo-2,3-dihydroindol-1-ylmethyl)benzyl]isoselenourea; KS115 (4e): 2-[4-(7-Chloro-2,3-dioxo-2,3-dihydroindol-1-ylmethyl)benzyl]isoselenourea hydrobromide; KS115 FB: 2-[4-(7-Chloro-2,3-dioxo-2,3-dihydroindol-1-ylmethyl)benzyl]isoselenourea; KS117 (4f): 2-[4-(5-Fluoro-2,3-dioxo-2,3-dihydroindol-1-ylmethyl)benzyl]isoselenourea hydrobromide; KS117 FB: 2-[4-(5-Fluoro-2,3-dioxo-2,3-dihydroindol-1-ylmethyl)benzyl]isoselenourea; KS119 (4g): 2-[4-(7-Fluoro-2,3-dioxo-2,3-dihydroindol-1-ylmethyl)benzyl]isoselenourea hydrobromide; KS119 FB: 2-[4-(7-Fluoro-2,3-dioxo-2,3-dihydroindol-1-ylmethyl)benzyl]isoselenourea; KS107 (4h): 2-[4-(2,3-Dioxo-5-trifluoromethyl-2,3-dihydroindol-1-ylmethyl)benzyl]isoselenourea hydrobromide; KS107 FB: 2-[4-(2,3-Dioxo-5-trifluoromethyl-2,3-dihydroindol-1-ylmethyl)benzyl]isoselenourea; KS123 (4i): 2-[4-(2,3-Dioxo-7-trifluoromethyl-2,3-dihydroindol-1-ylmethyl)benzyl]isoselenourea hydrobromide; KS123 FB: 2-[4-(2,3-Dioxo-7-trifluoromethyl-2,3-dihydroindol-1-ylmethyl)benzyl]isoselenourea; KS101 (4j): 2-[4-(5, 7-Dibromo-2, 3-dioxo-2, 3-dihydroindol-1-ylmethyl)benzyl]isoselenourea hydrobromide; KS101 FB: 2-[4-(5, 7-Dibromo-2, 3-dioxo-2, 3-dihydroindol-1-ylmethyl)benzyl]isoselenourea; KS103 (4k): 2-[4-(5, 7-Dichloro-2, 3-dioxo-2, 3-dihydroindol-1-ylmethyl)benzyl]isoselenourea hydrobromide; KS103 FB: 2-[4-(5, 7-Dichloro-2, 3-dioxo-2, 3-dihydroindol-1-ylmethyl)benzyl]isoselenourea; KS121 (4l): 2-[4-(7-Bromo-5-fluoro-2,3-dioxo-2,3-dihydroindol-1-ylmethyl)benzyl]

isoselenourea hydrobromide; and KS121 FB: 2-[4-(7-Bromo-5-fluoro-2,3-dioxo-2,3-dihydroindol-1-ylmethyl) benzyl]isoselenourea.

Pharmaceutically acceptable salts, hydrates, amides and esters of Formula I, II, and III can be included in compositions according to aspects of the present invention. In some examples, salts formed by an inorganic acid or organic acid selected from the group consisting of: hydrochloric acid, hydrobromic acid, hydroiodic acid, nitric acid, phosphoric acid, sulfuric acid and sulfamic acid; acetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, formic acid, fumaric acid, glutamic acid, glycolic acid, glycerophosphoric acid, hemisulfic acid, heptanoic acid, hexanoic acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, trichloroacetic acid, trifluoroacetic acid and undecanoic acid.

Also, in some further aspects are disclosed compounds of Formula IV

IV

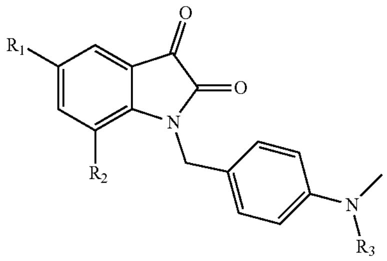

wherein $R_3$ is —$CH_3$, —$COCH_3$, or —$COCHCH_2$ or a pharmaceutically acceptable salt, hydrate, amide or ester thereof.

Compositions according to the present invention encompass stereoisomers of chemical structures shown and/or described herein. Compositions according to the present invention encompass the individual enantiomers of the compounds having chemical structures shown and/or described herein, as well as wholly or partially racemic mixtures of any of these.

Compositions including Formula I (e.g., KS100) and a pharmaceutically acceptable carrier are provided according to aspects of the present invention. Compositions including Formula II-IV and a pharmaceutically acceptable carrier are provided according to aspects of the present invention.

Compositions including Formula I (e.g., KS100), II, III, and/or IV and a pharmaceutically acceptable carrier optionally include a lipid-based pharmaceutically acceptable carrier. The term "lipid-based carrier" refers to macromolecular structures having lipid and/or lipid derivatives as the major constituent.

Lipids included in lipid-based carriers can be naturally-occurring lipids, synthetic lipids or combinations thereof.

A lipid-based carrier is formulated as a liposome for use in compositions, kits and methods according to aspects of the invention. Compositions including Formula I (e.g., KS100), II, III, and/or IV and a pharmaceutically acceptable carrier are provided according to aspects of the present invention wherein the pharmaceutically acceptable carrier includes liposomes.

The term "liposome" refers to a bilayer particle of amphipathic lipid molecules enclosing an aqueous interior space. The compositions disclosed herein, including those of Formula I-IV, can be in the bilayer portion of the liposome. Liposomes are typically produced as small unilammellar vesicles (SUVs), large unilammellar vesicles (LUVs) or multilammellar vesicles (MLVs). An anti-cancer composition of the present invention is associated with liposomes by encapsulation in the aqueous interior space of the liposomes, disposed in the lipid bilayer of the liposomes and/or associated with the liposomes by binding, such as ionic binding or association by van der Waals forces. Thus, anti-cancer composition of the present invention is contained in liposomes when it is encapsulated in the aqueous interior space of the liposomes, disposed in the lipid bilayer of the liposomes and/or associated with the liposomes by binding, such as ionic binding or association by van der Waals forces. Liposomes according to aspects of the invention are generally in the range of about 1 nanometer-1 micron in diameter although they are not limited with regard to size.

Liposomal formulations of anti-cancer compositions according to aspects of the present invention include can include one or more types of neutral, cationic lipid and/or anionic lipid, such that the liposomal formulations have a net neutral surface charge at physiological pH. According to aspects, a PEG-modified lipid is included.

The term cationic lipid refers to any lipid which has a net positive charge at physiological pH. Examples of cationic lipids include, but are not limited to, N-(1-(2,3-dioleyloxy) propyl)-N,N,N-trimethylammonium chloride (DOTMA); 1,2-dioleoyloxy-3-(trimethylammonium)propane (DOTAP); 1,2-dioleoyl-3-dimethylammonium-propane (DODAP); dioctadecylamidoglycylspermine (DOGS); 1,2-dipalmitoylphosphatidylethanolamidospermine (DPPES); 2,3-dioleyloxy-N-(2-(sperminecarboxamido)ethyl)-N,N-dimethyl-1-propanaminium trifluoroacetate (DOSPA); dimyristoyltrimethylammonium propane (DMTAP); (3-dimyristyloxypropyl)(dimethyl)(hydroxyethyl)ammonium (DMRIE); dioctadecyldimethylammonium chloride (DODAC), Dimethyldidodecylammonium bromide (DDAB); 3β[N-(N',N'-dimethylaminoethane)-carbamoyl] cholesterol (DC-Chol); 1-[2-(9(Z)-octadecenoyloxy)-ethyl]-2-(8(Z)-heptadecenyl)-3-(2-hydroxyethyl)-imidazolinium (DOTIM); bis-guanidinium-spermidine-cholesterol (BGTC); bis-guanidinium-tren-cholesterol (BGTC); 1,3-Dioleoyloxy-2-(6-carboxy-spermyl)-propylamid (DOSPER) N-[3-[2-(1,3-dioleoyloxy)propoxy-carbonyl]propyl]-N,N,N-trimethylammonium iodide (YKS-220); as well as pharmaceutically acceptable salts and mixtures thereof. Additional examples of cationic lipids are described in Lasic and Papahadjopoulos, Medical Applications of Liposomes, Elsevier, 1998; U.S. Pat. Nos. 4,897,355; 5,208,036; 5,264,618; 5,279,833; 5,283,185; 5,334,761; 5,459,127; 5,736,392; 5,753,613; 5,785,992; 6,376,248; 6,586,410; 6,733,777; and 7,145,039.

The term neutral lipid refers to any lipid which has no net charge, either uncharged or in neutral charge zwitterionic form, at physiological pH. Examples of neutral lipids include, but are not limited to, L-alpha-phosphatidylcholine (ePC), distearoylphosphatidylcholine (DSPC), dioleoylphosphatidylethanolamine (DOPE), distearoylphosphatidylethanolamine (DSPE); 1,2-dioleoyl-sn-glycero-3-

Phosphocholine (DOPC), 1,2-dipalmitoyl-sn-glycero-3-phosphoethanolamine (DPPE), cephalin, ceramide, cerebrosides, cholesterol, diacylglycerols, and sphingomyelin.

The term anionic lipid refers to any lipid which has a net negative charge at physiological pH. Examples of anionic lipids include, but are not limited to, dihexadecylphosphate (DhP), phosphatidyl inositols, phosphatidyl serines, such as dimyristoyl phosphatidyl serine, and dipalmitoyl phosphatidyl serine, phosphatidyl glycerols, such as dimyristoylphosphatidyl glycerol, dioleoylphosphatidyl glycerol, dilauryloylphosphatidyl glycerol, dipalmitoylphosphatidyl glycerol, distearyloylphosphatidyl glycerol, phosphatidic acids, such as dimyristoyl phosphatic acid and dipalmitoyl phosphatic acid and diphosphatidyl glycerol.

The term "modified lipid" refers to lipids modified to aid in, for example, inhibiting aggregation and/or precipitation, inhibiting immune response and/or improving half-life in circulation in vivo. Modified lipids include, but are not limited to, pegylated lipids, such as polyethyleneglycol 2000 distearoylphosphatidylethanolamine (PEG(2000) DSPE); 1,2-dipalmitoyl-sn-glycero-3-phosphoethanolamine-N-[methoxy(polyethylene glycol)-2000](DPPE-PEG-2000), and polyethyleneglycol 750 octadecylsphingosine (PEG (750) C8). Exemplary ratios of components included in liposomal formulations of the present invention are neutral lipid:polyethyleneglycol modified neutral lipid—80:20 mol %.

For example, liposomal formulations include L-alpha-phosphatidylcholine and 1,2-dipalmitoyl-sn-glycero-3-phosphoethanolamine-N-[methoxy(polyethylene glycol)-2000] in an 80:20 mol % ratio according to aspects of the present invention.

Thus, according to aspects, liposomal formulations of anti-cancer compositions include at least one polyethylene glycol modified neutral lipid, wherein the total amount of polyethylene glycol modified neutral lipid is an amount in the range of 10-30 molar percent, inclusive, such as 15-25 molar percent polyethylene glycol modified neutral lipid and further including anionic, cationic or neutral lipids, with the proviso that the resulting liposomes have a net neutral surface charge at physiological pH.

In addition to containing one or more anti-cancer compositions of the present invention, liposomes of the present invention optionally contain any of a variety of useful biologically active molecules and substances including, but not limited to, adjunct therapeutics, proteins, peptides, carbohydrates, oligosaccharides, drugs, and nucleic acids capable of being complexed with the liposomes. The term "biologically active molecules and substances" refers molecules or substances that exert a biological effect in vitro and/or in vivo, such as, but not limited to, nucleic acids, inhibitory RNA, siRNA, shRNA, ribozymes, antisense nucleic acids, antibodies, hormones, small molecules, aptamers, decoy molecules and toxins.

Liposomes are generated using well-known standard methods, including, but not limited to, solvent/hydration methods, ethanol or ether injection methods, freeze/thaw methods, sonication methods, reverse-phase evaporation methods, and surfactant methods. Liposomes and methods relating to their preparation and use are found in Liposomes: A Practical Approach (The Practical Approach Series, 264), V. P. Torchilin and V. Weissig (Eds.), Oxford University Press; 2nd ed., 2003; N. Duzgunes, Liposomes, Part A, Volume 367 (Methods in Enzymology) Academic Press; 1st ed., 2003; L. V. Allen, Jr. et al., Ansel's Pharmaceutical Dosage Forms and Drug Delivery Systems, 8th Ed., Philadelphia, PA: Lippincott, Williams & Wilkins, 2005, pp. 663-666; and A. R. Gennaro, Remington: The Science and Practice of Pharmacy, Lippincott Williams & Wilkins, 21st ed., 2005, pp. 766-767.

A composition according to the invention generally includes about 0.1-99%, or a greater amount, of KS100 or other compound of formula I. Combinations of KS100 or other compounds of Formula I and one or more additional therapeutic agents in a pharmaceutical composition are also considered within the scope of the present invention.

Liposomal formulations of anti-cancer compositions of the present invention are injected intravenously and/or applied topically according to aspects of the present invention.

Methods of treating a subject are provided according to aspects of the present invention which include administering a therapeutically effective amount of a composition including KS100 to a subject in need thereof, wherein the subject has an abnormal proliferative condition, such as cancer, pre-neoplastic hyperproliferation, cancer in-situ, neoplasms, metastasis, tumor or benign growth. Methods of treating a subject are provided according to aspects of the present invention which include administering a therapeutically effective amount of a composition comprising a compound of Formula I-IV to a subject in need thereof, wherein the subject has an abnormal proliferative condition, such as cancer, pre-neoplastic hyperproliferation, cancer in-situ, neoplasms, metastasis, tumor or benign growth.

Subjects are identified as having, or at risk of having, cancer using well-known medical and diagnostic techniques.

Particular cancers treated using methods and compositions described herein are characterized by abnormal cell proliferation including, but not limited to, pre-neoplastic hyperproliferation, cancer in-situ, neoplasms and metastasis. Compositions including KS100 according to aspects of the present invention have utility in treatment of a subject having cancer or at risk of having cancer characterized by overexpression of one or more aldehyde dehydrogenases, such as in melanoma and other cancers including, but not limited to, cancers of the liver, prostate, breast, brain, stomach, pancreas, blood cells, uterus, cervix, ovary, lung, colon, connective tissues (sarcomas) and other soft tissues, including neck squamous cell carcinomas (HNSCCs). Particular cancers treated using methods and compositions described herein are characterized by overexpression of one or more aldehyde dehydrogenases selected from ALDH1A1, ALDH2, ALDH3A1, or a combination of any two or more thereof. Particular cancers treated using methods and compositions described herein are melanoma or other cancers including, but not limited to, cancers of the liver, prostate, breast, brain, stomach, pancreas, blood cells, uterus, cervix, ovary, lung, colon, connective tissues (sarcomas) and other soft tissues, including neck squamous cell carcinomas (HNSCCs), characterized by overexpression of one or more aldehyde dehydrogenases selected from ALDH1A1, ALDH1A2, ALDH1A3, ALDH1L1, ALDH2, ALDH3A1, ALDH5A1, ALDH18A1, or a combination of any two or more thereof.

A cancer may be determined to overexpress one or more aldehyde dehydrogenases by assay of cells or tissue obtained from the subject, such as by biopsy or analysis of cancer cells present in blood or other body fluids. Assays such as Western blot, rtPCR, immunoassay, and the like, can be used.

Methods and compositions of the present invention can be used for prophylaxis as well as amelioration of signs and/or symptoms of cancer. The terms "treating" and "treatment"

used to refer to treatment of a cancer in a subject include: preventing, inhibiting or ameliorating the cancer in the subject, such as slowing progression of the cancer and/or reducing or ameliorating a sign or symptom of the cancer.

A therapeutically effective amount of a composition including KS100 of the present invention is an amount which has a beneficial effect in a subject being treated. In subjects having cancer or at risk for having cancer, such as a condition characterized by abnormal cell proliferation including, but not limited to, pre-neoplastic hyperproliferation, cancer in-situ, neoplasms, metastasis, a tumor, a benign growth or other condition responsive to an inventive composition, a therapeutically effective amount of a composition including KS100 is effective to ameliorate or prevent one or more signs and/or symptoms of the condition. For example, a therapeutically effective amount of a composition is effective to detectably increase apoptosis and/or decrease proliferation of cells of a cancer condition characterized by abnormal cell proliferation including, but not limited to, pre-neoplastic hyperproliferation, cancer in-situ, neoplasms, metastasis, a tumor, a benign growth or other condition responsive to an inventive composition.

Methods of treatment of a subject having, or at risk of having, cancer, are provided according to aspects of the present invention including administration of a pharmaceutically effective amount of liposomes containing KS100.

Combination Compositions and Methods

Combinations of a composition including KS100 and an additional therapeutic agent are administered according to aspects of the present invention. In some aspects, a composition including KS100 and two or more additional therapeutic agents are administered to a subject to treat cancer in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present invention include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

Combination therapies utilizing KS100 compositions of the present invention and one or more additional therapeutic agents may show synergistic effects, e.g., a greater therapeutic effect than would be observed using either the KS100 composition of the present invention or one or more additional therapeutic agents alone as a monotherapy. In particular, the disclosed compositions including KS100 or those of Formula I can be combined with a checkpoint inhibitor or a BRAF inhibitor, such as, for example, sorafenib, vemurafenib, dabrafenib, and/or encorafenib.

According to aspects, combination therapies include: (1) a pharmaceutical composition including KS100 in combination with one or more additional therapeutic agents; and (2) co-administration of a composition including KS100 of the present invention with one or more additional therapeutic agents wherein the KS100 and the one or more additional therapeutic agents have not been formulated in the same composition. When using separate formulations, the composition including KS100 of the present invention may be administered at the same time, intermittent times, staggered times, prior to, subsequent to, or combinations thereof, with reference to the administration of the one or more additional therapeutic agents.

Combination treatments can allow for reduced effective dosage and increased therapeutic index of the composition including KS100 of the present invention (or Formula II-IV) and the one or more additional therapeutic agents used in methods of the present invention.

Optionally, a method of treating a subject having cancer or at risk of having cancer further includes an adjunct anti-cancer treatment. An adjunct anti-cancer treatment can be administration of an anti-cancer agent.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflomithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

An anti-cancer agent administered according to aspects of the present invention can be an anti-cancer immune therapeutic agent. Thus, methods according to aspects of the present disclosure include administration of: an anti-cancer immune therapeutic agent, and KS100, for treatment of cancer in a subject.

The term "anti-cancer immune therapeutic agent" as used herein refers to agents which activate or suppress a component of the immune system of a subject for treatment of cancer in the subject. An anti-cancer immune therapeutic agent can be a cell-based agent, such as natural killer cells (NK cells), cytotoxic T lymphocytes, lymphocytes, macrophages, dendritic cells, and the like. An "anti-cancer immune therapeutic agent" which is a cell-based agent can include modified cells, such as genetically-modified, chemically-modified, or biochemically-modified, immune cells. Alternatively, "an anti-cancer immune therapeutic agent" can be a small molecule, protein (such as, but not limited to, an antibody), peptide, saccharide, nucleic acid, or other non-cell based agent.

NK Cell-Based Anti-Cancer Immune Therapeutic Agents

Natural killer (NK) cells are a critical component of the innate immune response against malignant cells. They were identified by their ability to kill tumor cells without prior sensitization to tumor antigens. This is distinct from the mechanism by which T-cells lyse tumor cells, which requires recognition of tumor antigens presented in the context of major histocompatibility class I or II by a specific T-cell receptor. Due to the delay in priming and expansion of T-cells bearing a particular tumor antigen specific receptor, NK cells act as a first line of defense against newly transformed cells. Thus, Natural killer (NK) cells are immunotherapeutic agents in particular in the fight against cancers.

Non-limiting examples of NK cell-based anti-cancer immune therapeutic agents include autologous NK cells, ex-vivo stimulated mbIL-21 allogeneic NK, ex vivo expanded allogeneic NK cells, and NK-92 (Neukoplast).

CAR-T Cell-Based Anti-Cancer Immune Therapeutic Agents

Chimeric antigen receptor T cells (also known as CAR T cells) are T cells that have been genetically engineered to produce an artificial T-cell receptor. Chimeric antigen receptors (CARs, also known as chimeric immunoreceptors, chimeric T cell receptors or artificial T cell receptors) are receptor proteins that have been engineered to give T cells the new ability to target a specific protein. The receptors are chimeric because they combine both antigen-binding and T-cell activating functions into a single receptor. CAR-T cell therapy uses T cells engineered with CARs for cancer therapy. The premise of CAR-T immunotherapy is to modify T cells to recognize cancer cells in order to more effectively target and destroy them.

Non-Cell Based Anti-Cancer Immune Therapeutic Agents

Particular non-cell based anti-cancer immune therapeutic agents include, but are not limited to, indoleamine 2,3-dioxygenase 1 (IDO1) inhibitors, lymphocyte-activation gene 3 (LAG3) antibodies, T-cell immunoglobulin and mucin domain-3 (TIM3) antibodies, OX-40 agonists, Glucocorticoid-induced TNFR-related (GITR), BRAF inhibitors, and immune checkpoint inhibitors.

IDO1 inhibitors include, but are not limited to, indoximod, navoximod, epacadostat, INCB024360, BMS-986205.

LAG3 antibodies include, but are not limited to, BMS-986016, LAG525, MK-4280, GSK2831781, IMP321.

TIM3 antibodies include, but are not limited to, MBG453, TSR-022, LY3321367.

OX-40 agonists include, but are not limited to, OX86, Fc-OX40L, MOXR0916 and GSK3174998.

GITR include, but are not limited to, TRX518, MK-4166, MK-1248, AMG 228, BMS-986156, INCAGN01876, MEDI1873, GWN323.

BRAF inhibitors include (such as, for example, sorafenib, vemurafenib, dabrafenib, and encorafenib, and combinations thereof.

Immune checkpoint inhibitors include, but are not limited to, PD-1 inhibitors, PD-L1 inhibitors, and CTLA4 inhibitors. Specific examples of checkpoint inhibitors include nivolumab, pembrolizumab, cemiplimab, ipilimumab, atezolizumab, avelumab, durvalumab, and combinations thereof.

An adjunct anti-cancer treatment can be a radiation treatment of a subject or an affected area of a subject's body.

Pharmaceutical compositions suitable for delivery to a subject may be prepared in various forms illustratively including physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local injection, and particularly intravenous injection.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, one or more anti-cancer compounds described herein is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to KS100 or other compounds of Formula I-IV, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

In particular aspects, compositions of the present invention are formulated for topical application. In further particular aspects, compositions of the present invention are formulated for topical application and are characterized by less than 10% absorption of an active ingredient in the composition into the system of an individual treated topically. In still further particular aspects, compositions of the present invention are formulated for topical application and are characterized by less than 9%, 8%, 7%, 6%, 5%, 4%, 3%, 2%, 1% absorption of an active ingredient in the composition into the system of an individual treated topically. Absorption into the system of an individual can be measured by any of various methods, particularly assay for the active ingredient, a metabolite and/or a breakdown product of the active ingredient in a sample obtained from an individual treated with the topical formulation. For example, a blood, plasma or serum sample can be assayed for presence of the active ingredient, a metabolite of the active ingredient and/or a breakdown product of the active ingredient.

A topical formulation can be an ointment, lotion, cream or gel in particular aspects. Topical dosage forms such as ointment, lotion, cream or gel bases are described in Remington: The Science and Practice of Pharmacy, $21^{st}$ Ed., Lippincott Williams & Wilkins, 2006, p.880-882 and p.886-888; and in Allen, L. V. et al., Ansel's Pharmaceutical Dosage Forms and Drug Delivery Systems, $8^{th}$ Ed., Lippincott Williams & Wilkins, 2005, p.277-297.

Pharmaceutically acceptable carriers and formulation of pharmaceutical compositions are known in the art, illustratively including, but not limited to, as described in Remington: The Science and Practice of Pharmacy, $21^{st}$ Ed., Lippincott, Williams & Wilkins, Philadelphia, PA, 2006; and Allen, L. V. et al., Ansel's Pharmaceutical Dosage Forms and Drug Delivery Systems, $8^{th}$ Ed., Lippincott, Williams & Wilkins, Philadelphia, PA, 2005.

A pharmaceutical composition according to the present invention is suitable for administration to a subject by a variety of systemic and/or local routes including, but not limited to, intravenous, intramuscular, subcutaneous, intraperitoneal, oral, otic, rectal, vaginal, topical, parenteral, pulmonary, ocular, nasal, intratumoral and mucosal.

An inventive composition may be administered acutely or chronically. For example, a composition as described herein may be administered as a unitary dose or in multiple doses over a relatively limited period of time, such as seconds-hours. In a further embodiment, administration may include multiple doses administered over a period of days-years, such as for chronic treatment of cancer.

A therapeutically effective amount of a pharmaceutical composition according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg to 100 mg/kg body weight, optionally in the range of about 0.01 mg/kg to 10 mg/kg, and further optionally in the range of about 0.1 mg/kg to 5 mg/kg. According to particular aspects, a therapeutically effective amount of a liposomal formulation of KS100 is in the range of about 5 mg/kg to 60 mg/kg. Further, dosage may be adjusted depending on whether treatment is to be acute or continuing.

Advantageously, anti-cancer compounds according to aspects of the present invention are formulated to achieve lipid-solubility and/or aqueous-solubility.

In particular aspects, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular aspects, a particulate carrier is formulated such that particles have an average particle size in the range of about 1 nm-100 nm.

Commercial packages are provided according to aspects of the present invention for treating cancer in a subject in need thereof, including KS100, a KS100 derivative such a compound of Formula I-IV; or a salt, stereoisomer, hydrate, amide or ester of either thereof. One or more auxiliary components are optionally included in commercial packages of the present invention, such as a pharmaceutically acceptable carrier exemplified by a buffer, diluent or a reconstituting agent.

A commercial package including a liposomal formulation of KS100, and/or a KS100 derivative; or a salt, stereoisomer, hydrate, amide or ester of either thereof. A commercial package including a liposomal formulation of a compound of Formula I-IV; or a salt, stereoisomer, hydrate, amide or ester of either thereof.

Aspects of inventive compositions and methods are illustrated in the examples shown and described herein. These examples are provided for illustrative purposes and are not considered limitations on the scope of inventive compositions and methods.

Embodiments of inventive compositions and methods are illustrated in the following examples. These examples are provided for illustrative purposes and are not considered limitations on the scope of inventive compositions and methods.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Statistical analysis was undertaken using the one-way/two-way ANOVA GraphPad PRISM Version 7.04 software. Dunnett's as post hoc analysis was performed when there was a significant difference. Results were considered significant at a p-value of <0.05.

Study 1

Materials and Methods

Cell Lines, Culture Conditions and Chemicals

Normal human fibroblasts (FF2441) were used in examples detailed herein. The human melanoma cell lines WM35, WM115, WM278, WM3211, 1205 Lu, UACC 903, and A375M and normal melanocytes (NHEM) were used in examples detailed herein. The wildtype BRAF melanoma cell line C8161.Cl9 was used in examples detailed herein and MelJuSo was used in examples detailed herein. Cell lines were maintained in a 37° C. humidified 5% $CO_2$ atmosphere incubator and periodically monitored for phenotypic and genotypic characteristics and tumorigenic potential to validate and confirm cell line identity.

The ALDH1A1 and 3A1 specific inhibitors, Cpd 3 and CB7, respectively, were synthesized as detailed in Parajuli, B., et al., *Chembiochem,* 2014; 15(5):701-12; Kimble-Hill, A. C., et al., *J Med Chem,* 2014; 57(3):714-22; and Parajuli, B., et al., *J Med Chem,* 2014; 57(2):449-61. The ALDH1A1 specific inhibitor, CM037, and ALDH2 specific inhibitor, CVT10216, were purchased from Tocris. Isatin and the multi-ALDH isoform inhibitor DEAB was purchased from Sigma (St. Louis, USA).

Structure Preparation

The structures of ALDH1A1, 2 and 3A1 bound to the inhibitors CM037, psoralen, and CB7, respectively (4λ4L, 5L13 and 4L20), were retrieved from the protein data bank (PDB). The 3D structures of the protein complexes were prepared using a protein preparation wizard tool (Schrodinger, LLC, Portland, OR, USA); water molecules were deleted except those in the inhibitor binding pocket, bond orders were assigned, hydrogen atoms were added and metal ions were treated as described in detail in Pulla V K, et al., Structure-based drug design of small molecule SIRT1 modulators to treat cancer and metabolic disorders. *J Mol Graph Model* 2014; 52:46-56; Pulla V K, et al., Targeting NAMPT for Therapeutic Intervention in Cancer and Inflammation: Structure-Based Drug Design and Biological Screening. *Chem Biol Drug Des* 2015; 86(4):881-94; Pulla V K, et al., Energy-Based Pharmacophore and Three-Dimensional Quantitative Structure—Activity Relationship (3D-QSAR) Modeling Combined with Virtual Screening To Identify Novel Small-Molecule Inhibitors of Silent Mating-Type Information Regulation 2 Homologue 1 (SIRT1). *J Chem Inf Model* 2016; 56(1):173-87. Next, the orientation of the side chain structures of Gln and Asn was flipped, if necessary, to provide the maximum degree of H-bond interactions. The charge state of His residues was optimized. Finally, a restrained minimization of the protein structure was performed using the OPLS force field with backbone atoms being fixed. The minimized protein was used for the docking analysis.

Grid Generation and Ligand Preparation

Prepared protein structures were used to generate scoring grids for subsequent docking calculations as described in detail in Pulla V K, et al., Structure-based drug design of small molecule SIRT1 modulators to treat cancer and metabolic disorders. *J Mol Graph Model* 2014; 52:46-56; Pulla V K, et al., Targeting NAMPT for Therapeutic Intervention in Cancer and Inflammation: Structure-Based Drug Design and Biological Screening. *Chem Biol Drug Des* 2015; 86(4):881-94; Pulla V K, et al., Energy-Based Pharmacophore and Three-Dimensional Quantitative Structure—Activity Relationship (3D-QSAR) Modeling Combined with Virtual Screening To Identify Novel Small-Molecule Inhibitors of Silent Mating-Type Information Regulation 2 Homologue 1 (SIRT1). *J Chem Inf Model* 2016; 56(1):173-87. To each protein crystal structure, a grid box of default size (20×20×20 Å) was centered on the corresponding active site position. Default parameters were used and no constraints were included during grid generation. The ligand preparation was then performed using the ligprep module in Schrodinger as described in detail in Pulla V K, et al., Structure-based drug design of small molecule SIRT1 modulators to treat cancer and metabolic disorders. *J Mol Graph Model* 2014; 52:46-56; Pulla V K, et al., Targeting NAMPT for Therapeutic Intervention in Cancer and Inflammation: Structure-Based Drug Design and Biological Screening. *Chem Biol Drug Des* 2015; 86(4):881-94; Pulla V K, et al., Energy-Based Pharmacophore and Three-Dimensional Quantitative Structure—Activity Relationship (3D-QSAR) Modeling Combined with Virtual Screening To Identify Novel Small-Molecule Inhibitors of Silent Mating-Type Information Regulation 2 Homologue 1 (SIRT1). *J Chem Inf Model* 2016; 56(1):173-87.

siRNA Transfections

Duplex stealth siRNA sequences for scrambled and ALDH1A1, 2, 3A1, 18A1 and BRAF were obtained from Invitrogen. Individual siRNAs were introduced into UACC 903 cells via nucleofection using an Amaxa nucleofector with solution R/program K-17. Nucleofection efficiency was >90% with 80-90% cell viability. Following siRNA transfection, UACC 903 cells were plated and allowed to recover for 3 days and then used for MTS assays.

Synthesis of KS100

5,7-dibromoisatin (10 mmol) was dissolved in anhydrous DMF (30 mL) and cooled on ice with stirring. Solid $K_2CO_3$ (11 mmol) was added and the dark-colored suspension was brought to room temperature and stirred for 1 hour. 1,4-bis (bromomethyl)benzene (40 mmol) was added slowly with constant stirring until the starting material had been consumed (monitored by TLC). The reaction mixture was poured into cold water and extracted with ethyl acetate. The ethyl acetate layer was washed with water, brine and dried over $MgSO_4$. The solvent was removed, and the crude product was purified by silica gel column chromatography using (hexanes/ethyl acetate, 80:20) as the eluent to yield the intermediate 5,7-dibromo-1-(4-bromomethylbenzyl)-1H-indole-2,3-dione as orange-red crystals.

To the intermediate compound (1.02 mmol), thiourea (1.02 mmol) and ethanol (25 ml) were added and heated to reflux until the starting material had been consumed (monitored by TLC). The solvent was removed under vacuum. The final product (2-[4-(5,7-dibromo-2,3-dioxo-2,3-dihydro-indol-1-ylmethyl)benzyl]isothiourea) was recrystallized in ethanol-ethyl acetate to afford KS100 (yield 70%). The identity of KS100 was confirmed by nuclear magnetic resonance as well as mass spectra analysis, and purity (>99%) was quantified by high-performance liquid chromatography analysis.

ALDH Isoform-Specific Enzyme Assays

ALDH enzyme assays were performed using a kit as described by the kit manufacturer (R & D Systems, Inc, Minneapolis, MN, USA). Isoform-specific aldehydes were converted to their respective carboxylic acids along with conversion of NAD+ to NADH (absorbance at 340 nm). Specifically, 1 μg/mL of ALDH1A1 was treated with various concentrations of ALDH inhibitor (Isatin, Cpd 3, CM037, CVT10216, CB7, DEAB, KS100) for 15 minutes followed by addition of substrate mixture (10 mM propionaldehyde; 100 mM KCl; 1 mM NAD; 2 mM DTT; 50 mM Tris pH 8.5) and the absorbance of NADH was measured in kinetic mode for 5 minutes at 340 nm wavelength. Similarly, 0.5 μg/mL of ALDH2 was used in the reaction with 2 mM of acetaldehyde as the substrate and 0.2 μg/mL of ALDH3A1 was used in the reaction with 1 mM of 4-nitrobenzaldehyde (4-NBA) as the substrate following addition of ALDH inhibitors.

Cell Viability Assays

Cell viability assays of UACC 903 cells transfected with siRNA, and melanoma cell lines (UACC 903, 1205 Lu, $C_{8161}$.CI9, MelJuSo), FF2441 and NHEM cells treated with ALDH inhibitors were performed. For this, 5,000 cells per well were plated in a 96-well plate and incubated overnight at 37° C. in a 5% $CO_2$ atmosphere. For the siRNA knockdown experiment, cells were incubated for another 72 hours. For the ALDH inhibitor experiments, cells were treated with agents at various concentrations and incubated for 72 hours. 20 μL of MTS reagent was then added into each well and formation of tetrazolium was measured by absorbance after 1 hour at 492 nm. $IC_{50}$ values or % cells for each experimental group were measured in three independent experiments using GraphPad Prism version 7.04 (GraphPad Software, La Jolla, CA).

Toxicity and Maximum Tolerated Dose Studies

To determine the effective dose for in vivo efficacy studies, KS100 and NanoKS100 were injected i.p. and i.v., respectively, into Swiss Webster mice once daily for 7 days. Animals were monitored for changes in body weight, behavior and physical distress compared to control (DMSO for KS100, empty liposome vehicle for NanoKS100). Dose escalation was performed to identify the maximum tolerated dose for KS100 and NanoKS100.

Preparation of NanoKS100

KS100 was encapsulated into a nanoliposome by first combining L-α-Phosphatidylcholine (ePC) and 1,2-Dipalmitoyl-sn-Glycero-3-Phosphoethanolamine-N-[Methoxy (Polyethylene glycol)-2000]ammonium salt (DPPE-PEG-2000) in chloroform at 80:20 mol % for a final lipid concentration of 25 mg/mL (Avanti Polar Lipids). 5 mg of KS100 (in methanol) was then added to 1 mL of nanoliposome solution. The mixture was dried under nitrogen gas and re-suspended in 0.9% saline at 60° C. Following rehydration, the mixture was sonicated at 60° C. for 30 minutes followed by extrusion at 60° C. through a 100-nm polycarbonate membrane using Avanti Mini Extruder (Avanti Polar Lipids Inc-Alabaster, AL). The particle size and charge characteristics were determined using a Malvern Zetasizer (Malvern Instruments, UK).

Characterization of NanoKS100

(a) Drug encapsulation. Efficiency of encapsulation of KS100 in the nanoliposomal formulation was estimated by UV-visible spectrophotometry (SPECTRAmax M2 plate reader; Molecular devices). Specifically, 1 mL of NanoKS100 solution was added to a 10 kDa Centricon filter tube (Millipore) and centrifuged at 3,750 rpm for 30 minutes to remove free KS100. Next, 0.5 mL of purified NanoKS100 was combined with 0.5 mL of a 1:1 solution of chloroform to methanol to destroy the nanoliposomal structure and release the drug into the solution. The precipitated lipids were separated via centrifugation at 10,000 rpm for 15 minutes. The supernatant was then used to measure KS100 concentration, calculated from a standard curve of KS100 from 0.01 to 1 mg/mL. A 1:1 solution of chloroform to methanol was used as the reference blank. The percentage of KS100 incorporated into nanoliposomes was calculated as: (incorporated KS100/total KS100)×100.

(b) Stability. Stability of NanoKS100 stored at 4° C. was assessed weekly by comparing size and zeta potential using the Malvern Zetasizer and measuring $IC_{50}$ efficacy for killing UACC 903 melanoma cells by MTS assay and comparing these values to that of freshly manufactured NanoKS100.

(c) In vitro drug-release kinetics of NanoKS100. Drug release kinetics were measured using 1 mL of purified NanoKS100 by dialysis in 1 L of 10 mM reduced glutathione at room temperature through a molecular weight cut off 25 kDa membrane (Spectra Por). 0.05 mL NanoKS100 in the dialysis bag was removed at 0.5, 1, 2, 4, 8, 12, 24, 36, 48 and 72 hours and the amount of KS100 released at each time point was estimated using UV-visible spectrophotometry.

(d) Hemolytic activity. Fresh mouse and rat blood were drawn and placed into an EDTA test tube for a hemolytic activity assay. Erythrocytes were separated from plasma by centrifugation at 1,500 rpm for 10 minutes at 4° C. using PBS. Erythrocyte pellets were diluted with 50 mL PBS in centrifuge tubes to give a 5% v/v solution, and then treated with 5 μM KS100 in DMSO, NanoKS100 (10-40 μM) in PBS, empty liposome or 1% Triton X-100 (positive control). Samples were incubated at 37° C. for 60 minutes and then centrifuged at 12,000 rpm for 10 minutes. Next, supernatants were transferred to a 96-well plate and absorption measured at 540 nm. The amount of hemoglobin released in the presence of 1% Triton X-100 was set as 100% lysis and % hemolysis was calculated as: (absorbance of the samples at 540 nm/absorbance of the positive control)×100.

ROS Assay

To quantify intracellular ROS levels, the non-fluorescent dye DCFDA was used. DCFDA turns to highly fluorescent 2',7'-dichlorofluorescein upon oxidation by ROS generated in cells. Melanoma (UACC 903 and 1205 Lu) or FF2441 cells were treated with 5 μM of KS100 or other ALDH inhibitors for 24 hours in a 96-well plate. DMSO served as the vehicle control. After 24 hours, 10 μM of DCFDA was added to each well and incubated for 30 minutes prior to measuring fluorescence at 485 nm excitation and 520 nm emission.

Lipid Peroxidation

Lipid peroxidation was measured using the thiobarbituric acid reactive substances (TBARS) kit according to the manufacturer's instructions (Cayman Chemicals). UACC 903 and 1205 Lu cells were treated with 5 μM of KS100 or other ALDH inhibitors for 24 hours. Cell pellets were lysed in PBS by sonication on ice. Lipids in the lysates were hydrolyzed in the presence of acetic acid and sodium hydroxide. Free MDA released from lipids was measured by reaction to TBA colorimetrically at 530 nm. DMSO served as the vehicle control.

Apoptosis Assay

The Annexin-V-PE/7-AAD kit was used to distinguish live cells from apoptototic cells. UACC 903 and 1205 Lu cells were incubated with 5 μM of KS100 or other ALDH inhibitors for 24 hours. DMSO served as the vehicle control. Cells were pelleted after incubation, washed with PBS and stained with Annexin-V-PE and 7-AAD solution per the manufacturer's instructions. Cells were acquired by BD Fortessa flow cytometer and gated for four distinct regions, namely, live cells (Annexin V-$7^-$AAD$^-$), early apoptotic (Annexin V-$7^+$AAD$^-$), late apoptotic (Annexin V-$7^+$ AAD$^+$) and necrotic (Annexin V-$7^-$AAD$^+$) cells.

Western Blot Analysis

Melanoma, FF2441 and NHEM cell lysates were harvested by addition of RIPA lysis buffer and samples were processed for Western Blot analysis. For this, 1 million cells were plated in 100 mm culture dishes and incubated overnight at 37° C. in a 5% $CO_2$ atmosphere. For experiments with KS100, the agent was added after 48 hours of incubation and protein lysates collected following 24 hours of treatment. For the remaining experiments, cells were allowed to grow to 75% confluence followed by collection of protein lysates. Blots were probed with antibodies according to each supplier's recommendations: antibodies to cleaved PARP and LC3B from Cell Signaling Technology; alpha-enolase, ALDH1A1, 2, 3A1, 18A1, BRAF and secondary antibodies conjugated with horseradish peroxidase from Santa Cruz Biotechnology. Immunoblots were developed using the enhanced chemiluminescence detection system (Thermo Fisher Scientific). Alpha-enolase served as the loading control.

Animal Efficacy and Toxicity Studies

Animal efficacy studies were performed in nude mice. For this, 1 million UACC 903 or 1205 Lu cells were injected in both flanks of 4-6 week old female nude balb/c mice. After a week, when the tumors were vascularized, animals were either treated with NanoKS100 (at various doses) or empty liposome vehicle control. Tumor volumes, animal weight and behavior were monitored continuously every other day. Animals were sacrificed after tumor volumes in the vehicle control groups exceeded 2,500 $mm^3$ and tumors were subsequently collected.

Assessment of Serum Biomarkers of Major Organ Toxicity

At the end of the UACC 903 xenograft study for NanoKS100, blood was collected via cardiac puncture from each euthanized animal in a serum separator tube with lithium heparin (BD Microtainer) and analyzed for levels of ALT (alanine aminotransferase), ALKP (alkaline phosphatase), ALB (albumin), GLOB (globulin), TP (total protein), TBIL (total bilirubin), BUN (blood urea nitrogen), GLU (glucose), CREA (creatinine), AMYL (amylase) and CAL (calcium). The empty liposome vehicle group served as the control.

Results

ALDH Overexpression Occurs in Melanoma and is Associated with Disease Progression.

Cancer cell expression of ALDHs often increases with disease progression, as oxidative stress secondary to high metabolic demands leads to ROS generation, lipid peroxidation and the accumulation of toxic aldehydes, which can inhibit cancer cells. Elevated ALDH activity is typically a composite of multiple ALDH isoforms. The major isoforms whose overexpression is implicated in cancer progression and drug resistance include the ALDH1A family and 3A1. ALDH2 has also been extensively characterized and implicated in various disease states, including alcohol-based cancers.

ALDH Overexpression Occurs in Melanoma and is Associated with Disease Progression.

Western blot analysis of ALDH1A1, 2 and 3A1 in melanoma cells revealed that ALDH overexpression occurs in melanoma compared to control fibroblast (FF2441) and melanocyte (NHEM) cells (FIG. 1A). Further, the degree of ALDH expression correlated with melanoma stage such that metastatic melanomas exhibited the highest ALDH expression levels, followed by vertical growth phase and finally radial growth phase melanomas. ALDH expression was not dependent on BRAF mutational status, as ALDH levels were similar between mutant V600EBRAF and wildtype BRAF cells.

Figure 1B:
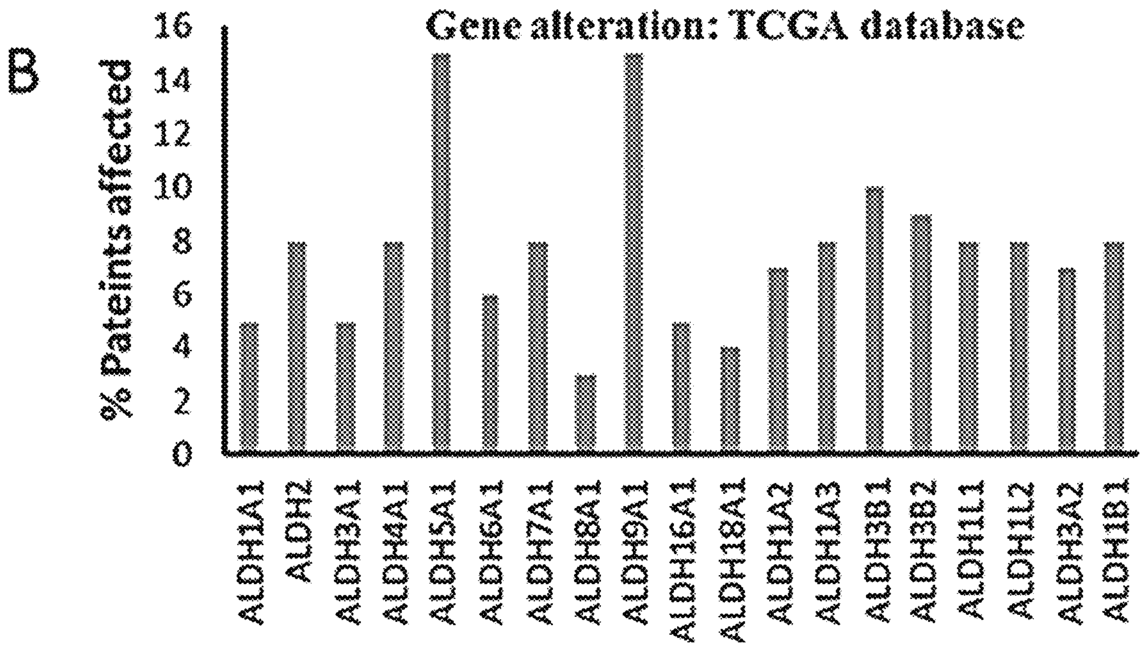
Figure 1C:
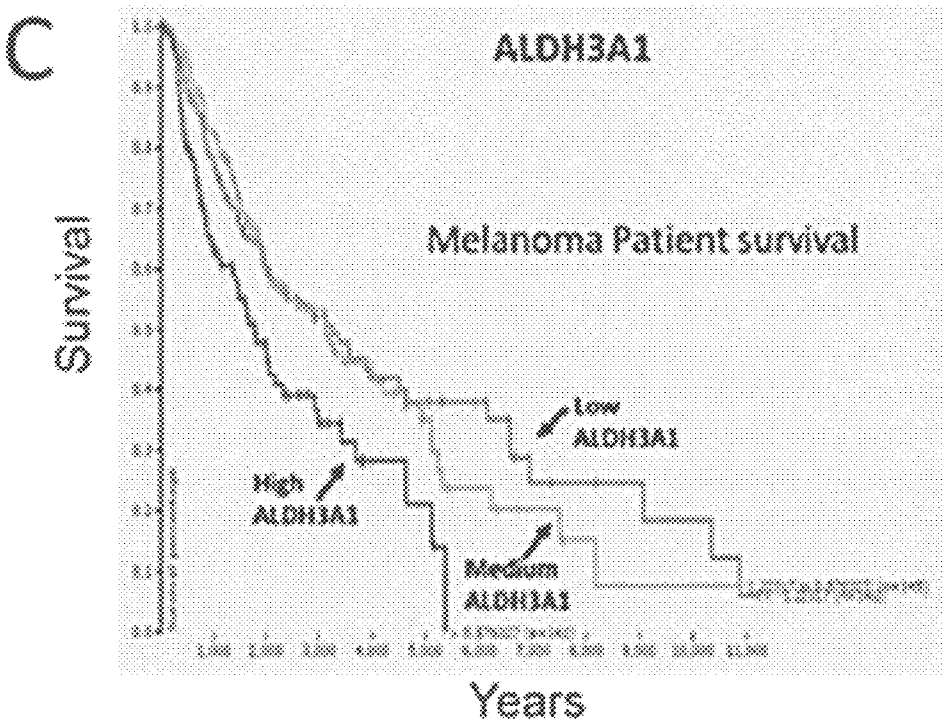

Analysis of the TCGA database to determine the relationship of ALDH overexpression on melanoma patient survival yielded variable results. Specifically, overexpression of ALDH1A1 and 2 was associated with slightly improved survival (FIG. 1B) while high ALDH3A1 expression was associated with lower survival (FIG. 1C).

Figure 1D:
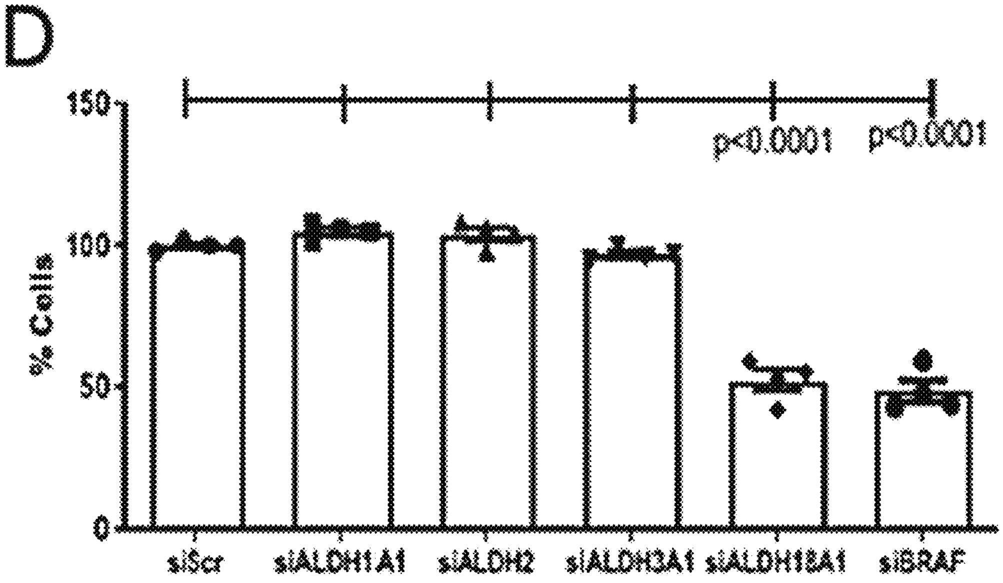
Figure 1E:
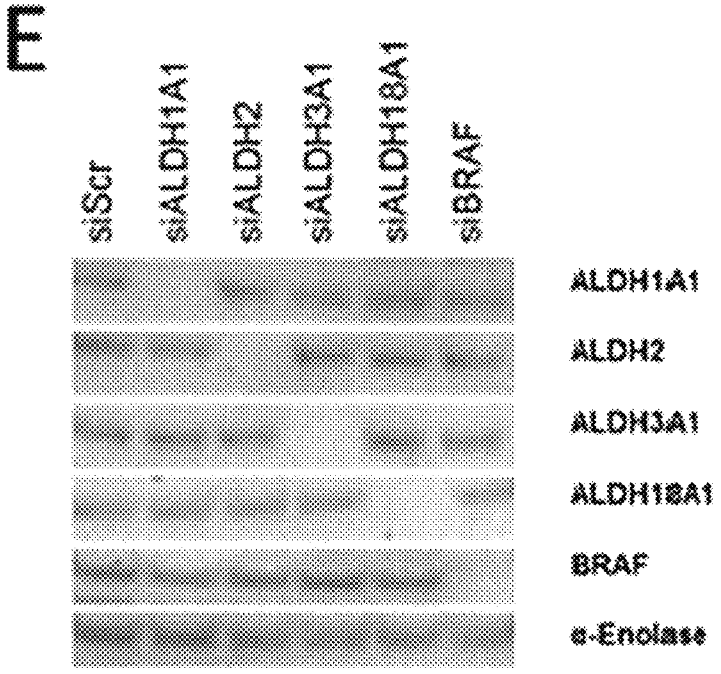
Figure 1F:
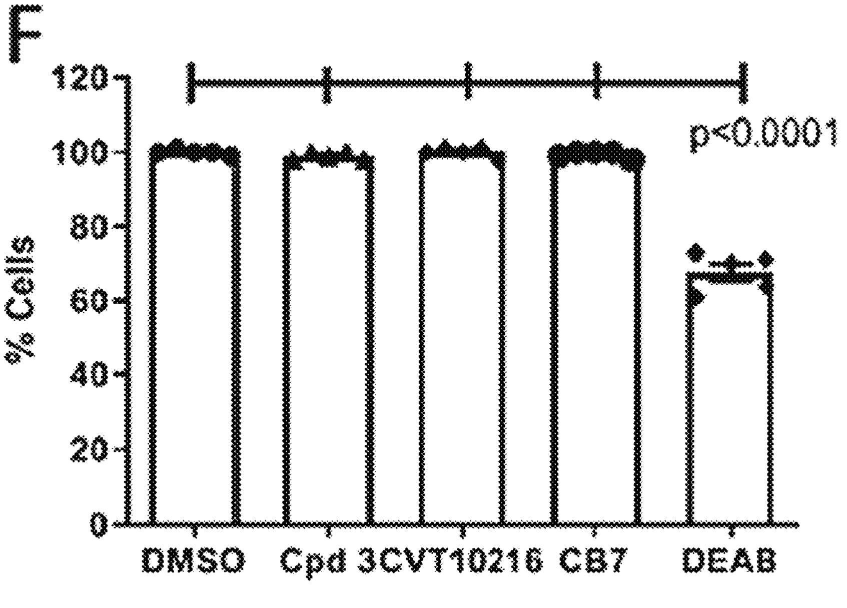

To functionally determine whether targeting ALDH1A1, 2 or 3A1 in melanoma effects cell proliferation, a rapid siRNA screen was undertaken (FIG. 1D). siRNA for ALDH18A1, a unique ALDH isoform that promotes melanoma cell survival, and V600EBRAF were used as positive controls. Knockdown of each respective protein by its siRNA is shown in FIG. 1E. Similar to the scrambled siRNA, individual siRNA knockdown of ALDH1A1, 2 and 3A1 did not affect UACC 903 cell growth up to 72 hours compared to the positive control siRNAs, which caused a ~50% reduction in cell survival (FIG. 1D). These data are consistent with previous reports in which knockdown of ALDH1A1, 2 and 3A1 had minimal effect on cancer cell proliferation. Pharmacological inhibition of ALDH1A1, 2 and 3A1 by isoform-specific inhibitors also had no effect on cell proliferation, even when 100 μM concentrations were used for 72 hours (FIG. 1F). In contrast, DEAB, a multi-ALDH isoform inhibitor, reduced UACC 903 cell survival by 30% at a 100 μM concentration after 72 hours. This result suggested that targeting multiple ALDH isoforms with overlapping function may be more effective for melanoma therapy specifically and anti-cancer therapy in general.

Identification and Development of the Potent, Multi-ALDH Isoform Inhibitor, Called KS100.

To create a multi-ALDH isoform inhibitor, an in silico screen was initially undertaken based on the x-ray crystal structure of ALDH1A1 using various natural products. Isatin was identified during this screen as weakly binding to ALDH1A1 compared to the ALDH1A1 specific inhibitors Cpd 3 and CM037. A medicinal chemistry approach was subsequently undertaken to design compounds that would bind and interact more effectively in the ligand-binding pocket of the ALDHs, using the backbones of Isatin and Cpd 3. A series of compounds were tested through in silico modeling to determine whether they had optimal docking in the ligand-binding pocket of ALDH1A1, and KS100 was selected as the best candidate. It was also found to fit well into the ligand-binding pockets of ALDH2 and 3A1. KS100 had docking scores of −10.247, −8.716 and −13.851 for ALDH1A1, 2 and 3A1, respectively (Table 1), compared to −11.276, −11.004 and −14.576 for the crystal ligands CM037 bound to ALDH1A1, psoralen bound to ALDH2 and CB7 bound to ALDH3A1, respectively.

TABLE 1

| | Docking scores | | |
|---|---|---|---|
| Compound | ALDH1A1 | ALDH2 | ALDH3A1 |
| Crystal Ligand | −11.276 | −11.004 | −14.576 |
| Isatin | −5.46 | −6.398 | −5.819 |
| Cpd 3 | −7.686 | −9.839 | −7.695 |
| CM037 | −11.276 | −7.137 | −8.137 |
| CVT10216 | −7.892 | −11.809 | −8.924 |
| CB7 | −8.159 | −7.846 | −14.576 |
| DEAB | −9.154 | −10.026 | −11.211 |
| KS100 | −10.247 | −8.716 | −13.851 |

Figure 2:
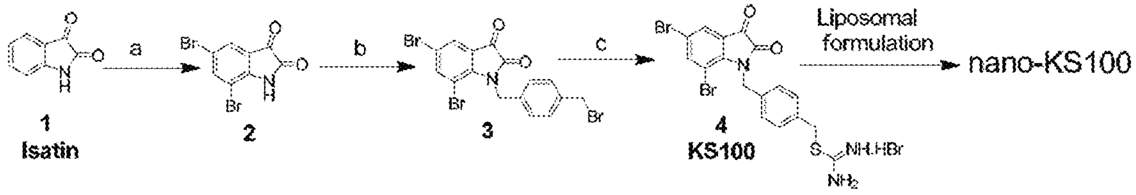
FIG. 2. Synthesis of the ALDH1A1, 2 and 3A1 inhibitor, called KS100. KS100 was synthesized from 5,7-dibromoisatin followed by benzylation as detailed in the materials and methods.

Docking scores indicated strong binding of KS100 to ALDH1A1, 2 and 3A1. KS100 had a π-π interaction with the W178 residue and a H-bond with the free amine group within the ALDH1A1 ligand-binding pocket. Similarly, KS100 had π-π interactions with the F459 and F465 residues along with a H-bond interaction between the free amine group and L269 residue within the ALDH2 ligand-binding pocket. Further, KS100 had a π-π interaction with the R292 residue and a H-bond interaction with the G187 residue in ALDH3A1 ligand-binding pocket. Due to strong broad-spectrum ALDH binding, KS100 was then synthesized through the scheme shown in FIG. 2 for further testing.

Inhibition of the ALDH1A1, 2 and 3A1 isoforms by KS100 was then evaluated and compared to Isatin, the ALDH1A1 specific inhibitors Cpd 3 and CM037, the ALDH42 specific inhibitor CVT10216, the ALDH3A1 specific inhibitor CB7, and the multi-ALDH isoform inhibitor, DEAB (Table 2).

TABLE 2

| | $IC_{50}$s (nM) | | |
|---|---|---|---|
| Compound | ALDH1A1 | ALDH2 | ALDH3A1 |
| Isatin | 15,635 ± 1,821 | 168,661 ± 28,679 | 5,047 ± 304 |
| Cpd 3 | 44 ± 12 | 72,136 ± 1,640 | 11,866 ± 548 |
| CM037 | 98 ± 34 | 2,278 ± 250 | 1,774 ± 303 |
| CVT10216 | 2,427 ± 194 | 53 ± 2 | 2,719 ± 608 |
| CB7 | 139,016 ± 16,934 | 144,409 ± 11,470 | 298 ± 29 |
| DEAB | 89 ± 23 | 833 ± 277 | 15,119 ± 4,091 |
| KS100 | 207 ± 10 | 1,410 ± 248 | 240 ± 50 |

Isatin was a relatively ineffective inhibitor of all ALDH isoforms studied, having $IC_{50}$s of 15.6 μM for ALDH1A1, >160 μM for ALDH2 and 5 μM for ALDH3A1. KS100 was an effective inhibitor of ALDH1A1 activity, having an $IC_{50}$ of 207 nM compared to 44 nM and 98 nM for Cpd 3 and CM037, respectively. KS100 was also an effective inhibitor of ALDH2 activity, having an $IC_{50}$ of 1.41 μM compared to 53 nM for CVT10216. Finally, KS100 effectively inhibited ALDH3A1 activity, having an $IC_{50}$ of 240 nM compared to 298 nM for CB7. DEAB was slightly superior to KS100 in inhibiting ALDH1A1 and ALDH-2 activity, having $IC_{50}$s of 89 nM and 833 nM, respectively, for these isoforms. However, DEAB was inferior to KS100 in inhibiting ALDH3A1, having an $IC_{50}$ of 15.1 μM for this isoform. Collectively, these results show the successful development of a novel, potent, ALDH1A1, 2 and 3A1 inhibitor.

Specificity of KS100, for ALDH Isoforms.

To identify off-target effects of KS100, the binding scaffold of KS100 as a substructure was extracted and employed in Erebus, a protein substructure search server. During the substructural search against the PDB database, few similar rigid binding scaffolds were identified. To precisely identify the most similar binding scaffolds to our query structure, a cut-off RMSD of ≤7 Å was imposed in the query, with the subsequent hits listed in Table 3.

TABLE 3

| PDB ID | Atoms | Residues | RMSD (Å) | Description | Organism |
|---|---|---|---|---|---|
| 4WB9 (Query) | 33 | 13 | 2.24 | Crystal structure of human ALDH1A1 complexed with NADH | *Homo sapiens* |
| 4URH | 26 | 14 | 6.87 | Crystal structure of high-resolution structure of partially oxidized *D. fructosivorans* NiFe-hydrogenase | *Desulfovibrio fructosivorans* |

The identification of ALDH1A1 as the primary hit highlights the accuracy of the Erebus algorithm. The RMSD of ~2.24 Å between the query and the primary hit is likely due to the flexible docking approach used during initial docking of KS100 to ALDH1A1. Apart from ALDH1A1, NiFe-hydrogenase from *Desulfovibrio fructosivorans* was identified as having a similar substructural scaffold. Besides these identified scaffolds, KS100 appears to have no off-target effects in humans based on the Erebus algorithm, indicating the specificity of KS100 binding to human ALDHs.

Assessing the Toxicity of KS100.

Figures 3A, 3B:
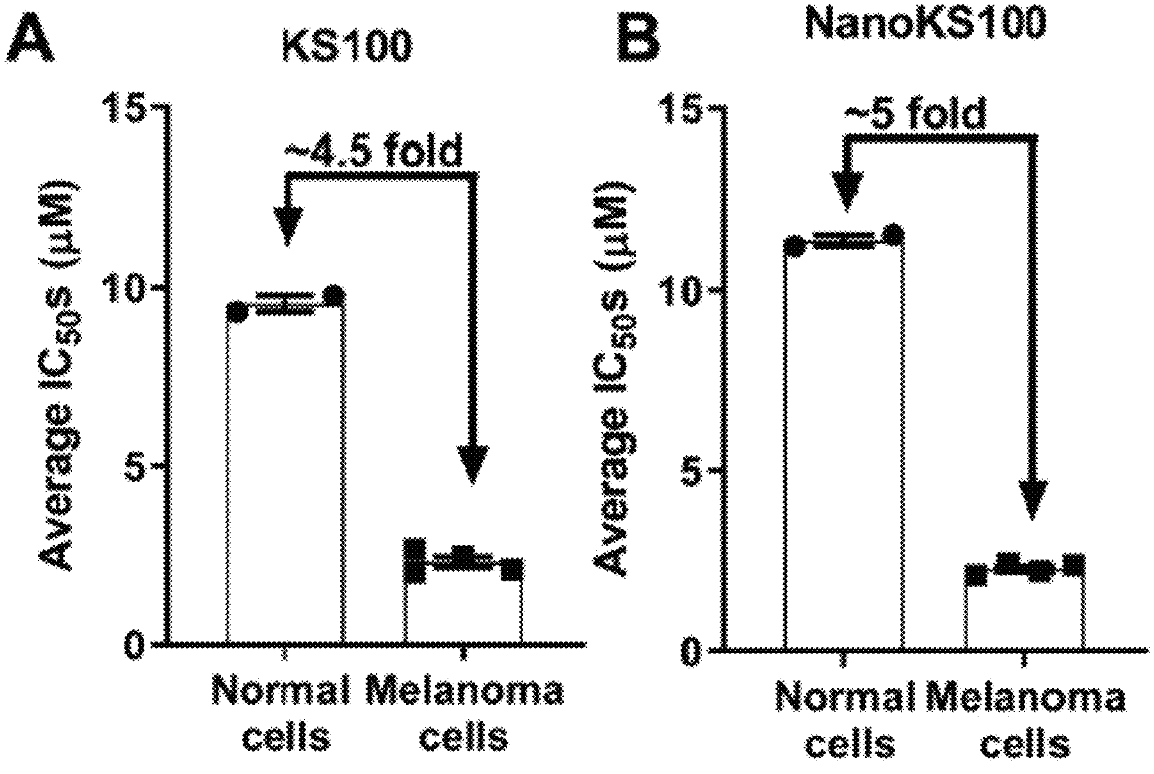
FIGS. 3A-3B. KS100 (FIG. 3A) and NanoKS100 (FIG. 3B) preferentially killed melanoma cells. Cell killing $IC_{50}$s for KS100 and NanoKS100 against BRAF mutant (UACC 903, 1205 Lu) and wildtype (C8161.CI9, MelJuSo) melanoma cell lines were calculated and compared to that of normal human fibroblasts (FF2441) and melanocytes (NHEM). KS100 was ~4.5-fold and NanoKS100 was ~5-fold more selective for killing melanoma cells compared to FF2441 and NHEM cells.

The efficacy and specificity of KS100 for killing cultured melanoma cells (UACC 903, 1205 Lu, MelJuSo, C8161.Cl9) was examined by MTS assay and compared to FF2441 and NHEM cells. The $IC_{50}$ killing efficacy of KS100 on FF2441 and NHEM cells was 9.32 μM compared to 2.02 μM across all melanoma cell lines tested, irrespective of BRAF mutational status, amounting to a killing selectivity index of ~4.5-fold higher for melanoma cells (FIG. 3A).

Since KS100 was identified to be a potent multi-ALDH isoform inhibitor, it was predicted to have toxicity in animals. To test the in vivo toxicity of KS100, Swiss Webster mice were treated with daily i.p. administration of KS100 at 5, 10 and 15 mg/kg body weight and compared to DMSO control (Table 4).

TABLE 4

| Daily dose (mg/kg body weight) for 7 days | KS100 i.p. administration | | | NanoKS100 i.v. administration | | |
|---|---|---|---|---|---|---|
| | Average % weight loss compared to control | Behavioral parameters indicating toxicity | Mortality at day 7 | Average % weight loss compared to control | Behavioral parameters indicating toxicity | Mortality at day 7 |
| 5 | 16.6 | Hunched back; lethargic | 0/3 | 0.67 | None | 0/3 |
| 10 | N/A | N/A | 3/3 | 1.02 | None | 0/3 |
| 15 | N/A | N/A | 3/3 | 2.54 | None | 0/3 |
| 30 | — | — | — | 1.32 | None | 0/3 |
| 60 | — | — | — | 0.84 | None | 0/3 |

A 16.6% decrease in animal body weight, on average, along with hunched backs and lethargy were observed at day 7 with the 5 mg/kg treatment group. All animals treated with 10 and 15 mg/kg of KS100 died before day 7, indicating significant toxicity. Thus, the toxicity associated with KS100 necessitated the development of a formulation with controlled release of the drug to eliminate these effects.

Developing a Nontoxic, Effective, Stable Nanoliposomal Formulation of KS100, Called NanoKS100.

Figure 4A:
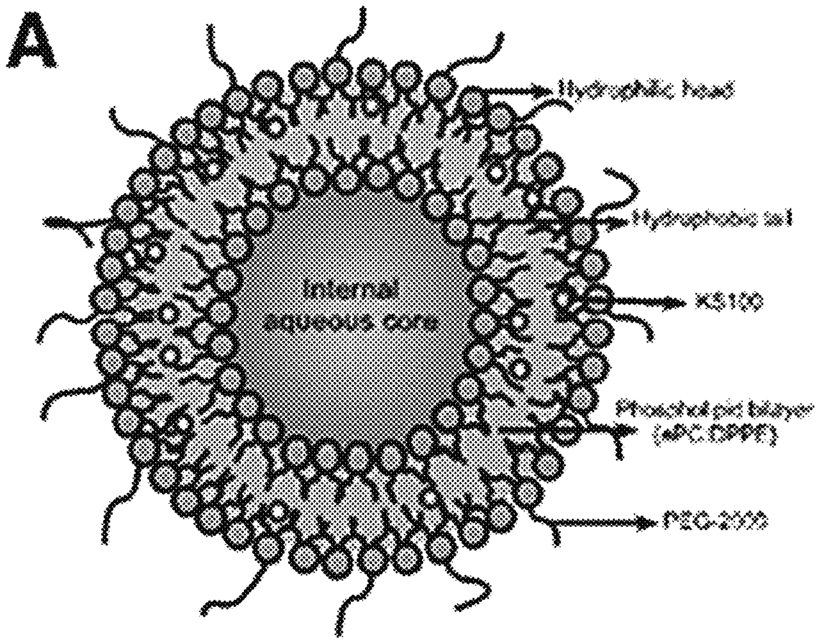
FIGS. 4A-4H. Development and characterization of the nanoliposomal formulation of KS100, called NanoKS100. NanoKS100 consists of an aqueous core surrounded by a phospholipid bilayer. KS100 is contained within the phospholipid bilayer (FIG. 4A). NanoKS100 was manufactured with a 68.6% loading efficiency of KS100 into nanoliposomes (FIG. 4B). KS100 is released from the nanoliposomal formulation continuously for 48 hours with the maximal release of 70% (FIG. 4C). Cell killing $IC_{50}$s for KS100 and NanoKS100 against BRAF mutant (UACC 903, 1205 Lu) and wild-type (C8161.CI9, MelJuSo) melanoma cell lines were calculated and compared with that of normal human fibroblasts (FF2441) and melanocytes (NHEM, FIG. 4D). KS100 was approximately 4.5-fold, and NanoKS100 was approximately 5-fold more selective for killing melanoma cells compared with FF2441 and NHEM cells. NanoKS100 is stable for at least 12 months when stored at 4° C. with no significant changes in $IC_{50}$s (FIG. 4E), size (FIG. 4F), or charge (FIG. 4G). NanoKS100 causes significantly lower hemolysis compared with KS100 in both mouse and rat red blood cells. Triton X-100 served as the positive control (FIG. 4H).
Figure 4B:
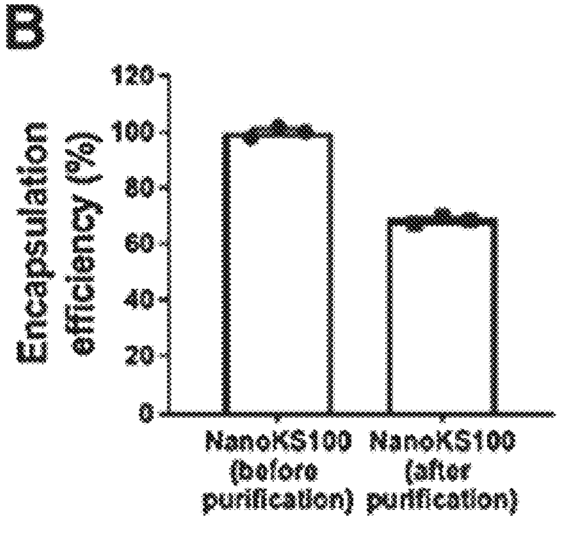
Figure 4C:
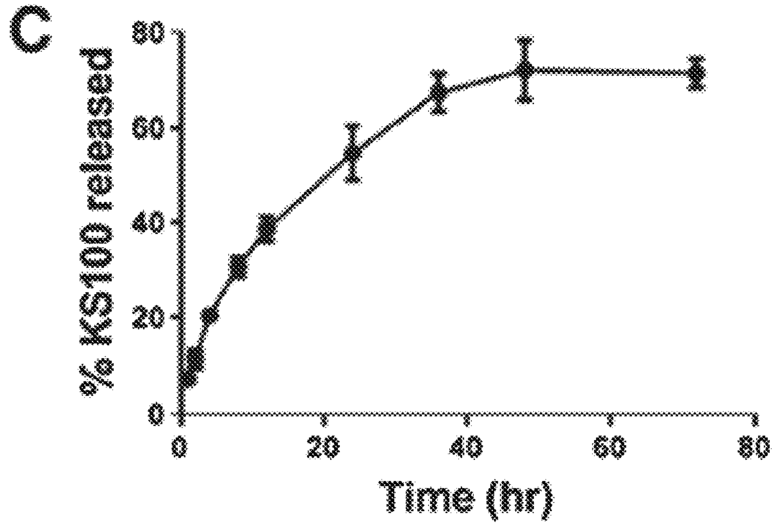

KS100 was loaded into a nanoliposomal formulation, called NanoKS100, and the physiochemical properties of NanoKS100 were analyzed. A schematic representation of NanoKS100 is shown in FIG. 4A where KS100 is trapped in the phospholipid bilayer with an internal aqueous core. The maximum loading efficiency of KS100 into nanoliposomes was 68.6% (FIG. 4B) and the size of NanoKS100 was identified to be 78.5 nm, with an average charge of +0.54 eV in saline at the day of manufacture (FIGS. 4F-4H).

The efficacy and specificity of NanoKS100 for killing cultured melanoma cells was examined by MTS assay and compared to FF2441 and NHEM cells. The $IC_{50}$ killing efficacy of NanoKS100 on FF2441 and NHEM cells was 11.5 μM compared to 2.3 μM across all melanoma cell lines tested, irrespective of BRAF mutational status, amounting to a killing selectivity index of ~5-fold higher for melanoma cells, similar to that of KS100 (FIG. 3B). Thus, KS100 maintained its melanoma cell killing efficacy and selectivity in the NanoKS100 formulation.

Since intravenous (i.v.) dosing of nanoliposomes can trigger hemolysis at the injection site, the effect of NanoKS100 on red blood cell (RBC) lysis was examined. RBCs from mice and rats were incubated with KS100 or NanoKS100 for 1 hour and the amount of hemolysis was quantified. KS100 caused 27% and 19% hemolysis of mouse and rat RBCs, respectively, compared to 100% hemolysis with the Triton X-100 positive control (FIG. 4C'). However, NanoKS100 lysed <5% of RBCs in both groups indicating a protective effect of the nanoliposomal formulation.

Figure 4D:
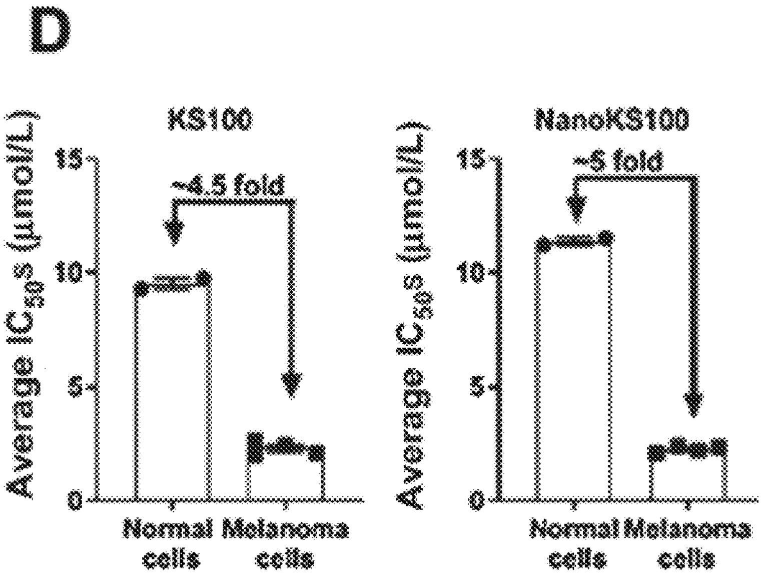
Figure 4E:
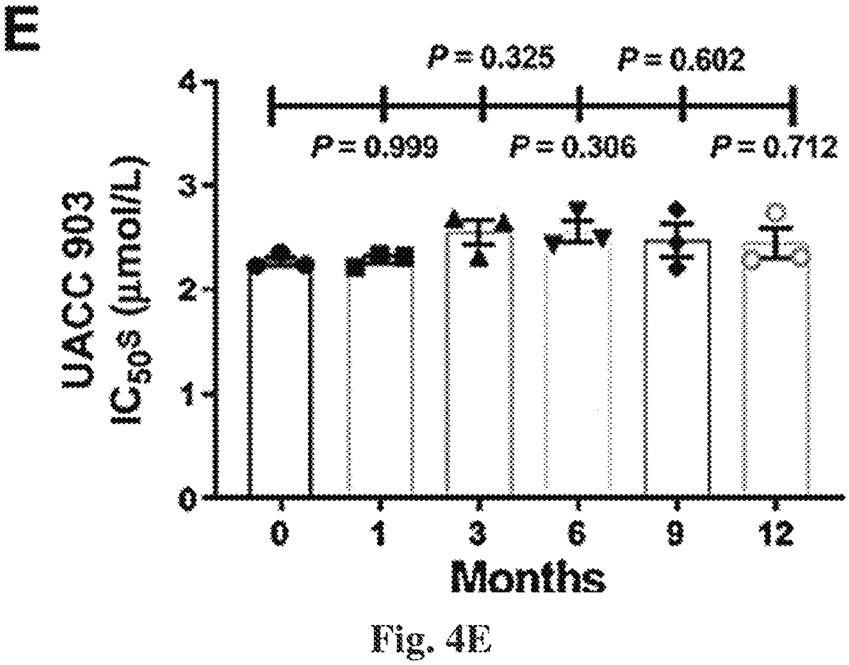
Figure 4F:
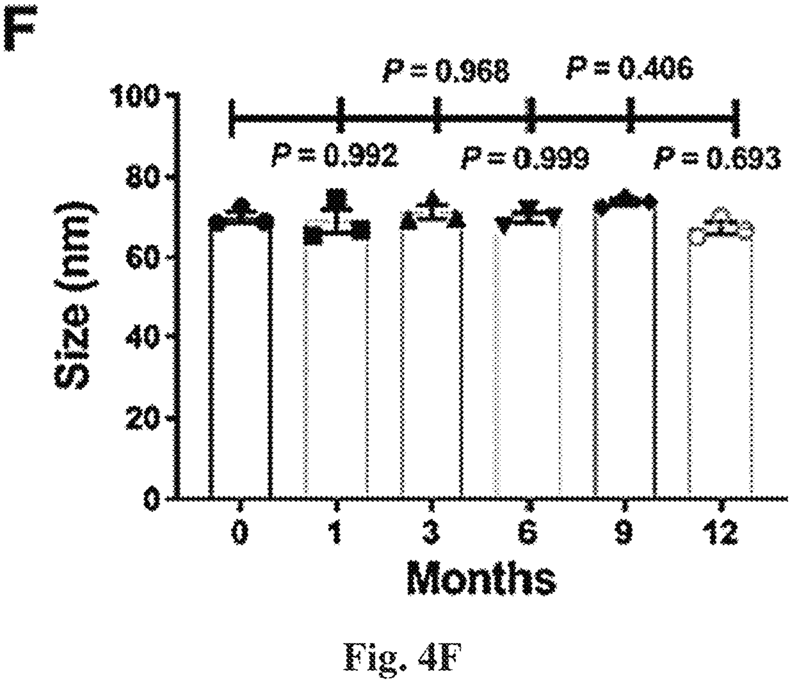
Figure 4G:
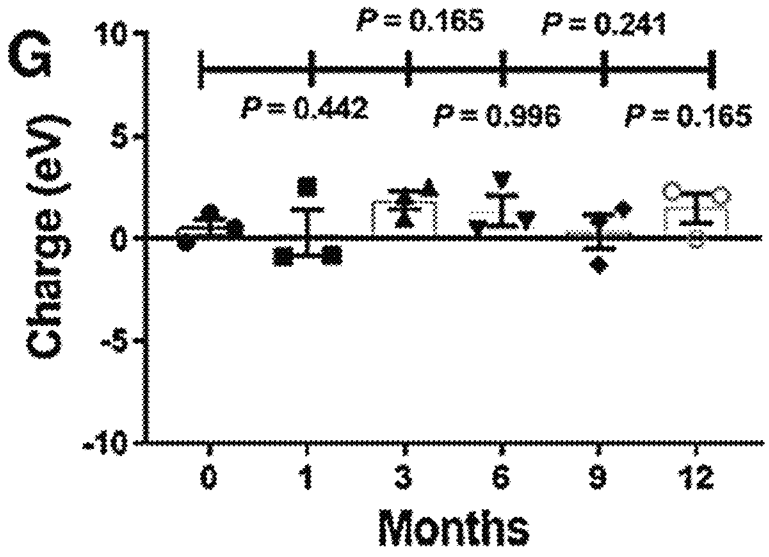
Figure 4H:
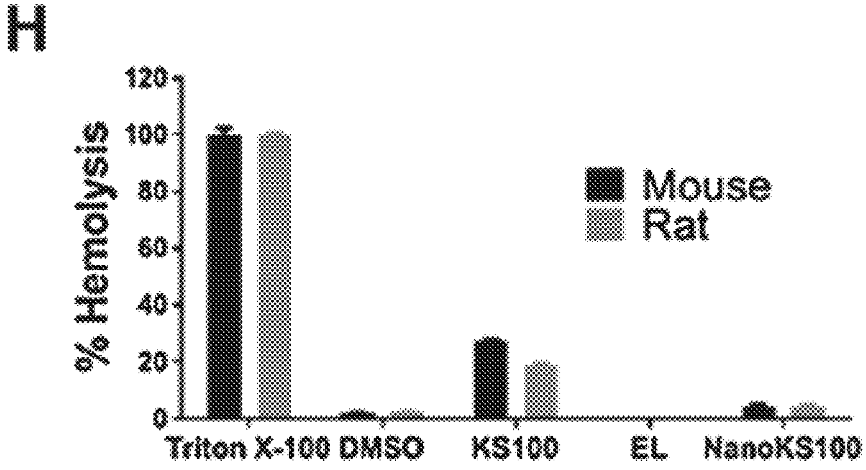

Release kinetics of NanoKS100 were examined and revealed continuous release of the agent over 48 hours with maximal release of 70% occurring by 48 hours (FIG. 4D). The cell killing $IC_{50}$s (FIG. 4E), size (FIG. 4F) and charge (FIG. 4G) of NanoKS100 did not vary significantly over a 12-month period when stored at 4° C., indicating stability of the formulation.

Toxicity of NanoKS100 was examined in Swiss Webster mice treated with i.v. NanoKS100 at 5-60 mg/kg for 7 days and compared to empty liposome vehicle control. Results revealed negligible weight loss on average (0.6 to 2.5%), with no mortality or abnormal behavioral changes seen in any of the NanoKS100 treatment groups (Table 3). The maximum dose that could be administered to animals was 60 mg/kg as the nanoliposomes of NanoKS100 were not stable above this loaded concentration. A maximum tolerated dose of NanoKS100 could thus not be attained, as doses above 60 mg/kg could not be tested.

NanoKS100 Inhibits Melanoma Tumor Development with No Apparent Toxicity in Animals.

Figure 5A:
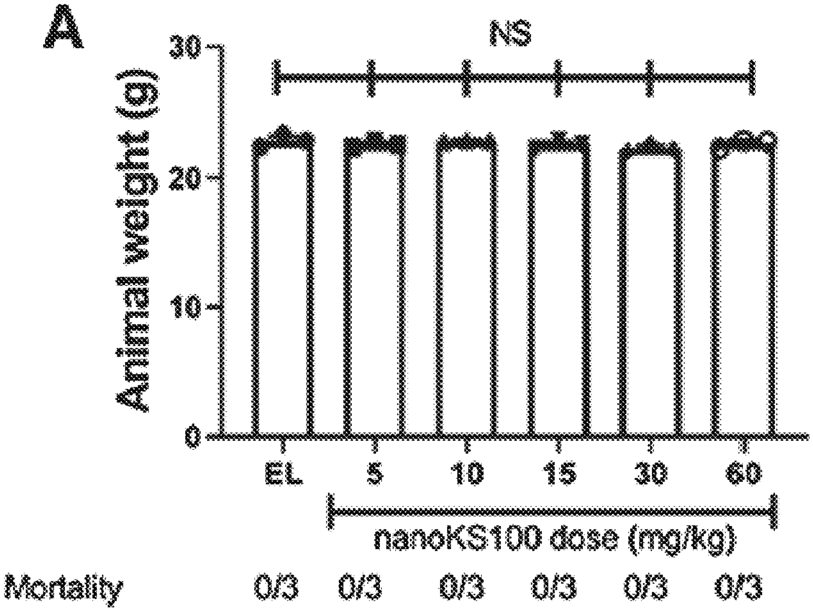
FIGS. 5A-5E. NanoKS100 inhibited melanoma tumor growth with negligible toxicity. A 7-day repeated dose study was conducted for NanoKS100. NanoKS100 was administered i. v. daily at various doses, whereas animal body weight, physical and behavioral changes, and mortality were monitored (FIG. 5A). NanoKS100 significantly inhibited tumor growth of UACC 903 xenografts compared with empty liposome vehicle control following 20 days of treatment. No significant difference in tumor growth was seen between the NanoKS100 treatment groups (FIG. 5B). NanoKS100 at 20 mg/kg body weight administered daily i.v. led to an approximately 65% reduction in tumor growth in UACC 903 (FIG. 5C) and 1205 Lu (FIG. 5D) xenografts following 20 to 22 days of treatment. NanoKS100 did not significantly affect animal body weight (FIG. 5C, FIG. 5D-insets) or serum biomarkers of toxicity (FIG. 5E) compared with empty liposome vehicle control. Normal reference ranges for serum biomarkers are included.
Figure 5B:
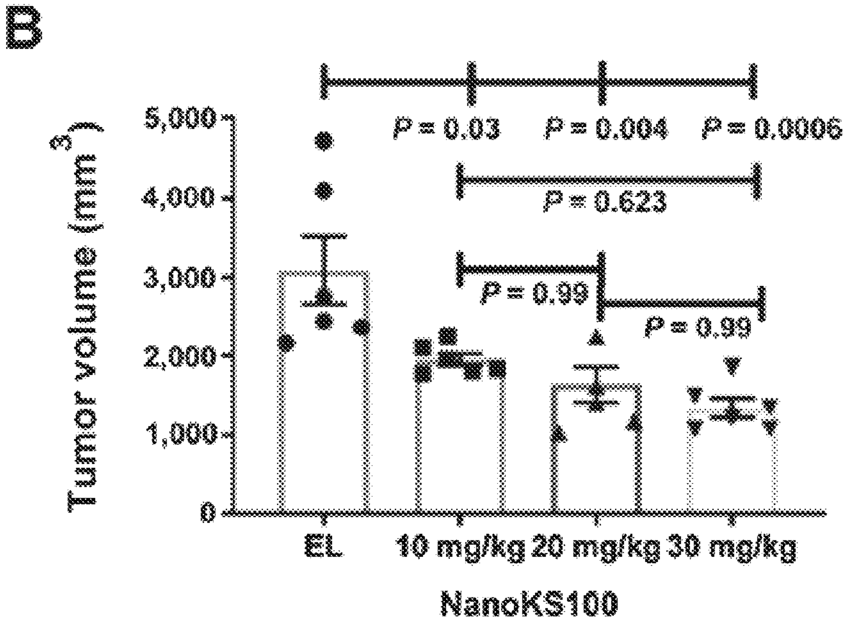

Having identified the safe dose range of NanoKS100, 3 doses (10, 20 and 30 mg/kg body weight) were selected for in vivo tumor inhibitory studies. UACC 903 melanoma cells were injected into the flanks of nude mice and once vascularized tumors had formed, mice were treated with daily i.v. NanoKS100 at 10, 20 and 30 mg/kg for 20 days. Tumor volumes, animal behavior and weight were monitored every other day. All 3 treatment groups showed significant inhibition of melanoma xenograft growth compared to empty liposome vehicle control (FIG. 5A). No statistically significant differences in toxicity and tumor volumes between treatment groups were observed.

Figure 5C:
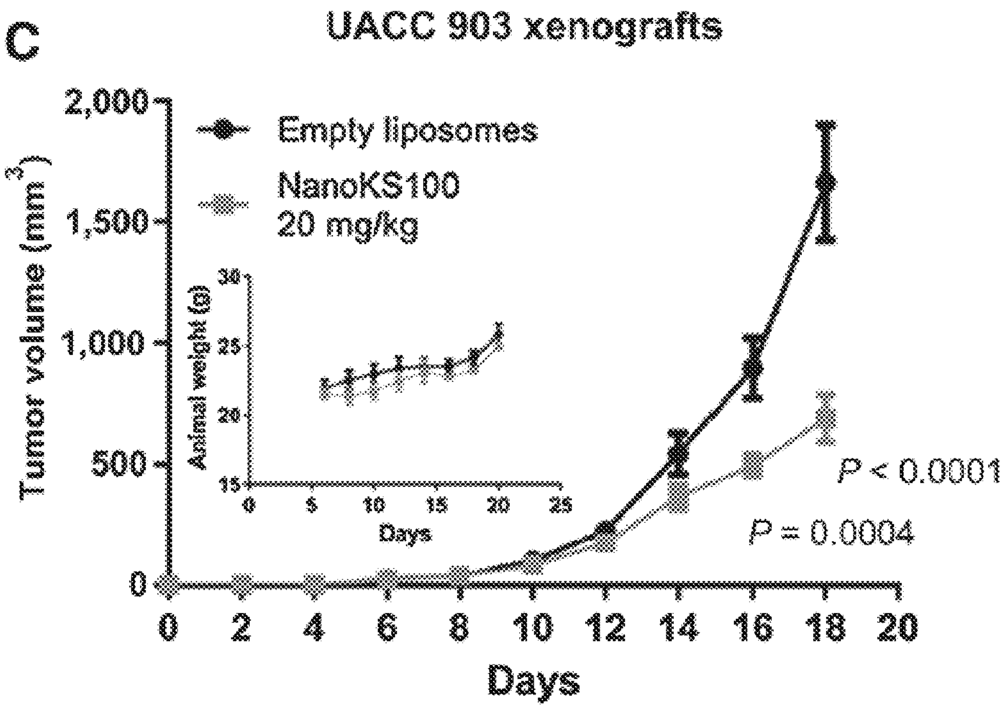
Figure 5D:
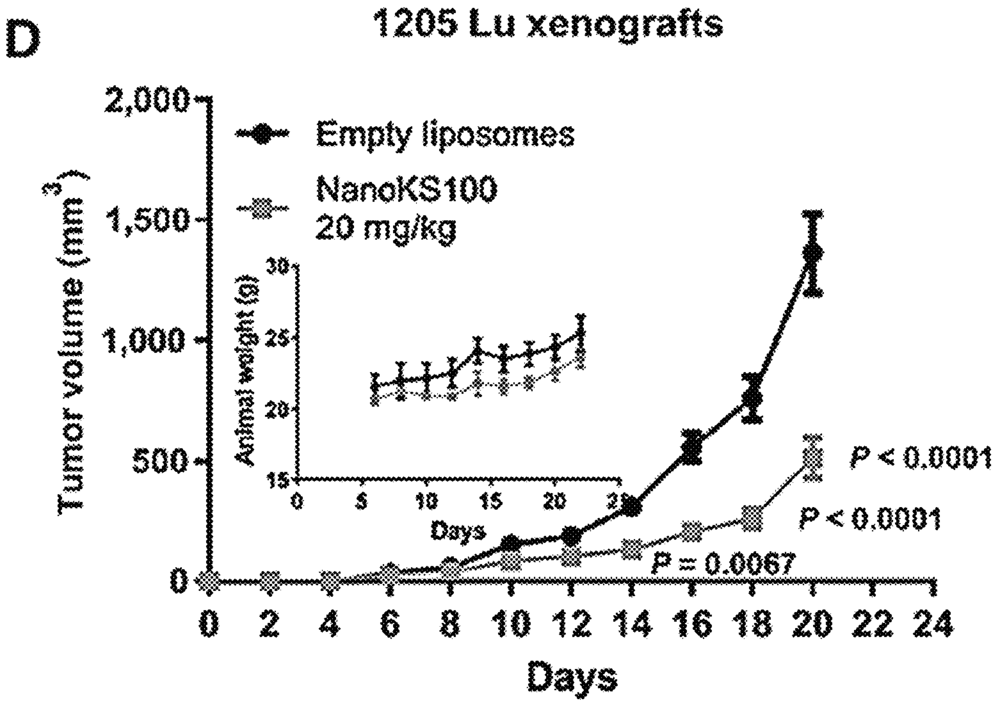
Figure 5E:
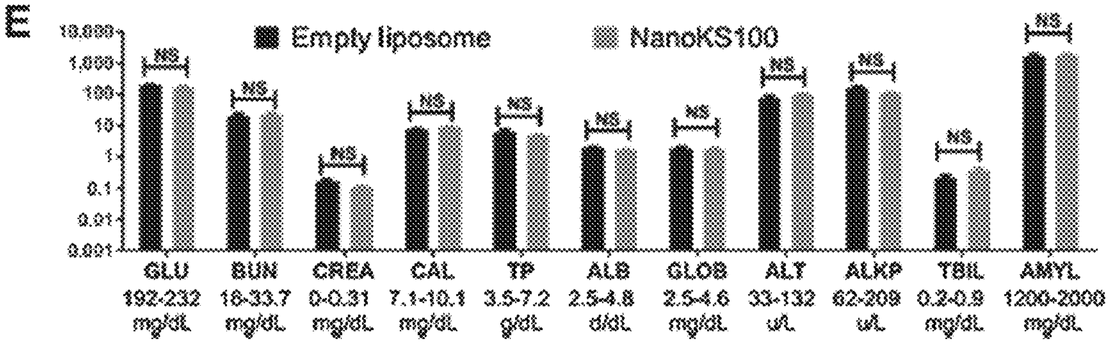

Due to these findings, treatment with 20 mg/kg NanoKS100 administered daily i.v. was selected for further tumor xenograft experiments using both UACC 903 and 1205 Lu melanoma cells. A >65% reduction in tumor volumes was observed for NanoKS100 in both UACC 903 (FIG. 5C) and 1205 Lu (FIG. 5D) xenografts at days 20-22 with no significant reduction in animal weights compared to the empty liposome vehicle control (insets of FIGS. 5C-5D), indicating negligible toxicity. The blood of the mice with UACC 903 xenografted tumors was collected at day 20 and serum biomarkers indicative of major organ toxicity were examined (FIG. 5E). No significant differences in serum biomarkers between NanoKS100 and empty liposome vehicle control were observed. Collectively, these data suggest that daily i.v. administration of a submaximal dose of NanoKS100 (3-fold lower) is safe and effective in this mouse melanoma model.

KS100 Causes Increased Intracellular ROS, Lipid Peroxidation, Toxic Aldehyde Accumulation, Apoptosis and Autophagy in Melanoma Cells.

Figure 6A:
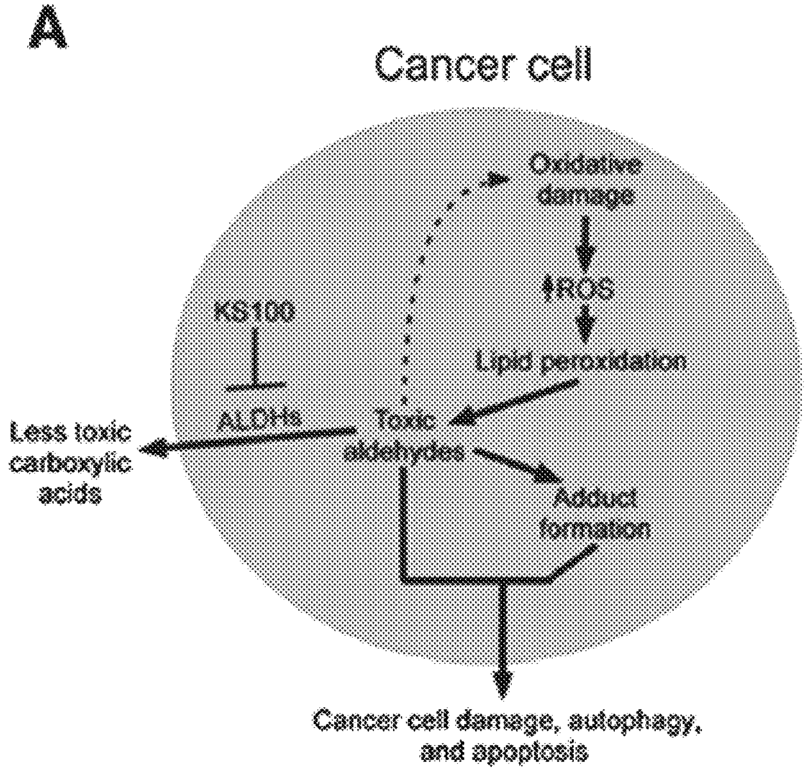
FIGS. 6A-6K. KS100 reduced total cellular ALDH activity to increase ROS generation, lipid peroxidation, and toxic aldehyde accumulation leading to apoptosis and autophagy. The ALDHs reduce ROS generation, lipid peroxidation, and toxic aldehyde accumulation, the latter of which can lead to cell damage and apoptosis (FIG. 6A). KS100 was the only ALDH inhibitor that significantly reduced ALDH cells in both UACC 903 (FIG. 6B) and 1205 Lu (FIG. 6C) cells. ALDH+ cells were analyzed by flow cytometry following staining with AldeRed. DMSO served as the control. UACC 903 (FIG. 6D) and 1205 Lu (FIG. 6E) cells treated with KS100 had increased ROS activity compared with the other ALDH inhibitors tested. DMSO served as control. No ALDH inhibitor significantly increased ROS activity in normal human fibroblasts (FF2441) compared with the DMSO control (FIG. 6F). UACC 903 (FIG. 6G) and 1205 Lu (FIG. 6H) cells treated with KS100 had increased lipid peroxidation and toxic aldehyde accumulation compared with the other ALDH inhibitors tested. DMSO served as the control. Flow cytometric analysis of apoptosis in UACC 903 (FIG. 6I) and 1205 Lu (FIG. 6J) cells treated with 5 mmol/L of ALDH inhibitor for 24 hours showed significantly increased apoptosis with KS100 compared with the other ALDH inhibitors tested in both cell lines. DMSO served as the control. Western blot of increasing concentrations of KS100 (2, 4, and 6 mmol/L) showed increased apoptosis (cleaved-PARP) and autophagy (LC3B) in UACC 903 cells after 24 hours of treatment (FIG. 6K).
Figures 6B, 6C:
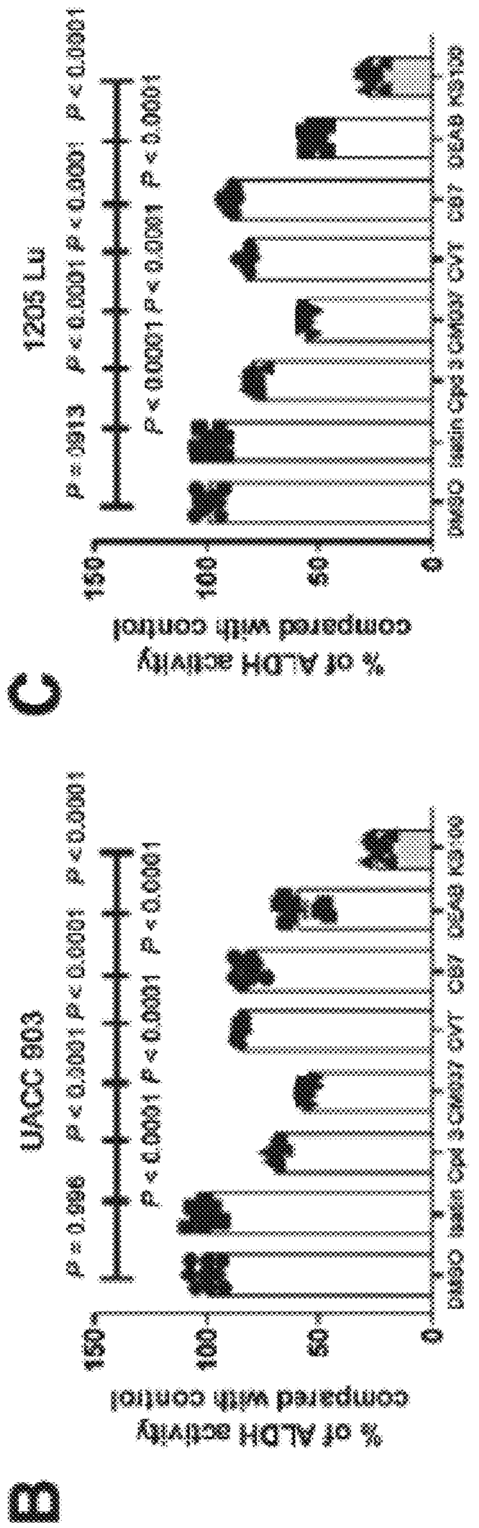

The ALDHs reduce ROS, lipid peroxidation and toxic aldehyde accumulation, the latter of which can lead to cell damage and apoptosis as shown in FIG. 6A. Thus, inhibition of total cellular ALDH activity can increase toxic aldehydes, oxidative damage and apoptosis. To evaluate the effects of KS100 on total cellular ALDH activity, UACC 903 (FIG. 6B) and 1205 Lu (FIG. 6C) cell lysates were treated with 1 uM of ALDH inhibitor or DMSO for 15 minutes followed by the addition of aldehyde substrate mixture. KS100 was the most effective at reducing total cellular ALDH activity in both UACC 903 (75% reduction) and 1205 Lu (73% reduction) cells. The remaining ALDH inhibitors significantly reduced total cellular ALDH activity, particularly CM037 and DEAB, while isatin was ineffective.

Figures 6D, 6E:
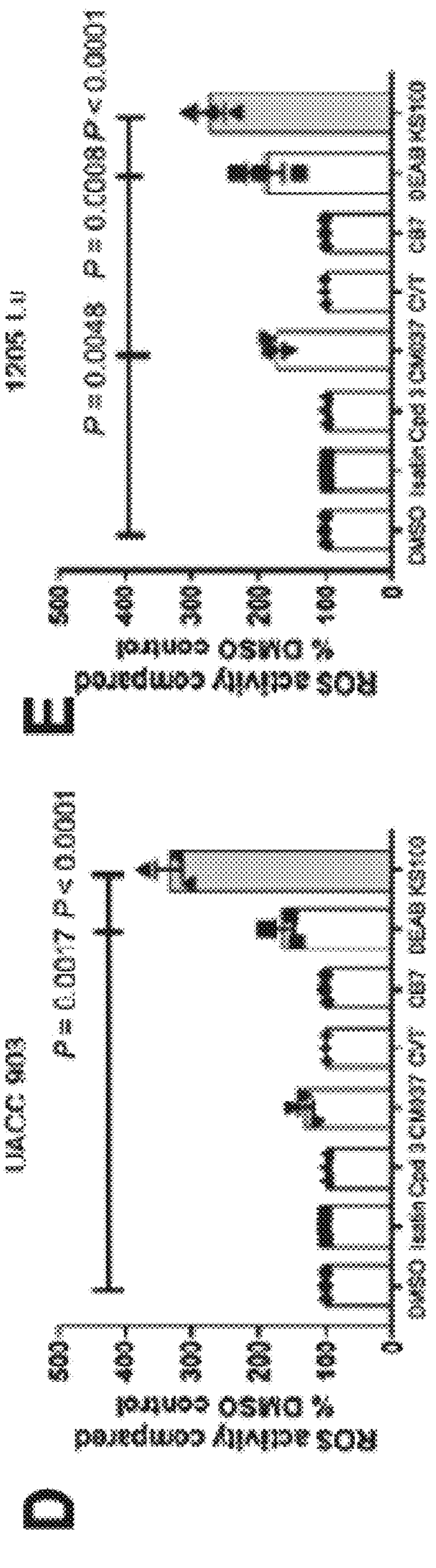
Figures 6F, 6G:
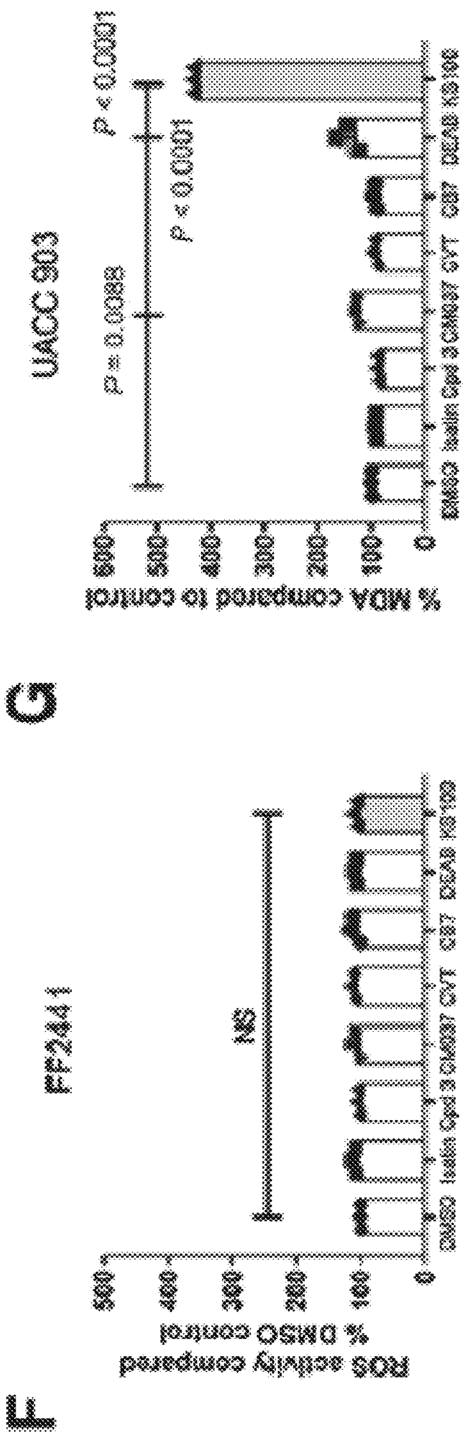
Figure 6H:
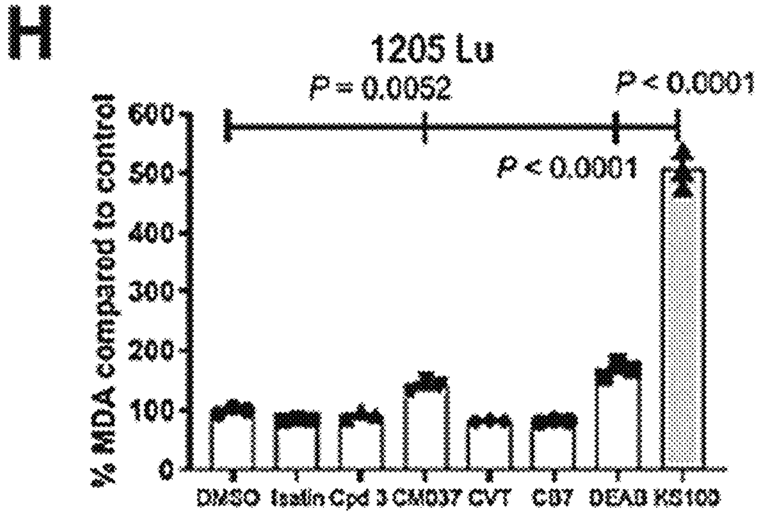

Levels of ROS were measured in UACC 903 (FIG. 6D) and 1205 Lu (FIG. 6E) cells and compared to FF2441 cells (FIG. 6F) following treatment with 5 μM of ALDH inhibitor or DMSO for 24 hours. No ALDH inhibitor had an effect on ROS levels in FF2441 cells (FIG. 6F). KS100 was the most effective at increasing ROS levels in both cell lines (FIGS. 6D-6E). DEAB and CM037 were the only other agents that significantly increased ROS levels in either cell line. Subsequently, levels of lipid peroxidation and toxic aldehyde accumulation were measured in UACC 903 (FIG. 6G) and 1205 Lu (FIG. 6H) cells following treatment with 5 μM of ALDH inhibitor or DMSO for 24 hours. Consistent with the ROS assay, KS100 was the most effective at increasing lipid peroxidation and toxic aldehyde accumulation in both cell lines (FIGS. 6G-6H). DEAB and CM037 were the only other inhibitors that significantly increased lipid peroxidation and toxic aldehyde accumulation in either cell line.

Figure 6I:
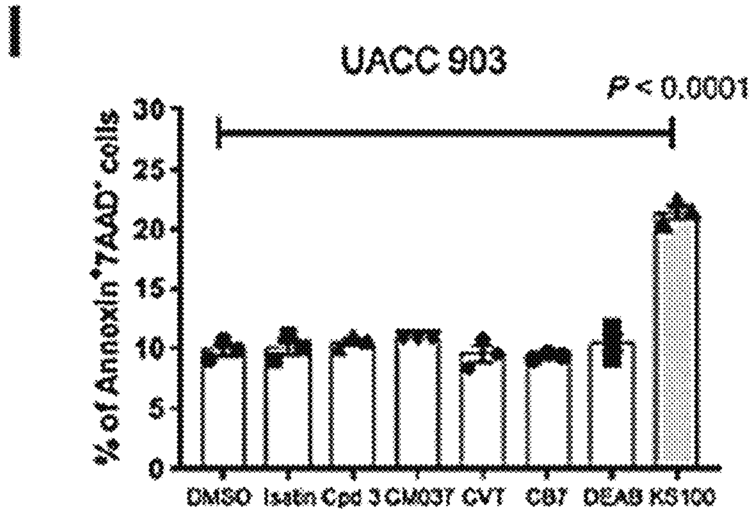
Figures 6J, 6K:
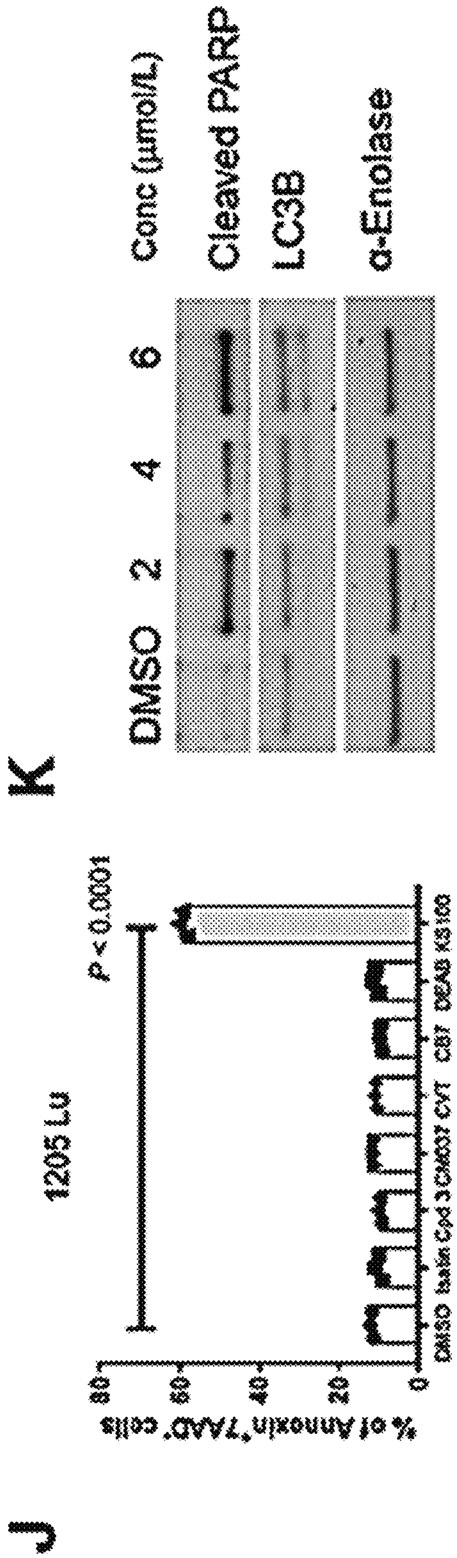
Figure 7:
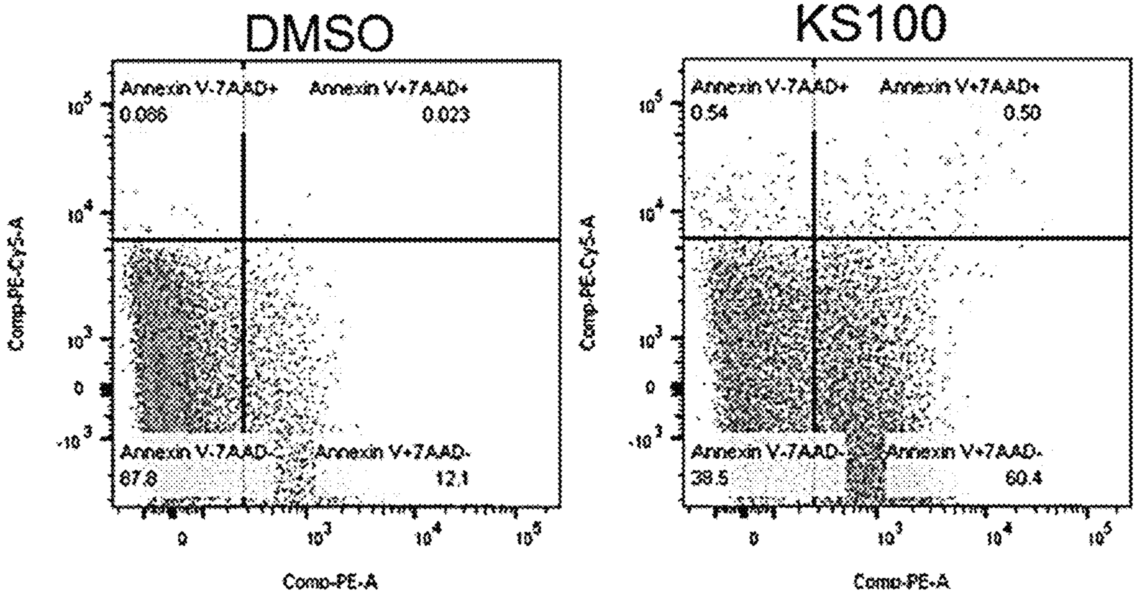
FIG. 7. Representative dot plots of Annexin-V-PE/7-AAD staining of cells following KS100 treatment. 1205 Lu cells were treated with 5 μM KS100 or DMSO for 24 hours and stained for Annexin-V-PE/7-AAD as detailed in the materials and methods.
Figure 8A:
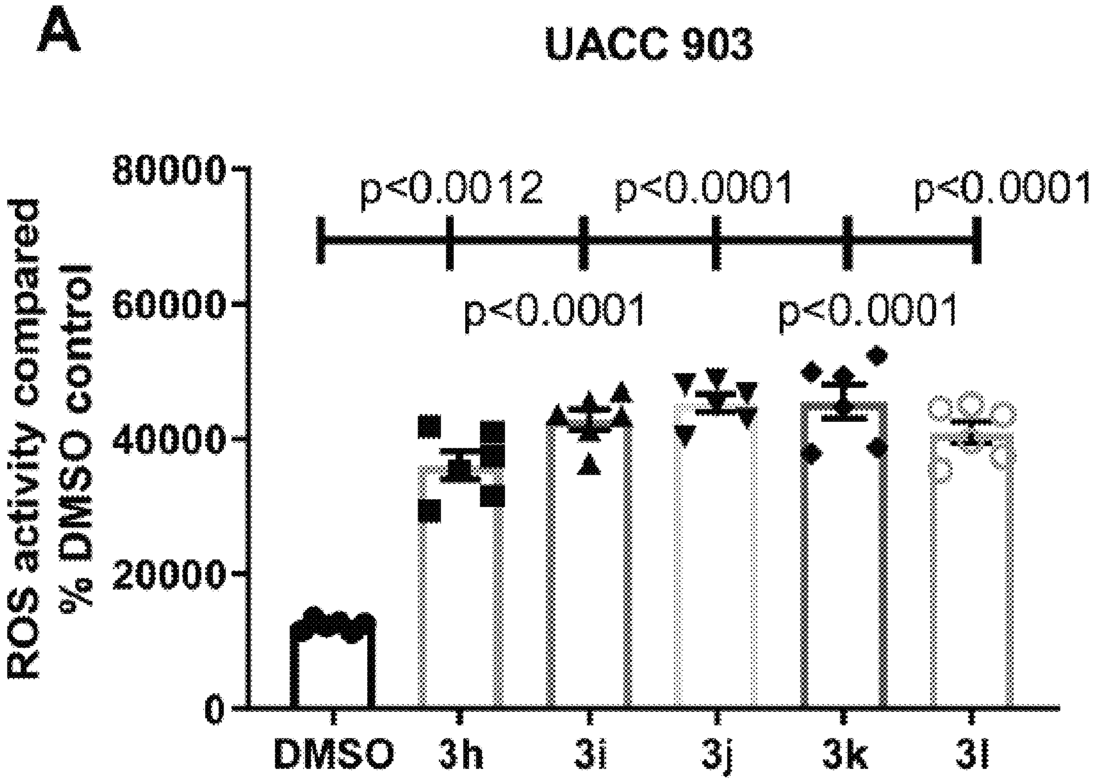
FIGS. 8A-8D. ROS and lipid peroxidation activity and toxic aldehyde accumulation. UACC 903 and 1205 Lu cells were treated with 5 μM of 3h-3l for 24 hours. ROS levels were measured using DCFDA dye and compared to DMSO control. Malondialdehyde (MDA) levels were measured using thiobarbituric acid and compared to DMSO control.
Figure 8B:
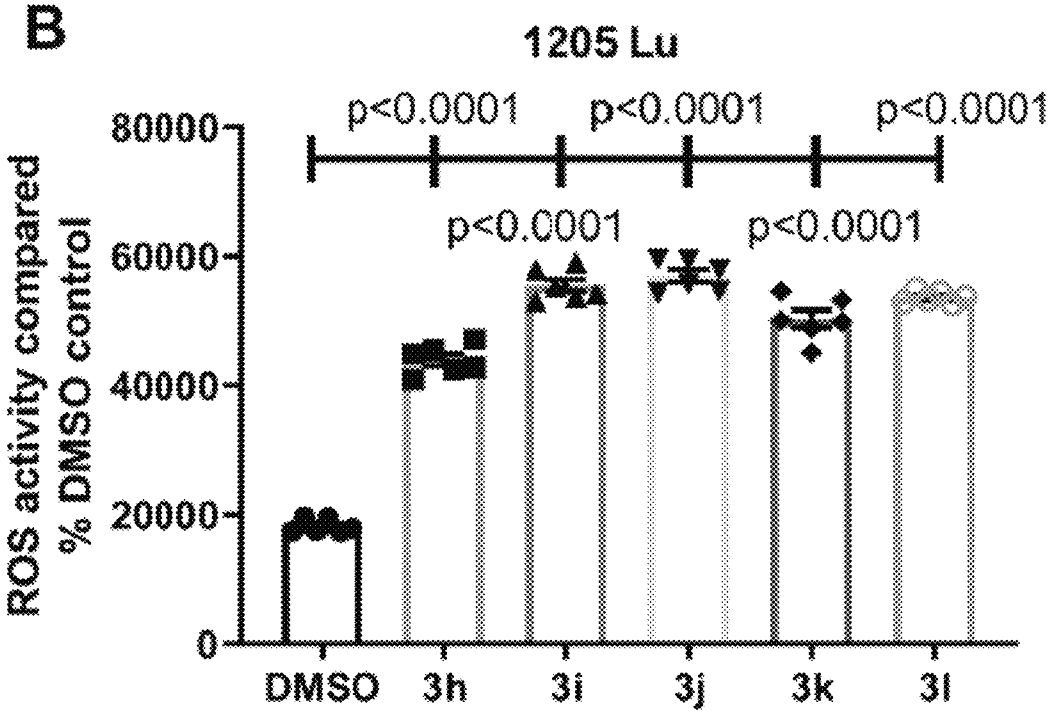
Figure 8C:
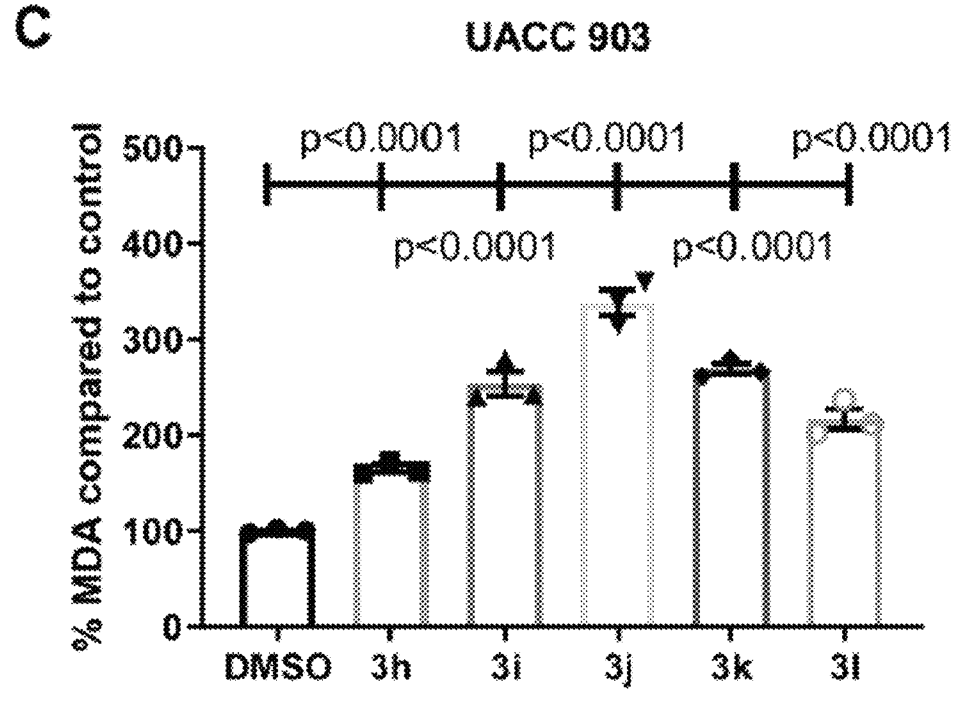
Figure 8D:
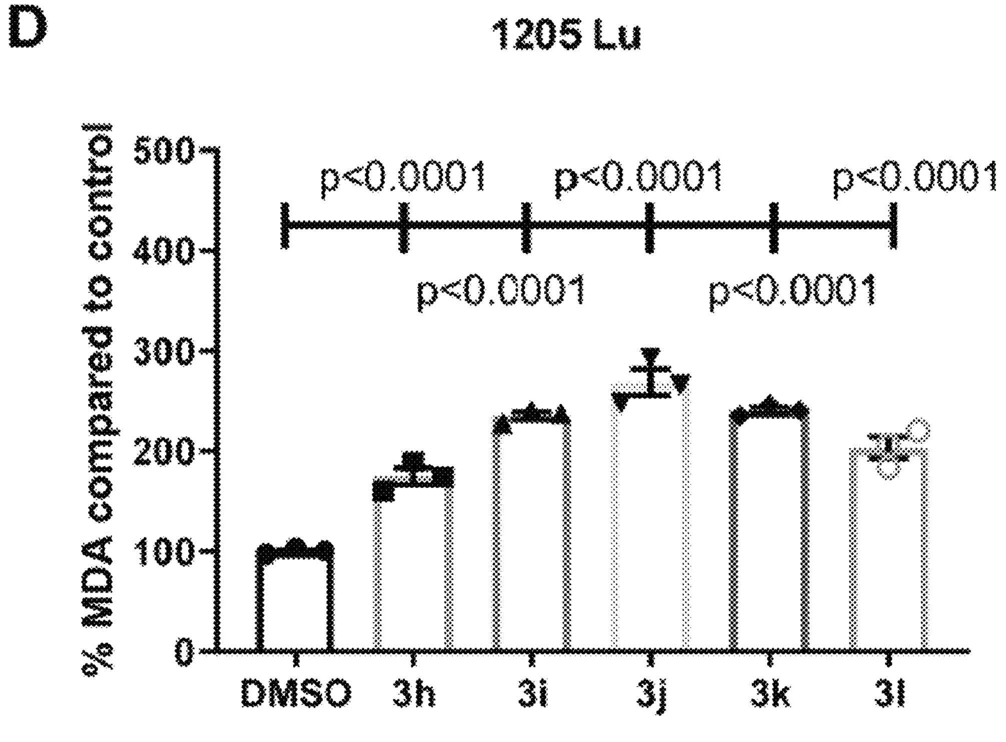
Figure 9:
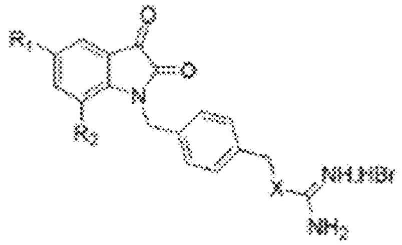
FIG. 9. Structures and docking scores of 3(a-l) and 4(a-l). Docking scores were calculated for compounds against ALDH1A1, 2 and 3A1 using the Glide module of Schrodinger.
Figures 12, 13A:
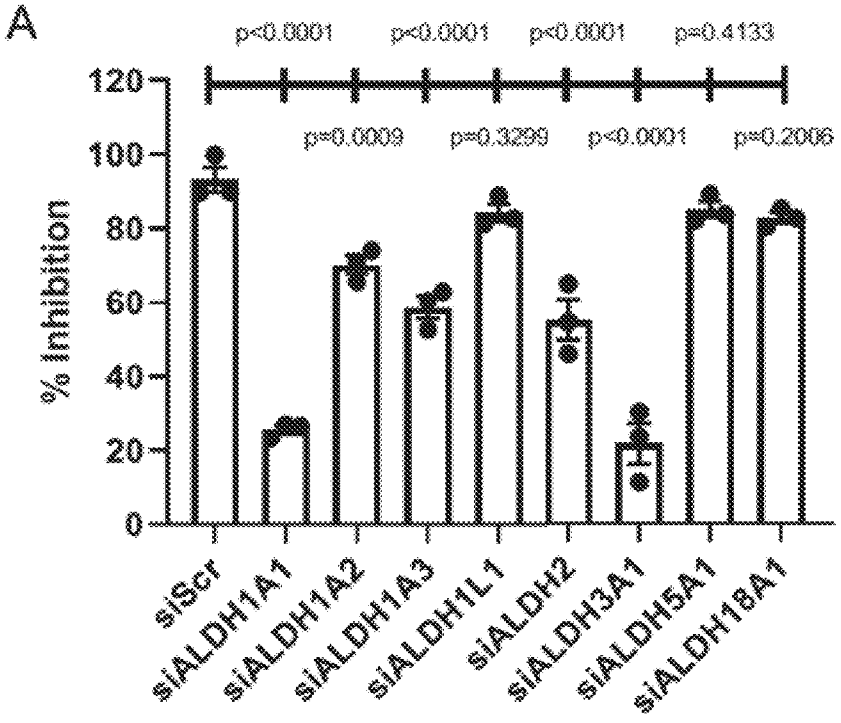
FIG. 12. Toxicity of 3(h-l). Compounds 3(h-l) were dosed daily at 5 mg/kg via i.p. injection to Swiss-Webster mice for 14 days. % change in animal weight was compared to DMSO control.
FIGS. 13A and 13B. KS100 is a multi-ALDH inhibitor. UACC 903 cells were transfected with siRNA of individual isoforms of ALDH and the effect of 5 μM of KS100 on cell survival were evaluated and compared to that of scrambled siRNA knockdown (A). Knockdown of individual siRNA were confirmed by qRT-PCR (B)
Figure 13B:
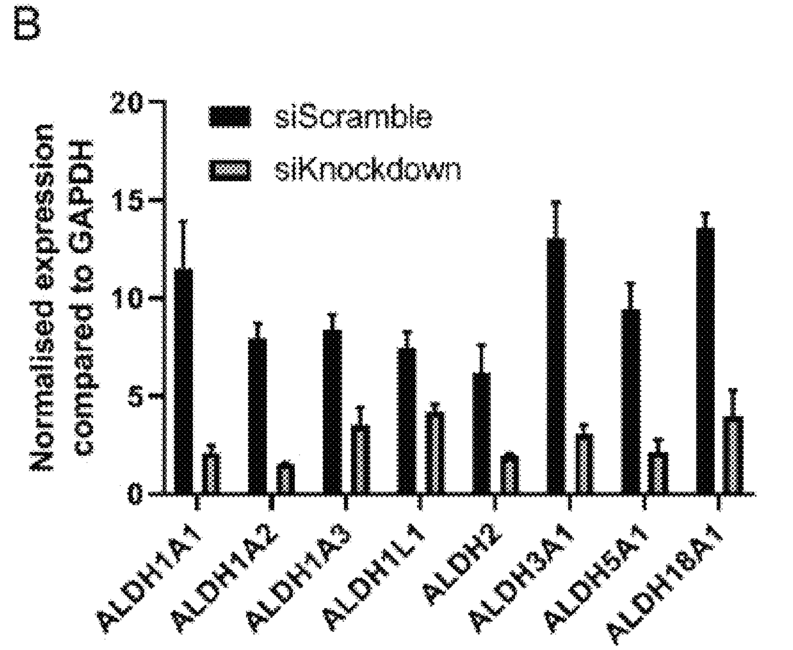
Figure 14A:
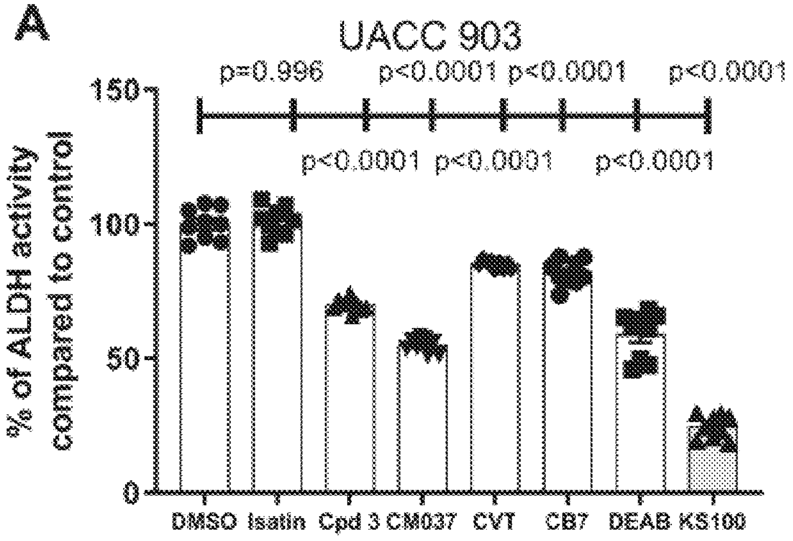
FIG. 14A-14B. KS100 reduces enzymatic ALDH activity in cell lysates. KS100 was the most effective at reducing total ALDH activity in both UACC 903 (FIG. 14A) and 1205 Lu (FIG. 14B) cell lysates.
Figure 14B:
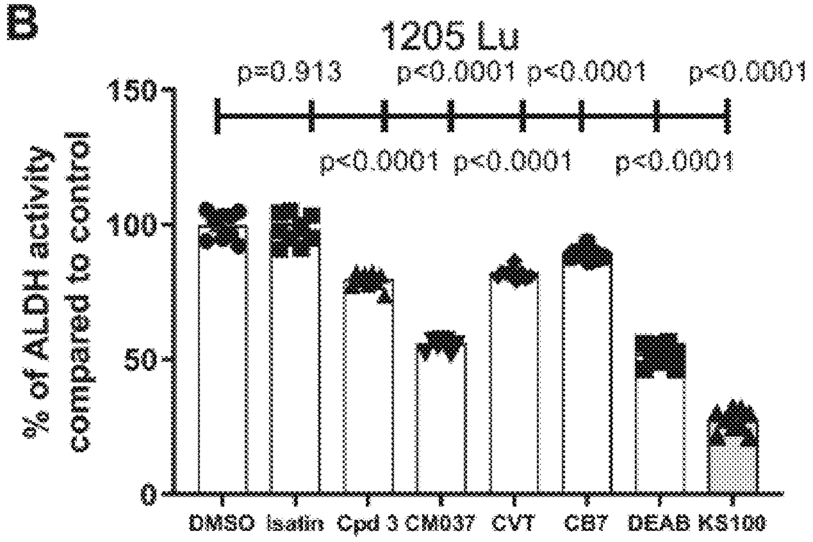
Figures 15A, 15B, 15C, 15D, 15E, 15F:
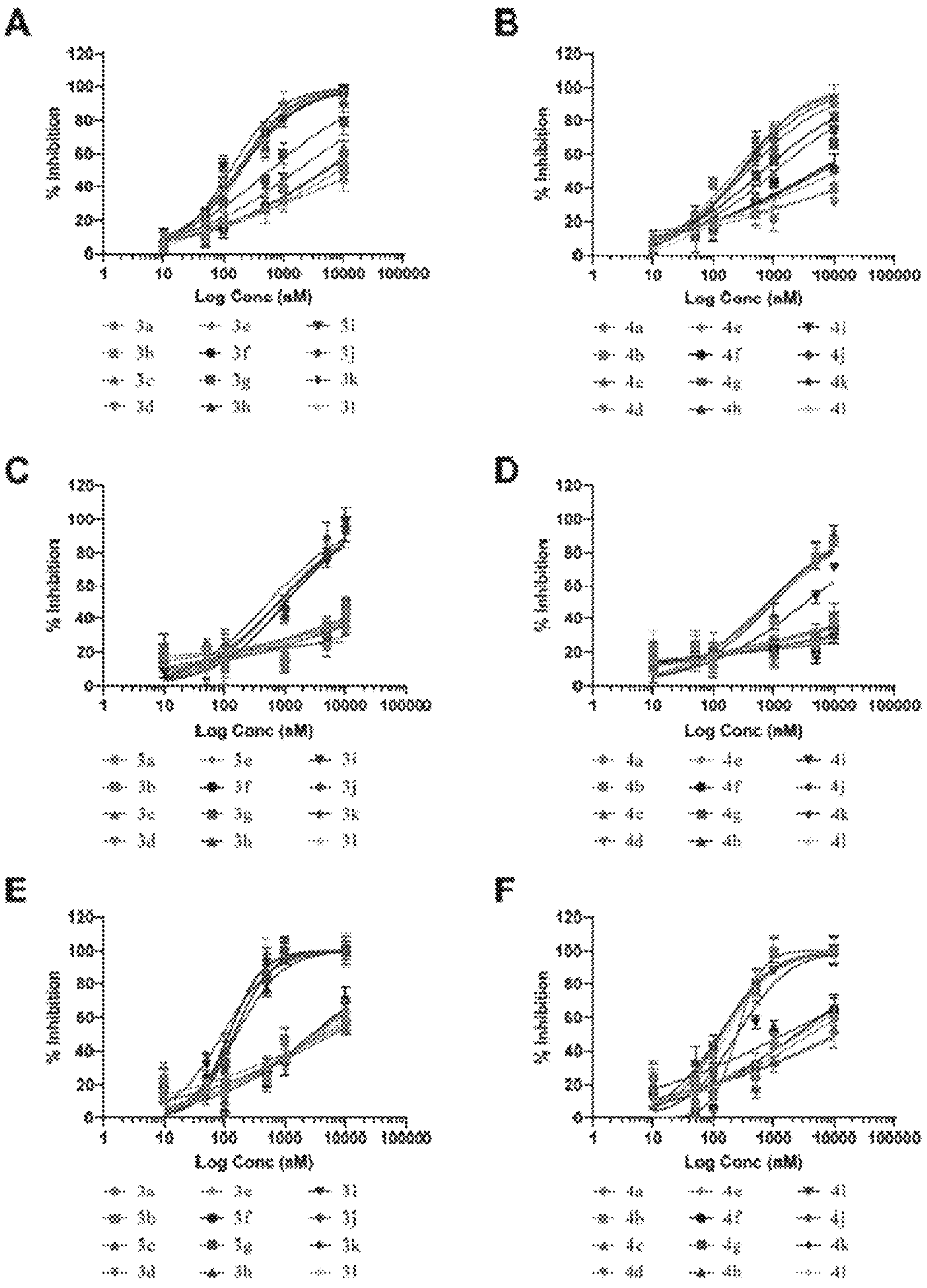
FIGS. 15A-15F. Enzyme $IC_{50}$s-Dose response curves.
Figures 16A, 16B, 16C, 16D:
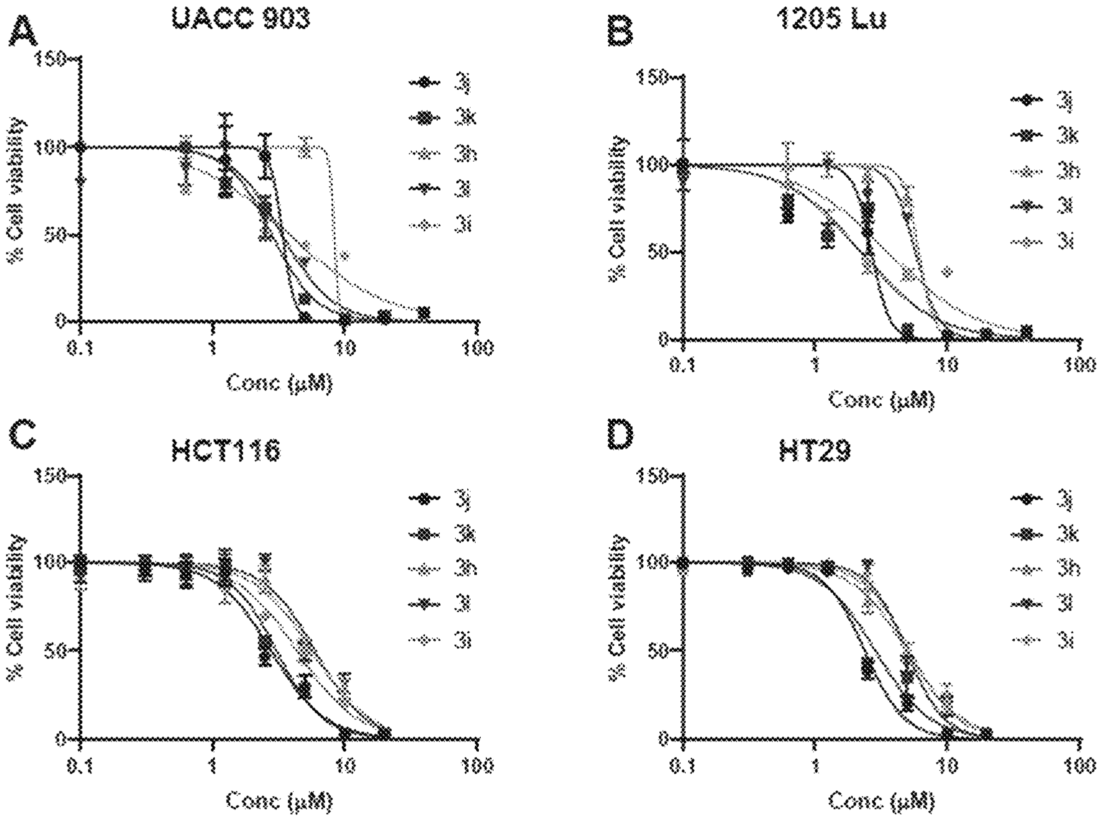
FIGS. 16A-16D. Cellular $IC_{50}$s-Dose response curves-Colon, melanoma.
Figures 17A, 17B, 17C, 17D, 17E:
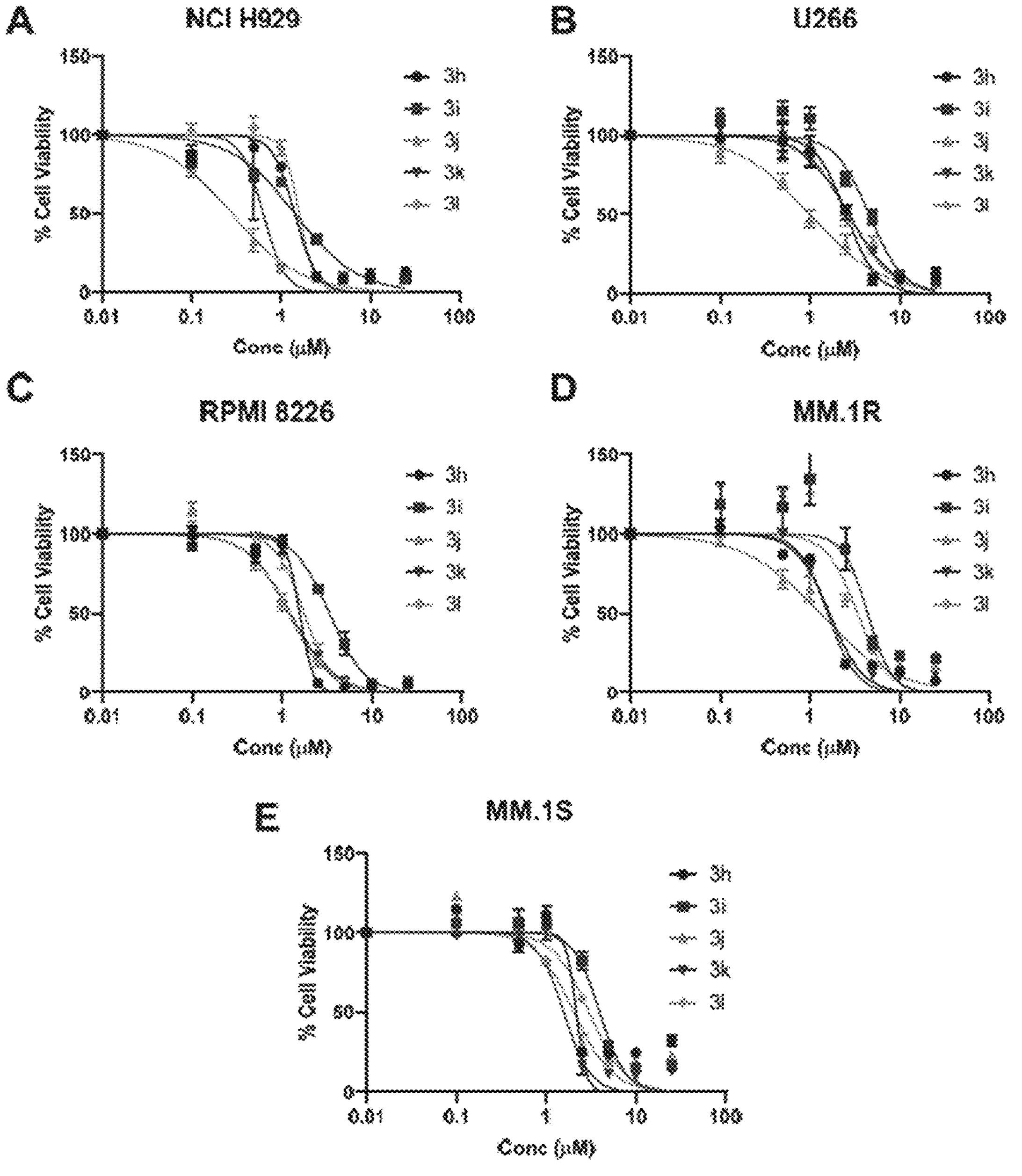
FIGS. 17A-17E. Cellular $IC_{50}$s-Dose response curves-multiple myeloma.

Flow cytometric analysis showed that 5 μM KS100 significantly increased Annexin-V positive UACC 903 and 1205 Lu cells compared to 5 μM of the other ALDH inhibitors after 24 hours (representative dot plots in FIG. 7). Specifically, KS100 increased the early apoptotic cell fraction (Annexin-$V^{+}$7-$AAD^{-}$) from 9.5% to 22.4% in UACC 903 cells (FIG. 6I) and from 12.5% to 60.4% in 1205 Lu cells (FIG. 6J). Western blot analysis of cultured UACC 903 cells following treatment with increasing concentrations (2-6 μM) of KS100 for 24 hours (FIG. 6K) showed increased apoptosis and autophagy, exemplified by elevated levels of cleaved PARP and LC3B, respectively. Collectively, these data demonstrate that KS100 significantly reduces total cellular ALDH activity to increase ROS generation, lipid peroxidation and accumulation of toxic aldehydes leading to increased apoptosis and autophagy.

Study 2

Molecular Docking Studies

A series of compounds were designed and tested for their ability to bind in the active site pockets of ALDH1A1, 2 and 3A1 using molecular docking studies. 1,4-bis(bromomethyl) benzene was selected as a linker to connect the isatin scaffold and isothiourea moieties. The protein structures of ALDH1A1, 2 and 3A1 co-crystallized with the corresponding potent, isoform-specific ALDH inhibitors CM037 (ALDH1A1), psoralen (ALDH2) and CB7 (ALDH3A1) were selected. The designed compounds were first docked into the ligand-binding pocket of ALDH1A1. Significant interactions identified between the crystal ligand, CM037, and ALDH1A1 were a π-π interaction with the W178 residue and an H-bond interaction with the Gly458 and Ser121 residues along with interactions with Cys303. Isatin did not exhibit any of these interactions with ALDH1A1; however, KS99 had a similar π-π interaction with the W178 residue and H-bond interaction with the Gly458 and Ser121 residues of ALDH1A1. Cpd 3 had interactions with W178 and S121. Importantly, compounds 3(a-l) and 4(a-l) shared similar interactions with residues in the ligand-binding pocket of ALDH1A1 compared to CM037 and KS99, indicating they could potentially be inhibitors of ALDH1A1.

Isatin

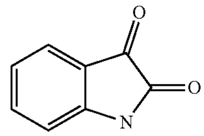

ALDH1A1 $IC_{50}$: 15.6 μM
ALDH2 $IC_{50}$: 16.9 μM
ALDH3A1 $IC_{50}$: 5.0 μM

Cpd 3

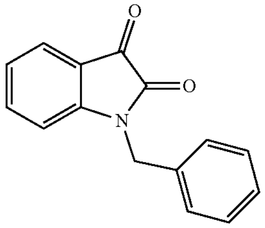

ALDH1A1 $IC_{50}$: 20 nM
ALDH2 $IC_{50}$: 80 μM
ALDH3A1 $IC_{50}$: 7.7 μM

KS99

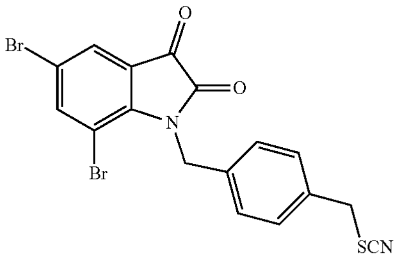

ALDH1A1 $IC_{50}$: 350 nM
ALDH2 $IC_{50}$: 1.5 μM
ALDH3A1 $IC_{50}$: 850 μM

Docking studies were similarly conducted with compounds and the ALDH2 and ALDH3A1 protein structures. π-π interactions with the F459 residue and H-bond interactions with the L269 residues occurred between ALDH2 and the crystal ligand, psoralen. Similarly, π-π interactions with the T115 residue occurred between ALDH3A1 and the crystal ligand, CB7. Importantly, compounds 3(a-l) and 4(a-l) shared similar interactions with residues in the ligand-binding pockets of ALDH2 and ALDH3A1 compared to psoralen and CB7, respectively, indicating they could be inhibitors of ALDH2 and ALDH3A1. Docking scores for 3(a-l) and 4(a-l) ranged from −7.495 to −11.938 for ALDH1A1, −6.756 to −11.205 for ALDH2 and −12.119 to −14.564 for ALDH3A1. Based on these strong docking scores, 3(a-l) and 4(a-l) were synthesized for further analysis of their ALDH enzyme inhibitory activity, anticancer efficacy and toxicity.

Chemistry

The synthesis of target compounds, substituted 2-[4-(2,3-dioxo-2,3-dihydroindol-1-ylmethyl)benzyl]isothiourea hydrobromides 3(a-l) and 2-[4-(2,3-dioxo-2,3-dihydroindol-1-ylmethyl)benzyl]isoselenourea hydrobromide analogs 4(a-l) are illustrated in Scheme 1. The key intermediates 2(a-l) were prepared in one step. Initially, unsubstituted, (5 or 7 mono substituted) and (5,7-disubstituted) isatins were reacted with 1,4-bis(bromomethyl)benzene in the presence of potassium carbonate in DMF to yield the corresponding N-(p-bromomethylbenzyl) isatins 2(a-l). These intermediates were then refluxed with thiourea in ethanol to produce the corresponding 2-[4-(2,3-dioxo-2,3-dihydroindol-1-ylmethyl)benzyl]isothiourea hydrobromides 3(a-l) and refluxed with selenourea in ethanol to yield 2-[4-(2,3-dioxo-2,3-dihydroindol-1-ylmethyl)benzyl]isoselenourea hydrobromide analogs 4(a-l) in excellent yields. The structures of all isatin derivatives were confirmed by $^{1}H$ NMR, $^{13}C$ NMR and HRMS analysis. The compound purity (≥98%) was analyzed by analytical high-performance liquid chromatography (HPLC) before proceeding for in vitro biological assays.

Scheme 1

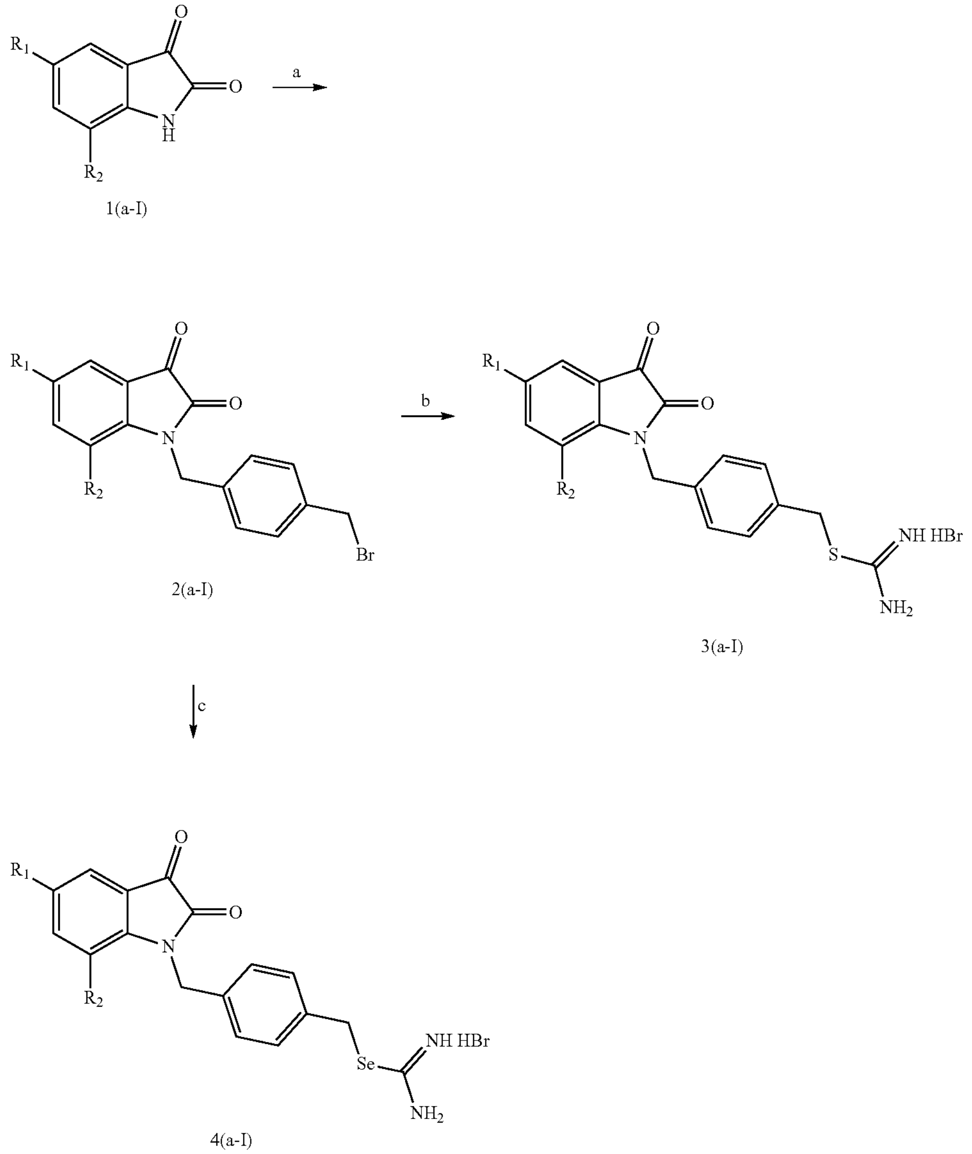

1(a-I)

2(a-I)

3(a-I)

4(a-I)

Reagents and conditions: a) $K_2CO_3$, DMF, 1,4-bis(bromomethyl)benzene; b) Thiourea, EtOH, 90° C.; c) Selenourea, EtOH, 90° C.

ALDH Isoform Inhibitory Activity

All the synthesized compounds 3(a-l) and 4(a-l) were assessed for the inhibition of ALDH1A1, ALDH2, and ALDH3A1 enzyme activity at 1-10000 nM, and the results were summarized in Table 2. The enzymes inhibition were evaluated by measuring the conversion of NADþ to NADH following the addition of isoform-specific aldehydes in the presence of 3(ael) and 4(a-l). ALDH inhibitory IC50s activity of 3(ael) and 4(ael) were 230 nM to >10,000 nM for ALDH1A1, 939 nM to >10,000 nM for ALDH2 and 193 nM to >10,000 nM for ALDH3A1. (dose response curves in FIGS. 15A-15F). 3(hel), 4b, and 4(j-l) had the most potent inhibition of ALDH1A1, ALDH2, and ALDH3A1 at the concentrations tested and were considered potent, multi-ALDH isoform inhibitors. The most potent multi-ALDH isoform inhibitor, on average of the three isoforms evaluated, was 3j, which had IC50s of 230 nM, 1542 nM, and 193 nM for ALDH1A1, ALDH2, and ALDH3A1 enzyme activity. ALDH1A1, 2 and 3A1 enzyme activity was evaluated by measuring the conversion of NAD+ to NADH following the addition of isoform-specific aldehydes in the presence of 3(a-l) and 4(a-l). The enzyme inhibitory activities of compounds 3(a-l) and 4(a-l) ranged from 23.3% to 74.7% at 500 nM for ALDH1A1, 18.3% to 88.8% at 5 μM for ALDH2 and 16.0% to 99.0% at 500 nM for ALDH3A1. 3(h-l), 4b and 4(j-l) had at least 60% inhibition of ALDH1A1, 2 and 3A1 at the concentrations tested, and were considered potent, multi-ALDH isoform inhibitors. The most potent multi-ALDH isoform inhibitor, on average, was 3j, which had 74.7% and 91.6% inhibition of ALDH1A1 and 3A1 at 500 nM and 88.8% inhibition of ALDH2 at 5 μM.

Several trends in the structure-activity relationship of compounds 3a-3l and 4a-4l were noted.

Compounds (X═S, series 3) with isothiourea moiety generally had greater multi-ALDH isoform inhibitory activity than that of corresponding isoselenourea compounds (X═Se, series 4). The lower inhibitory activity of selenium analogs may vary due to the larger size of selenium than a sulfur atom, which may interfere with the binding in the active-site pocket. For instance, 3h and 3j were more potent ALDH inhibitors than 4h and 4j, respectively. ALDH inhibitory activity of 3(a-l) and 4(a-l) depended on the halogen substitution at R1 and/or R2. Specifically, -dibromo substitutions (3j, 4j) led to the best ALDH inhibition, followed by -dichloro (3k, 4k), -fluoro, bromo (3l, 4l), trifluoromethyl (3h), -fluoro (3f, 4f) and finally unsubstituted (3a, 4a) compounds. Also, 5,7-disubstituted b compounds (3j, 3k) were more effective compared to 5-substituted (3b, 3d) or 7-substituted (3c, 3e) compounds. Further, 7-substituted compounds (3c, 3e) were more effective than 5-substituted compounds (3b, 3d). Finally, 5,7-dibromo substitutions (3j, 4j) had greater ALDH inhibitory activity compared to 5-fluoro, 7-bromo substitutions (3l, 4l). Among all the compounds, 5,7-dibromo substitutions ultimately had the best ALDH inhibitory activity, which is likely due to larger size of bromine compared to other halogens and the more hydrophobic nature of bromine, which facilitated the interaction in the hydrophobic binding pocket.

Cellular Activity

Since isothiourea compounds (series 3) were in general, more potent ALDH1A1, ALDH2 and ALDH3A1 inhibitors compared to their series 4 counterparts, only 3(h-l), the most potent inhibitors in series 3, were tested for their antiproliferative effects on cultured cancer cells. Specifically, 3(h-l) were evaluated for their ability to inhibit the proliferation of cultured melanoma cells (UACC 903 and 1205 Lu) as ALDH overexpression is important in melanoma progression (Luo Y, et al., ALDH1A isozymes are markers of human melanoma stem cells and potential therapeutic targets. *Stem Cells* 2012; 30(10):2100-13; Yue L, et al., Targeting ALDH1 to decrease tumorigenicity, growth and metastasis of human melanoma. *Melanoma Res* 2015; 25(2):138-48). The range of $IC_{50}$s against UACC 903 cells was 3 to 5.7 μM and for 1205 Lu cells was 2.1 to 5.7 μM (dose response curves in FIGS. 15A-15D), with 3j and 3k being the most effective across both cell lines. Cell killing by 3(h-l) was also specific for melanoma cells compared to normal human fibroblasts (FF2441). Specifically, 3(h-l) were 2- to 3.8-fold more selective for killing melanoma cells. Importantly, Cpd 3 and the inactive compound 3a had IC50s greater than 100 mM in all the cell lines evaluated, demonstrating the importance of substitutions on the isatin ring of the synthesized compounds.

Figure 18:
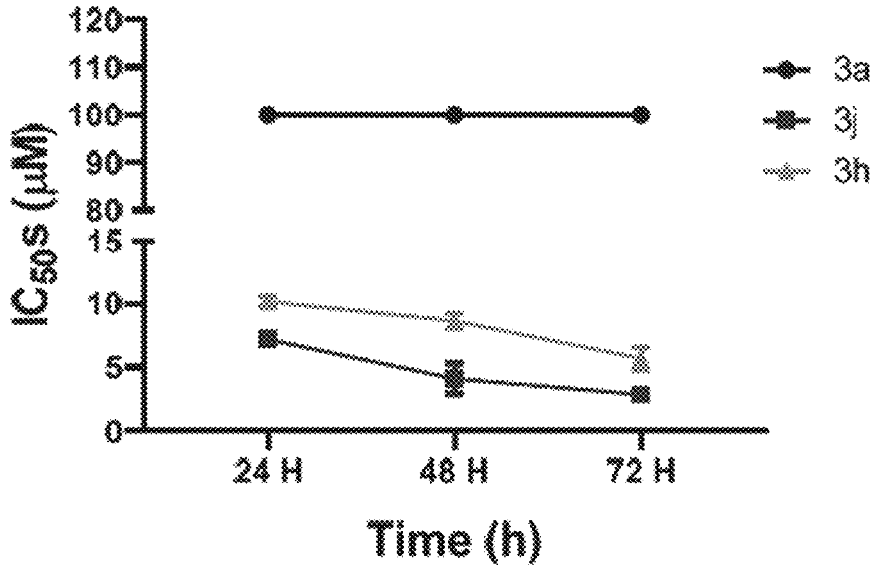
FIG. 18. $IC_{50}$ timeline for 3a, 3h and 3j in UACC 903 cells.

Subsequently, 3(h-l) were evaluated for their antiproliferative effects in other cancer types. Colon cancer cells (HCT116 and HT29) were studied as ALDH overexpression is also important in colon cancer progression (Durinikova E, et al., ALDH1A3 upregulation and spontaneous metastasis formation is associated with acquired chemoresistance in colorectal cancer cells. BMC Cancer 2018; 18(1):848). Average $IC_{50}$s for each compound across both cell lines were 5.3 μM for 3h, 5.15 μM for 3i, 2.7 μM for 3j, 2.9 μM for 3k and 5.1 μM for 3l (dose response curves in FIGS. 16A-16D). Compounds 3j and 3k were most effective in inhibiting the colon cancer cell survival likely due to strong inhibition of ALDH1A1 and ALDH3A1. Multiple myeloma cells were also examined, as ALDH1A1 overexpression has been associated with stemness, therapy resistance and poor outcomes in this cancer type (Marcato P, et al., Aldehyde dehydrogenase: its role as a cancer stem cell marker comes down to the specific isoform. *Cell Cycle* 2011; 10(9):1378-84; Matsui W, et al., Clonogenic multiple myeloma progenitors, stem cell properties, and drug resistance. *Cancer research* 2008; 68(1):190-7; Deng S, et al., Distinct expression levels and patterns of stem cell marker, aldehyde dehydrogenase isoform 1 (ALDH1), in human epithelial cancers. PloS one 2010; 5(4):e10277; Ginestier C, et al., ALDH1 is a marker of normal and malignant human mammary stem cells and a predictor of poor clinical outcome. Cell stem cell 2007; 1(5):555-67; Yang Y, et al., NEK2 mediates ALDH1A1-dependent drug resistance in multiple myeloma. *Oncotarget* 2014; 5(23):11986-97). Average $IC_{50}$s for 3(h-l) across all multiple myeloma cell lines tested (NCIH929, U266, RPMI8226, MM.1R) were 1.9 μM for 3h, 3.8 μM for 3i, 1 μM for 3j, 1.6 μM for 3k and 2.4 μM for 3l (dose response curves in FIGS. 17A-17E). Compounds 3h, 3j, and 3k showed more potent growth inhibition of multiple myeloma cells when compared to melanoma and colon cancer cells, demonstrating the greater effectiveness of these compounds even in hematological malignancies. Additionally, these compounds displayed better $IC_{50}$s at killing melanoma cell with time, and $IC_{50}$s of 3j were 7.2 μM at 24 h compared to 4.1 μM at 48 h and 3.7 μM at 72 h (FIG. 18). Thus, 3(h-l) were specific to cancer cells and displayed antiproliferative activity against cultured melanoma, colon cancer and multiple myeloma cells, indicating the potential for these compounds to be translated into the clinic. Moreover, 3(h-l) displayed chemical properties predictive of good solubility, absorption, metabolism, and excretion, indicating the drug-like properties of these compounds. All these compounds adhered to Lipinski's rule of five for drug-like compounds.

Toxicity Studies

Figure 19:
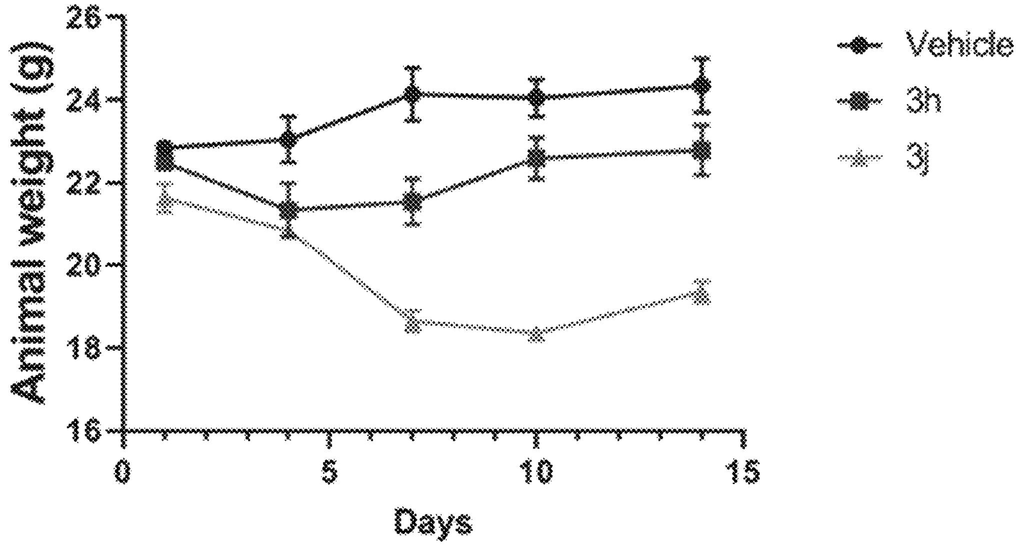
FIG. 19. Toxicity timeline for compounds 3h and 3j.

Since compounds 3(h-l) were identified to be potent, multi-ALDH isoform inhibitors with antiproliferative activity in multiple cancer types, the toxicity of these compounds was evaluated for translatability to the clinic. Specially, Swiss-Webster mice were treated with 5 mg/kg/day of 3(h-l) i.p. for 14 days and animal weight was compared to DMSO. Compounds 3(i-l) led to significant weight loss (10-15% body weight) after 14 days of treatment, while 3h led to no significant weight loss (toxicity timeline shown in FIG. 19). Thus, 3h was identified to be the least toxic agent, which may be due to lesser ALDH inhibitory activity when compared to compounds 3(i-l). Toxicity of 3(i-l) could be mitigated using controlled release formulations, such as nanoliposomes.

ROS and Lipid Peroxidation Activity and Toxic Aldehyde Accumulation

Accumulation of toxic aldehydes (e.g., 4-HNE, 4-HHE, MDA, acrolein) secondary to ALDH inhibition can lead to protein adduct formation, increased ROS levels and lipid peroxidation, ultimately causing cell damage and apoptosis (Rodriguez-Zavala J S, et al., Role of Aldehyde Dehydrogenases in Physiopathological Processes. *Chem Res Toxicol* 2019; Grune T. Protein Oxidation Products as Biomarkers. *Free Radic Biol Med* 2014; 75 Suppl 1:S7; Shoeb M, et al., 4-Hydroxynonenal in the pathogenesis and progression of human diseases. *Curr Med Chem* 2014; 21(2):230-7). Thus, to evaluate the mechanism by which ALDH inhibitors killed the cultured cancer cells, a ROS assay was performed using DCFDA dye (Rao P C, et al., Coptisine-induced cell cycle arrest at G2/M phase and reactive oxygen species-dependent mitochondria-mediated apoptosis in non-small-cell lung cancer A549 cells. *Tumour Biol* 2017; 39(3): 1010428317694565). Specifically, UACC 903 and 1205 Lu cells were treated with 5 μM of 3(h-l) for 24 hours and ROS activity in treated cells was compared to DMSO. As shown in FIGS. 8A-8B, 3h and 3j significantly increased ROS levels in both colon cell lines, indicating elevated ROS levels likely contribute to the antiproliferative effects. Additionally, compound 3a, an inactive derivative, did not significantly increase the ROS activity in any of the cell lines evaluated. Importantly, the ROS-inducing activity of compounds 3h and 3j was abrogated by the addition of N-Acetyl Cysteine (NAC), a scavenger of ROS activity in cells, indicating that the compounds were affecting the ROS-pathway.

To evaluate if 3h and 3j led to increased lipid peroxidation and toxic aldehyde accumulation, a lipid peroxidation assay was performed using a TBARS assay kit (Yagi K. Simple assay for the level of total lipid peroxides in serum or plasma. *Methods Mol Biol* 1998; 108:101-6). Specifically, UACC 903 and 1205 Lu cells were treated with 5 μM of 3h and 3j for 24 hours, and lipid peroxidation activity and toxic aldehyde accumulation in treated cells were compared to DMSO. As shown in FIGS. 8C-8D, 3h and 3j significantly increased lipid peroxidation and toxic aldehyde accumulation in both melanoma cell lines, indicating increased lipid peroxidation and toxic aldehyde accumulation in HCT116 colon cancer cell line, likely contribute to the antiproliferative effects. Additionally, 3a was ineffective in increasing the lipid peroxidation; while the addition of NAC abrogated the effects of 3h and 3j, indicating the importance of the ROS pathway in the accumulation of toxic aldehydes by these ALDH inhibitors.

Figures 20A, 20B:
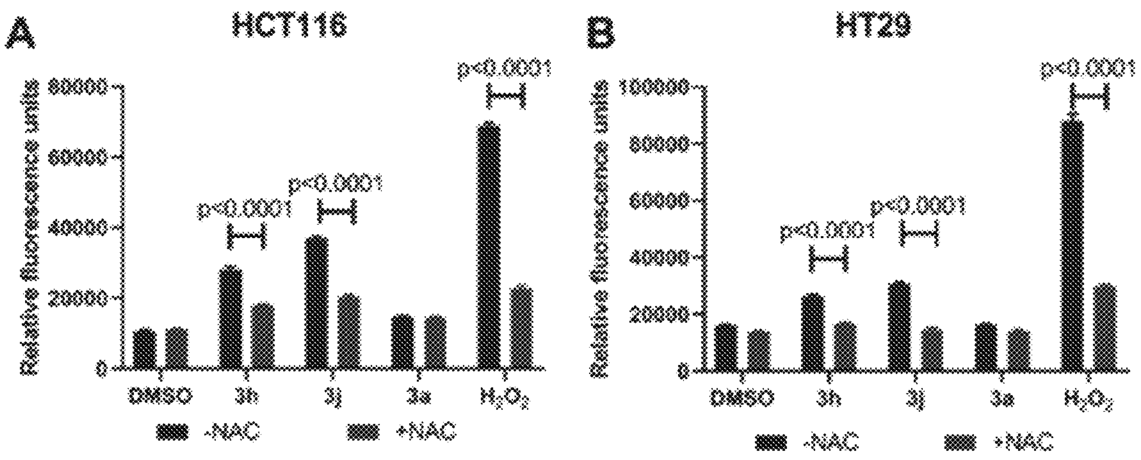
FIGS. 20A-20F. ROS, lipid peroxidation activity and toxic aldehyde accumulation. HCT116 (FIG. 20A) and HT29 (FIG. 20B) cells were treated with 5 mM of 3a, 3h, or 3j for 24 h with or without NAC (10 mM). ROS levels were measured using DCFDA dye and compared to DMSO control. Malondialdehyde (MDA) levels were measured in colon cancer cell line HCT116 using thiobarbituric acid and compared to DMSO control (FIG. 20C). Cell survival assay was performed by MTS assay (FIG. 30D), apoptosis by Annexin-V/7-AAD (FIG. 20E) and cell cycle by propidium iodide staining in colon cancer cell line HCT116 (FIG. 20F).
Figure 20C:
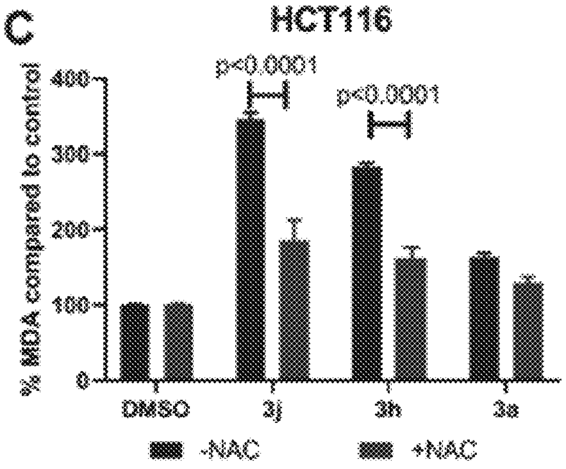
Figures 20D, 20E:
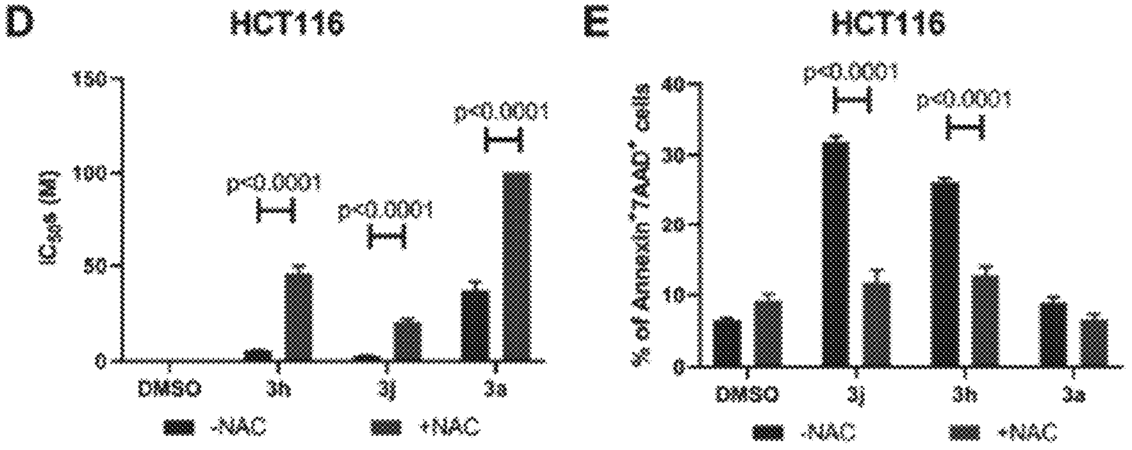
Figure 20F:
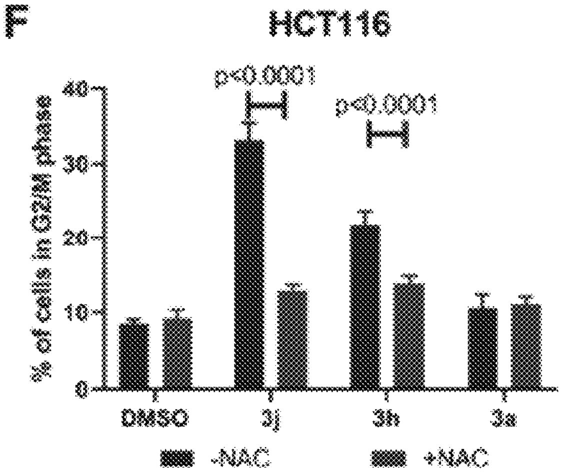

Further, the effect of the addition of NAC on the antiproliferative and apoptotic activity of ALDH inhibitors was also evaluated. Addition of NAC increased the cell killing $IC_{50}$s of 3h and 3j in colon cancer cell line, HCT116 by 6-fold, and 8-fold, respectively (FIG. 20D). Similar activity was observed in apoptosis and cell cycle assays where NAC abrogated the activity of the potent ALDH inhibitors. When HCT116 colon cancer cells were treated with 3h and 3j at 5 mM for 24 h, the percentage of cells which are both Annexin-V and 7-AAD positive were significantly higher than the DMSO control-treated cells or inactive compound 3a treated cells (FIG. 20E). When NAC was added to these compounds, there was no increase in apoptotic cells compared to DMSO treated cells. Similarly, compounds 3j and 3h caused a G2/M arrest in the cell cycle of the colon cancer cell line HCT116, which was reversed by addition of NAC (FIG. 20F). These data suggest that the potent ALDH inhibitors induce ROS activity, lipid peroxidation and accumulation of toxic aldehydes to inhibit cell survival and induce apoptosis through the modulation of the ROS pathway.

Isatin was purchased from Sigma-Aldrich (Sigma-Aldrich, St. Louis, MO, USA), 5,7-dibromo isatin was synthesized using previously reported methods (Krishnegowda G, et al., Synthesis and biological evaluation of a novel class of isatin analogs as dual inhibitors of tubulin polymerization and Akt pathway. *Bioorg Med Chem* 2011; 19(20):6006-14). All other chemicals and solvents were purchased from the major vendors. Anhydrous solvents were used as received. Reactions were carried out using dried glassware and under an atmosphere of nitrogen. Reaction progress was monitored with analytical thin-layer chromatography (TLC) on aluminum-backed precoated silica gel 60 F254 plates (E. Merck). The N-alkylisatins were highly colored and would usually be seen on a TLC plate; colorless compounds were detected using UV light and/or iodine vapor. Column chromatography was carried out using silica gel 60 (230-400 mesh, E. Merck) with the solvent system indicated in the individual procedures. All solvent ratios are quoted as vol/vol. NMR spectra were recorded using a Bruker Avance 500 MHz spectrometer. Chemical shifts (δ) were reported in parts per million downfield from the internal standard. The signals are quoted as s (singlet), d (doublet), t (triplet), m (multiplet), dd (doublet of doublet), ddd (doublet of doublets of doublets), dt (doublet of triplets). Spectra are referenced to the residual solvent peak of the solvent stated in the individual procedure. High-resolution mass spectra (HRMS) were determined in 5600 (QTOF) TripleTOF using a Duospray™ ion source (Sciex, Framingham, MA). The capillary voltage was set at 5.5 kV in positive ion mode with a declustering potential of 80V. The mass spectrometer was scanned from 50 to 1000 m/z in operating mode with a 250 ms scan from 50 to 1000 m/z. Melting points were determined on a Fischer-Johns melting point apparatus and are uncorrected. The purity of the compound was established by HPLC using an HP-Agilent 1200 HPLC system on a C18 column, and all the compounds had a purity of >95% unless mentioned.

General Procedure for the Synthesis of Compounds 2(a-l)

Initially, mono (5 or 7) or di-substituted (5,7) or unsubstituted isatin 1(a-l) (10 mmol) was taken up in anhydrous DMF (30 mL) and cooled on ice with stirring. Solid $K_2CO_3$ (11 mmol) was added in one portion, and the dark-colored suspension was brought to room temperature and stirred for a further 1 h. 1,4-bis(bromomethyl)benzene (40 mmol) was added slowly with constant stirring until the mono or di-substituted isatin starting material had been consumed (TLC). The reaction mixture was poured into cold water and extracted with ethyl acetate. The ethyl acetate layer was washed with water, brine and dried over $MgSO_4$. The solvent was removed, and the crude product was purified by silica gel column chromatography using (hexanes/EtOAc, 80:20) as eluent to yield the key intermediates (—N-(p-bromomethyl benzyl)isatins 2(a-l) (yield 75-80%) as orange-red crystals.

General Procedure for the Synthesis of Compounds 3(a-l)

To each unsubstituted, mono and di-substituted (—N-(p-bromomethyl benzyl)isatins 2(a-l) (1.02 mmol), thiourea (1.02 mmol) and ethanol (25 ml) was added and heated to reflux until the starting material had been disappeared (TLC). The solvent was removed under vacuum. The crude product was washed with ethyl acetate to remove unreacted (—N-(p-bromomethyl benzyl)isatins. The products 3(a-l) were recrystallized by ethanol-ethyl acetate (1:9) with good yields.

General Procedure for the Synthesis of Compounds 4(a-l)

To each unsubstituted, mono and di-substituted (—N-(p-bromomethyl benzyl)isatins 2(a-l) (1.02 mmol), selenourea (1.02 mmol) and ethanol (25 ml) was added and heated to reflux until the starting material had been disappeared (TLC). The solvent was removed under vacuum. The crude product was washed with ethyl acetate to remove unreacted (—N-(p-bromomethyl benzyl)isatins. The products 4(a-l) were recrystallized by ethanol-ethyl acetate (1:9) with good yields.

2-[4-(2,3-Dioxo-2,3-dihydroindol-1-ylmethyl)benzyl]isothiourea hydrobromide (3a) (KS104).

Yellow solid, Yield: 83%; mp: 208-210° C.; $^1$H NMR (500 MHz, DMSO-$d_6$): δ 9.18 (s, 2H), 8.98 (s, 2H), 7.61-7.57 (m, 2H), 7.46-7.38 (m, 4H), 7.13 (dt, J=0.6, 7.5 Hz, 1H), 6.98 (dd, J=0.5, 8.2 Hz, 1H), 4.92 (s, 2H), 4.47 (s, 2H). $^{13}$C NMR (125 MHz, DMSO-$d_6$): δ 183.5, 169.5, 158.8, 150.8, 138.5, 135.9, 134.8, 129.8, 128.3, 125.0, 123.9, 118.3, 111.5, 43.1, 34.4. MS (ESI) m/z 326 [M+H]; HRMS (ESI) m/z for $C_{17}H_{15}N_3O_2S$ calculated 326.0885, found m/z: 326.0963.

2-[4-(5-Bromo-2,3-dioxo-2,3-dihydroindol-1-ylmethyl)benzyl]isothiourea hydrobromide (3b) (KS108).

Orange solid, Yield: 75%; mp: 217-219° C.; $^1$H NMR (500 MHz, DMSO-$d_6$): δ 9.15-8.96 (m, 4H), 7.78-7.75 (m, 2H), 7.46-7.37 (m, 4H), 6.93 (dd, J=0.5, 8.2 Hz, 1H), 4.91 (s, 2H), 4.46 (s, 2H). $^{13}$C NMR (125 MHz, DMSO-$d_6$): δ 182.3, 169.5, 158.5, 149.6, 140.1, 135.6, 134.8, 129.7, 128.2, 127.2, 120.1, 115.6, 113.6, 43.1, 34.4. MS (ESI) m/z 404 [M+H]; HR-MS (ESI) m/z for $C_{17}H_{14}BrN_3O_2S$ calculated 403.9990, found m/z: 404.0075.

2-[4-(7-Bromo-2,3-dioxo-2,3-dihydroindol-1-ylmethyl)benzyl]isothiourea hydrobromide (3c) (KS110).

Yellow solid, Yield: 78%; mp: 206-208° C.; $^1$H NMR (500 MHz, DMSO-$d_6$): δ 9.18 (s, 2H), 8.99 (s, 2H), 7.76 (dd, J=1.2, 8.1 Hz, 1H), 7.65 (dd, J=1.2, 7.3 Hz, 1H), 7.39 (s, 4H), 7.10 (dd, J=7.4, 8.1 Hz, 1H), 5.26 (s, 2H), 4.48 (s, 2H). $^{13}$C NMR (125 MHz, DMSO-$d_6$): δ 182.3, 169.5, 159.9, 147.5, 143.3, 137.5, 134.1, 129.6, 127.2, 125.6, 124.5, 122.1, 103.6, 44.4, 34.5. MS (ESI) m/z 404 [M+H]; HRMS (ESI) m/z for $C_{17}H_{14}BrN_3O_2S$ calculated 403.9990, found m/z: 404.0091.

2-[4-(5-Chloro-2,3-dioxo-2,3-dihydroindol-1-ylmethyl)benzyl]isothiourea hydrobromide (3d) (KS112).

Orange solid, Yield: 77%; mp: 226-228° C.; $^1$H NMR (500 MHz, DMSO-$d_6$): δ 9.17 (s, 2H), 8.97 (s, 2H), 7.65-7.63 (m, 2H), 7.42 (dd, J=8.2, 26.3 Hz, 4H), 6.99 (dd, J=1.6, 7.4 Hz, 1H), 4.92 (s, 2H), 4.48 (s, 2H). $^{13}$C NMR (125 MHz, DMSO-$d_6$): δ 182.4, 169.5, 158.6, 149.2, 137.3, 135.6, 134.8, 129.7, 128.3, 128.1, 124.5, 119.7, 113.2, 43.2, 34.4. MS (ESI) m/z 360 [M+H]; HRMS (ESI) m/z for $C_{17}H_{14}ClN_3O_2S$ calculated 360.0495, found m/z: 360.0570.

2-[4-(7-Chloro-2,3-dioxo-2,3-dihydroindol-1-ylmethyl)benzyl]isothiourea hydrobromide (3e) (KS114).

Orange solid, Yield: 73%; mp: 225-227° C.; $^1$H NMR (500 MHz, DMSO-$d_6$): δ 9.18 (s, 2H), 9.03 (s, 2H), 7.62 (d, J=2.4 Hz, 1H), 7.61 (dd, J=1.1, 4.4 Hz, 1H), 7.40 (s, 4H), 7.17 (t, J=7.7 Hz, 1H), 5.22 (s, 2H), 4.51 (s, 2H). $^{13}$C NMR (125 MHz, DMSO-$d_6$): δ 182.3, 169.5, 159.8, 146.0, 139.9, 137.5, 134.2, 129.6, 127.2, 125.3, 124.1, 121.8, 116.2, 44.8, 34.5. MS (ESI) m/z 360 [M+H]; HRMS (ESI) m/z for $C_{17}H_{14}ClN_3O_2S$ calculated 360.0495, found m/z: 360.0584.

2-[4-(5-Fluoro-2,3-dioxo-2,3-dihydroindol-1-ylmethyl)benzyl]isothiourea hydrobromide (3f) (KS116).

Orange solid, Yield: 75%; mp: 208-210° C.; $^1$H NMR (500 MHz, DMSO-$d_6$): δ 9.17 (s, 2H), 9.03 (s, 2H), 7.50 (dd, J=2.4, 7.0 Hz, 1H), 7.47 (dd, J=2.9, 6.1 Hz, 1H), 7.46 (d, J=8.2 Hz, 2H), 7.41 (d, J=8.4 Hz, 2H), 7.00 (dd, J=3.8, 8.6 Hz, 1H), 4.92 (s, 2H), 4.51 (s, 2H). $^{13}$C NMR (125 MHz, DMSO-$d_6$): δ 182.9, 169.5, 159.0, 158.9, 147.0, 135.7, 134.8, 129.8, 128.3, 124.3, 119.2, 112.9, 112.0, 43.2, 34.4. MS (ESI) m/z 344 [M+H]; HRMS (ESI) m/z for $C_{17}H_{14}FN_3O_2S$ calculated 344.0791, found m/z: 344.0883.

2-[4-(7-Fluoro-2,3-dioxo-2,3-dihydroindol-1-ylmethyl)benzyl]isothiourea hydrobromide (3g) (KS118).

Orange solid, Yield: 71%; mp: 210-212° C.; $^1$H NMR (500 MHz, DMSO-$d_6$): δ 9.20 (s, 2H), 9.06 (s, 2H), 7.52 (dd, J=8.6, 11.6 Hz, 1H), 7.48 (d, J=7.3 Hz, 1H), 7.41 (s, 4H), 7.16 (ddd, J=7.9, 7.9, 3.8 Hz, 1H), 4.97 (s, 2H), 4.51 (s, 2H). $^{13}$C NMR (125 MHz, DMSO-$d_6$): δ 182.3, 169.5, 158.9, 147.7, 136.8, 136.5, 134.6, 129.7, 127.7, 126.2, 125.1, 121.5, 121.3, 45.3, 34.4. MS (ESI) m/z 344 [M+H]; HRMS (ESI) m/z for $C_{17}H_{14}FN_3O_2S$ calculated 344.0791, found m/z: 344.0882.

2-[4-(2,3-Dioxo-5-trifluoromethyl-2,3-dihydroindol-1-ylmethyl)benzyl]isothiourea hydrobromide (3h) (KS106).

Yellow solid, Yield: 76%; mp: 225-227° C.; $^1$H NMR (500 MHz, DMSO-$d_6$): $^1$H NMR (500 MHz, DMSO) δ 9.17 (s, 2H), 9.00 (s, 2H), 7.96 (dd, J=1.3, 8.4 Hz, 1H), 7.89 (d, J=1.7 Hz, 1H), 7.49-7.39 (m, 4H), 7.15 (d, J=8.4 Hz, 1H), 4.98 (s, 2H), 4.48 (s, 2H). $^{13}$C NMR (151 MHz, DMSO-$d_6$): δ 182.0, 169.5, 159.0, 153.4, 135.5, 134.9, 134.9, 129.7, 128.3, 124.4, 124.2, 121.5, 118.9, 112.0, 43.3, 34.4. MS (ESI) m/z 394 [M+H]; HRMS (ESI) m/z for $C_{18}H_{14}F_3N_3O_2S$ calculated 394.0759, found m/z: 394.0838.

2-[4-(2,3-Dioxo-7-trifluoromethyl-2,3-dihydroindol-1-ylmethyl)benzyl]isothiourea hydrobromide (3i) (KS122).

Yellow solid, Yield: 70%; mp: 216-218° C.; $^1$H NMR (600 MHz, DMSO-$d_6$): $^1$H NMR (600 MHz, DMSO) δ 9.23 (s, 2H), 9.05 (s, 2H), 7.95 (d, J=7.6, Hz, 1H), 7.94 (dd, J=1.4, 7.2 Hz, 1H), 7.39-7.33 (m, 5H), 5.03 (s, 2H), 4.49 (s, 2H). $^{13}$C NMR (150 MHz, DMSO-$d_6$): δ 181.4, 169.5, 160.5, 148.4, 136.5, 135.0, 133.8, 129.4, 129.0, 126.5, 123.9, 123.3, 121.7, 112.8, 46.3, 34.4. MS (ESI) m/z 394 [M+H]; HRMS (ESI) m/z for $C_{18}H_{14}F_3N_3O_2S$ calculated 394.0759, found m/z: 394.0852.

2-[4-(5, 7-Dibromo-2, 3-dioxo-2, 3-dihydroindol-1-ylmethyl)benzyl]isothiourea hydrobromide (3j) (KS100).

Orange solid, Yield: 84%; mp: 196-198° C.; $^1$H NMR (500 MHz, DMSO-$d_6$): δ 9.17 (s, 2H), 8.98 (s, 2H), 8.01 (d, J=2.0 Hz, 1H), 7.82 (d, J=1.9 Hz, 1H), 7.42-7.36 (m, 4H), 5.25 (s, 2H), 4.47 (s, 2H). $^{13}$C NMR (125 MHz, DMSO-$d_6$): δ 181.1, 169.48, 159.6, 146.7, 143.8, 137.4, 134.1, 129.6, 127.2, 126.8, 123.3, 116.2, 104.7, 44.5, 34.5; MS (ESI) m/z 481 [M+H]; HRMS (ESI) m/z for $C_{17}H_{13}Br_2N_3O_2S$ calculated 481.9173, found m/z: 481.9164.

2-[4-(5, 7-Dichloro-2,3-dioxo-2,3-dihydroindol-1-ylmethyl) benzyl]isothiourea hydrobromide (3k) (KS102).

Orange solid, Yield: 81%; mp: 203-205° C.; $^1$H NMR (500 MHz, DMSO-$d_6$): δ 9.22 (s, 2H), 9.04 (s, 2H), 7.78 (d, J=2.1 Hz, 1H), 7.70 (d, J=2.1 Hz, 1H), 7.43-7.37 (m, 4H), 5.19 (s, 2H), 4.49 (s, 2H). $^{13}$C NMR (125 MHz, DMSO-$d_6$): δ 181.1, 169.5, 159.6, 144.8, 138.0, 137.4, 134.2, 129.6, 128.5, 127.1, 123.7, 122.7, 117.0, 44.8, 34.4. MS (ESI) m/z 394 [M+H]; HRMS (ESI) m/z for $C_{17}H_{13}C_{12}N_3O_2S$ calculated 394.0106, found m/z: 394.0187.

2-[4-(7-Bromo-5-fluoro-2,3-dioxo-2,3-dihydroindol-1-ylmethyl)benzyl]isothiourea hydrobromide (3l) (KS120).

Orange solid, Yield: 67%; mp: 216-218° C.; $^1$H NMR (500 MHz, DMSO-$d_6$): δ 9.25 (s, 2H), 9.14 (s, 2H), 7.79 (dd, J=2.7, 8.8 Hz, 1H), 7.63 (dd, J=2.7, 6.3 Hz, 1H), 7.37 (s, 4H), 5.23 (s, 2H), 4.50 (s, 2H). $^{13}$C NMR (125 MHz, DMSO-$d_6$): δ 181.6, 166.6, 159.3, 158.7, 144.1, 137.0, 136.1, 129.5, 128.8, 127.1, 122.6, 112.0, 103.5, 44.4, 30.5. MS (ESI) m/z 421 [M+H]; HRMS (ESI) m/z for $C_{17}H_{13}BrFN_3O_2S$ calculated 421.9895, found m/z: 421.9991.

2-[4-(2,3-Dioxo-2,3-dihydroindol-1-ylmethyl)benzyl]isoselenourea hydrobromide (4a) (KS105).

Yellow solid, Yield: 77%; mp: 216-218° C.; $^1$H NMR (500 MHz, DMSO-$d_6$): δ 9.25 (s, 2H), 9.12 (s, 2H), 7.61-7.57 (m, 2H), 7.43-7.37 (m, 4H), 7.13 (ddd, J=7.5, 7.5, 0.7 Hz, 1H), 6.99 (dd, J=0.6, 8.4 Hz, 1H), 4.90 (s, 2H), 4.50 (s, 2H). $^{13}$C NMR (125 MHz, DMSO-$d_6$): δ 183.5, 166.7, 158.8, 150.8, 138.5, 136.8, 135.5, 129.8, 128.2, 125.0, 123.9, 118.2, 111.5, 43.1, 30.4. MS (ESI) m/z 374 [M+H]; HRMS (ESI) m/z for $C_{17}H_{15}N_3O_2Se$ calculated 374.0329, found m/z: 374.0414.

2-[4-(5-Bromo-2,3-dioxo-2,3-dihydroindol-1-ylmethyl) benzyl]isoselenourea hydrobromide (4b) (KS109).

Orange solid, Yield: 70%; mp: 208-210° C.; $^1$H NMR (500 MHz, DMSO-$d_6$): δ 9.24 (s, 2H), 9.15 (s, 2H), 7.78-7.74 (m, 2H), 7.43-7.36 (m, 4H), 6.93 (d, J=8.3 Hz, 1H), 4.90 (s, 2H), 4.50 (s, 2H). $^{13}$C NMR (125 MHz, DMSO-$d_6$): δ 182.3, 166.7, 158.5, 149.6, 140.1, 136.8, 135.2, 129.7, 128.2, 127.2, 120.1, 115.6, 113.6, 43.2, 30.4. MS (ESI) m/z 451 [M+H]; HRMS (ESI) m/z for $C_{17}H_{14}BrN_3O_2Se$ calculated 451.9435, found m/z: 451.9550.

2-[4-(7-Bromo-2,3-dioxo-2,3-dihydroindol-1-ylmethyl) benzyl]isoselenourea hydrobromide (4c) (KS111).

Orange solid, Yield: 72%; mp: 202-204° C.; $^1$H NMR (500 MHz, DMSO-$d_6$): δ 9.24 (s, 2H), 9.12 (s, 2H), 7.77 (dd, J=1.2, 8.1 Hz, 1H), 7.65 (dd, J=1.2, 7.3 Hz, 1H), 7.36 (s, 4H), 7.10 (dd, J=7.3, 8.1 Hz, 1H), 5.25 (s, 2H), 4.51 (s, 2H). $^{13}$C NMR (125 MHz, DMSO): δ 182.3, 166.7, 159.9, 147.5, 143.3, 137.1, 136.1, 129.6, 127.1, 125.6, 124.5, 122.0, 103.6, 44.4, 30.5. MS (ESI) m/z 451 [M+H]; HRMS (ESI) m/z for $C_{17}H_{14}BrN_3O_2Se$ calculated 451.9435, found m/z: 451.9543.

2-[4-(5-Chloro-2,3-dioxo-2,3-dihydroindol-1-ylmethyl) benzyl]isoselenourea hydrobromide (4d) (KS113).

Orange solid, Yield: 70%; mp: 216-218° C.; $^1$H NMR (500 MHz, DMSO-$d_6$): δ 9.24 (s, 2H), 9.15 (s, 2H), 7.65-7.63 (m, 2H), 7.43-7.36 (m, 4H), 6.99 (dd, J=1.8, 7.3 Hz, 1H), 4.91 (s, 2H), 4.50 (s, 2H). $^{13}$C NMR (125 MHz, DMSO-$d_6$): δ 182.4, 166.7, 158.6, 149.3, 137.3, 136.9, 135.2, 129.7, 128.2, 128.1, 124.5, 119.7, 113.2, 43.2, 30.4. MS (ESI) m/z 407 [M+H]; HRMS (ESI) m/z for $C_{17}H_{14}ClN_3O_2Se$ calculated 407.9940, found m/z: 408.0035.

2-[4-(7-Chloro-2,3-dioxo-2,3-dihydroindol-1-ylmethyl) benzyl]isoselenourea hydrobromide (4e) (KS115).

Orange solid, Yield: 70%; mp: 192-194° C.; $^1$H NMR (500 MHz, DMSO-$d_6$): δ 9.24 (s, 2H), 9.14 (s, 2H), 7.62 (dd, J=1.2, 7.3 Hz, 1H), 7.61 (dd, J=1.2, 8.2 Hz, 1H), 7.37 (s, 4H), 7.16 (dd, J=7.3, 8.1 Hz, 1H), 5.20 (s, 2H), 4.51 (s, 2H). $^{13}$C NMR (125 MHz, DMSO-$d_6$): δ 182.3, 166.7, 159.8, 146.0, 140.0, 137.1, 136.2, 129.6, 127.1, 125.3, 124.1, 121.8, 116.2, 44.8, 30.5. MS (ESI) m/z 407 [M+H]; HRMS (ESI) m/z for $C_{17}H_{14}ClN_3O_2Se$ calculated 407.9940, found m/z: 408.0041.

2-[4-(5-Fluoro-2,3-dioxo-2,3-dihydroindol-1-ylmethyl)benzyl]isoselenourea hydrobromide (4f) (KS117).

Orange solid, Yield: 72%; mp: 201-203° C.; $^1$H NMR (500 MHz, DMSO-$d_6$): δ 9.25 (s, 2H), 9.12 (s, 2H), 7.52-7.44 (m, 2H), 7.43-7.37 (m, 4H), 6.98 (dd, J=3.8, 8.6 Hz, 1H), 4.90 (s, 2H), 4.50 (s, 2H). $^{13}$C NMR (125 MHz, DMSO-$d_6$): δ 182.9, 166.7, 159.0, 158.9, 147.0, 136.9, 135.3, 129.8, 128.2, 124.3, 119.2, 112.9, 112.0, 43.2, 30.4. MS (ESI) m/z 392 [M+H]; HR-MS (ESI) m/z for $C_{17}H_{14}FN_3O_2Se$ calculated 392.0235, found m/z: 392.0337.

2-[4-(7-Fluoro-2,3-dioxo-2,3-dihydroindol-1-ylmethyl)benzyl]isoselenourea hydrobromide (4g) (KS119).

Orange solid, Yield: 69%; mp: 206-208° C.; $^1$H NMR (500 MHz, DMSO-$d_6$): δ 9.25 (s, 2H), 9.13 (s, 2H), 7.51 (ddd, J=1.0, 8.4, 11.8 Hz, 1H), 7.48 (dd, J=1.0, 7.4 Hz, 1H), 7.38 (s, 4H), 7.15 (ddd, J=4.0, 7.5, 8.3 Hz, 1H), 4.96 (s, 2H), 4.50 (s, 2H). $^{13}$C NMR (151 MHz, DMSO-$d_6$): δ 182.3, 166.7, 158.9, 147.6, 136.6, 136.3, 129.7, 127.6, 126.2, 125.0, 121.4, 121.3, 45.3, 30.5. MS (ESI) m/z 392 [M+H]; HRMS (ESI) m/z for $C_{17}H_{14}FN_3O_2Se$ calculated 392.0235, found m/z: 392.0334.

2-[4-(2,3-Dioxo-5-trifluoromethyl-2,3-dihydroindol-1-ylmethyl)benzyl]isoselenourea hydrobromide (4h) (KS107).

Yellow solid, Yield: 72%; mp: 218-220° C.; $^1$H NMR (500 MHz, DMSO-$d_6$): δ 9.24 (s, 2H), 9.13 (s, 2H), 7.96 (dd, J=1.3, 8.4 Hz, 1H), 7.89 (d, J=1.2 Hz, 1H), 7.45-7.37 (m, 4H), 7.15 (d, J=8.4 Hz, 1H), 4.96 (s, 2H), 4.50 (s, 2H). $^{13}$C NMR (125 MHz, DMSO): δ 182.1, 166.7, 159.0, 153.4, 136.9, 135.1, 134.9, 129.7, 128.2, 124.4, 124.2, 121.5, 118.9, 112.0, 43.3, 30.4. MS (ESI) m/z 442 [M+H]; HRMS (ESI) m/z for $C_{18}H_{14}F_3N_3O_2Se$ calculated 442.0203, found m/z: 442.0285.

2-[4-(2,3-Dioxo-7-trifluoromethyl-2,3-dihydroindol-1-ylmethyl)benzyl]isoselenourea hydrobromide (4i) (KS123).

Yellow solid, Yield: 62%; mp: 212-214° C.; $^1$H NMR (600 MHz, DMSO-$d_6$): δ 9.25 (s, 2H), 9.13 (s, 2H), 7.85 (d, J=7.4 Hz, 1H), 7.75 (d, J=7.7 Hz, 1H), 7.36-7.31 (m, 5H), 5.05 (s, 2H), 4.50 (s, 2H). $^{13}$C NMR (150 MHz, DMSO-$d_6$): δ 181.3, 166.5, 160.4, 158.4, 136.5, 135.0, 133.6, 129.4, 129.1, 126.5, 123.8, 123.3, 121.8, 112.8, 46.2, 30.4. MS (ESI) m/z 442 [M+H]; HRMS (ESI) m/z for $C_{18}H_{14}F_3N_3O_2Se$ calculated 442.0203, found m/z: 442.0311.

2-[4-(5, 7-Dibromo-2, 3-dioxo-2, 3-dihydroindol-1-ylmethyl)benzyl]isoselenourea hydrobromide (4j) (KS101).

Orange solid, Yield: 78%; mp: 193-195° C.; $^1$H NMR (600 MHz, DMSO-$d_6$): δ 9.29 (s, 2H), 9.17 (s, 2H), 8.01 (d, J=2.0 Hz, 1H), 7.81 (d, J=2.0 Hz, 1H), 7.38 (dd, J=8.5, 12.2 Hz, 4H), 5.24 (s, 2H), 4.54 (s, 2H). $^{13}$C NMR (150 MHz, DMSO-$d_6$): δ 181.1, 166.7, 159.6, 146.7, 143.8, 136.9, 136.1, 129.6, 127.1, 126.8, 123.2, 116.2, 104.7, 44.5, 30.5. MS (ESI) m/z 529 [M+H]; HRMS (ESI) m/z for $C_{17}H_{13}Br_2N_3O_2Se$ calculated 529.8617, found m/z: 529.8618.

2-[4-(5, 7-Dichloro-2, 3-dioxo-2, 3-dihydroindol-1-ylmethyl)benzyl]isoselenourea hydrobromide (4k) (KS103).

Orange solid, Yield: 76%; mp: 213-215° C.; $^1$H NMR (500 MHz, DMSO-$d_6$): δ 9.26 (s, 2H), 9.15 (s, 2H), 8.01 (s, 1H), 7.81 (d, J=2.0 Hz, 1H), 7.37 (s, 4H), 5.24 (s, 2H), 4.51 (s, 2H). $^{13}C$ NMR (125 MHz, DMSO-$d_6$): δ 181.1, 166.7, 159.6, 146.7, 143.8, 136.9, 136.1, 129.5, 127.1, 126.8, 123.2, 116.2, 104.7, 44.5, 30.5. MS (ESI) m/z 441 [M+H]; HR-MS (ESI) m/z for $C_{17}H_{13}Cl_2N_3O_2Se$ calculated 441.9550, found m/z: 441.9545.

2-[4-(7-Bromo-5-fluoro-2,3-dioxo-2,3-dihydroindol-1-ylmethyl)benzyl]isoselenourea hydrobromide (4l) (KS121).

Orange solid, Yield: 65%; mp: 195-197° C.; $^1H$ NMR (600 MHz, DMSO-$d_6$): δ 9.23 (s, 2H), 9.12 (s, 2H), 7.79 (dd, J=2.7, 8.7 Hz, 1H), 7.63 (dd, J=2.6, 6.2 Hz, 1H), 7.37 (s, 4H), 5.24 (s, 2H), 4.51 (s, 2H). $^{13}C$ NMR (150 MHz, DMSO-$d_6$): δ 181.6, 166.6, 159.2, 158.8, 144.1, 137.0, 136.1, 129.5, 128.9, 127.1, 122.6, 112.0, 103.6, 44.4, 30.5. MS (ESI) m/z 469 [M+H]; HRMS (ESI) m/z for $C_{17}H_{13}BrFN_3O_2Se$ calculated 469.9340, found m/z: 469.9437.

Biology

Cell Line and Culture Conditions

Dr. Craig Myers, Penn State College of Medicine, Hershey, PA provided normal human fibroblasts (FF2441). The mutant V600E-BRAF human melanoma cell line 1205 Lu was provided by Dr. Herlyn; Wistar Institute, Philadelphia, PA and UACC 903 was provided by Dr. Mark Nelson; University of Arizona, Tucson, AZ. Colon cancer cells (HCT116, HT29) and multiple myeloma cells (NCIH929, U266, RPMI8226, MM.1R) were procured from ATCC. Cell lines were maintained in a 37° C. humidified 5% $CO_2$ atmosphere incubator and periodically monitored for phenotypic, genotypic characteristics, and tumorigenic potential to validate and confirm cell line identity.

Molecular Docking Studies

Binding interactions of isatin and isatin derivatives with ALDH1A1 (PDB: 4×4L), ALDH2 (PDB: 5L13) and ALDH3A1 (PDB: 4L20) proteins were analyzed using the GLIDE (Grid Ligand Docking with Energetics) docking application in Maestro 10.1 software as described previously. Proteins were prepared using the protein preparation wizard tool (Schrodinger, LLC, 2017) with default parameters. The proteins were optimized and minimized for spatial conformations. Grids were generated based on the location of the crystal ligand-binding site (CM037 for ALDH1A1, psoralen for ALDH2 and CB7 for ALDH3A1), using the GLIDE grid module. Default parameters were used, and no constraints were included during grid generation. Ligand preparation was then performed using the ligprep module in Schrodinger as previously described (Pulla V K, et al., Structure-based drug design of small molecule SIRT1 modulators to treat cancer and metabolic disorders. *J Mol Graph Model* 2014; 52:46-56; Pulla V K, et al., Targeting NAMPT for Therapeutic Intervention in Cancer and Inflammation: Structure-Based Drug Design and Biological Screening. *Chem Biol Drug Des* 2015; 86(4):881-94; Pulla V K, et al., Energy-Based Pharmacophore and Three-Dimensional Quantitative Structure—Activity Relationship (3D-QSAR) Modeling Combined with Virtual Screening To Identify Novel Small-Molecule Inhibitors of Silent Mating-Type Information Regulation 2 Homologue 1 (SIRT1). *J Chem Inf Model* 2016; 56(1):173-87). The docking study was performed using GLIDE 6.6 in Maestro 10.1. The GLIDE algorithm estimates a systematic search of positions, orientations, and conformations of the ligand in the enzyme-binding pocket via a series of hierarchical filters. All hits were subjected to the extra precision (XP) mode of GLIDE. During the docking process, the GLIDE score was used to select the best conformation for each ligand (Id.).

ALDH Isoform-Specific Enzyme Assays

ALDH1A1, 2 and 3A1 enzyme assays were performed as described by the manufacturer (R & D systems). Isoform-specific aldehydes were converted to their respective carboxylic acids along with the conversion of NAD+ to NADH (absorbance at 340 nm). Specifically, 1 μg/mL of ALDH1A1 was treated with 500 nM concentrations of 3(a-l) and 4(a-l) for 15 minutes followed by addition of substrate mixture (10 mM propionaldehyde; 100 mM KCl; 1 mM NAD; 2 mM DTT; 50 mM Tris pH 8.5) and the absorbance of NADH was measured in kinetic mode for 5 minutes. Similarly, 0.5 μg/mL of ALDH2 with 5 μM of 3(a-l) and 4(a-l) was used in the reaction with 2 mM of acetaldehyde as the substrate, and 0.2 μg/mL of ALDH3A1 with 500 nM of 3(a-l) and 4(a-l) was used in the reaction with 1 mM of 4-nitrobenzaldehyde as the substrate.

Cell Viability Assay

Cell viability assays for melanoma, colon cancer, multiple myeloma and FF2441 cells treated with 3(h-l) were performed as described previously Rao P C, et al., Coptisine-induced cell cycle arrest at G2/M phase and reactive oxygen species-dependent mitochondria-mediated apoptosis in non-small-cell lung cancer A549 cells. *Tumour Biol* 2017; 39(3): 1010428317694565; Rao P C, et al., Cytotoxicity of withasteroids: withametelin induces cell cycle arrest at G2/M phase and mitochondria-mediated apoptosis in non-small cell lung cancer A549 cells. *Tumour Biol* 2016; 37(9): 12579-87; Dinavahi S S, et al., Combined inhibition of PDE4 and PI3Kdelta modulates the inflammatory component involved in the progression of chronic obstructive pulmonary disease. Drug Res (Stuttg) 2014; 64(4):214-9). Briefly, 3,000 cells per well were plated in a 96-well plate and incubated overnight at 37° C. in a 5% $CO_2$ atmosphere. Cells were treated with 3(h-l) at various concentrations and incubated for 72 hours. 20 μL of MTS reagent was then added into each well and formation of tetrazolium was measured by absorbance after 1 hour at 492 nm. $IC_{50}$ values for each experimental group were measured in 3 independent experiments using GraphPad Prism version 7.04 (GraphPad Software, La Jolla, CA). Selectivity indices for 3(h-l) were calculated as a ratio of $IC_{50}$s in fibroblasts/average of $IC_{50}$s in melanoma cell lines.

Toxicity Studies

To determine the toxicity of 3(h-l), compounds were injected i.p. into Swiss-Webster mice once daily for 14 days (Id.). Animals were monitored for changes in body weight, behavior and physical distress compared to DMSO control.

ROS Assay

ROS activity was measured using DCFDA dye. Briefly, cells were treated with 5 μM of 3(h-l) for 24 hours. Cells were incubated with 10 μM of DCFDA for 1 hour, and fluorescence was measured at 485 nm excitation and 510 nm emission. ROS levels in treated cells were compared to DMSO control.

Lipid Peroxidation and Toxic Aldehyde Accumulation

Lipid peroxidation and toxic aldehyde accumulation was measured using the thiobarbituric acid reactive substances (TBARS) kit according to the manufacturer's instructions (Yagi K. Simple assay for the level of total lipid peroxides in serum or plasma. *Methods Mol Biol* 1998; 108:101-6). Briefly, cells were treated with 5 μM of 3(h-l) for 24 hours. Cell pellets were lysed in PBS by sonication on ice. Lipids in the lysates were hydrolyzed in the presence of acetic acid and sodium hydroxide. Free MDA released from lipids was measured by the reaction to TBA colorimetrically at 530 nm. Lipid peroxidation in treated cells was compared to DMSO control.

Statistics

Statistical analysis was undertaken using the one-way/two-way ANOVA GraphPad PRISM Version 7.04 software. Dunnett's as post hoc analysis was performed when there was a significant difference. A p-value of <0.05 was considered statistically significant.

STUDY 3

Cell Viability Assays

Figure 21A:
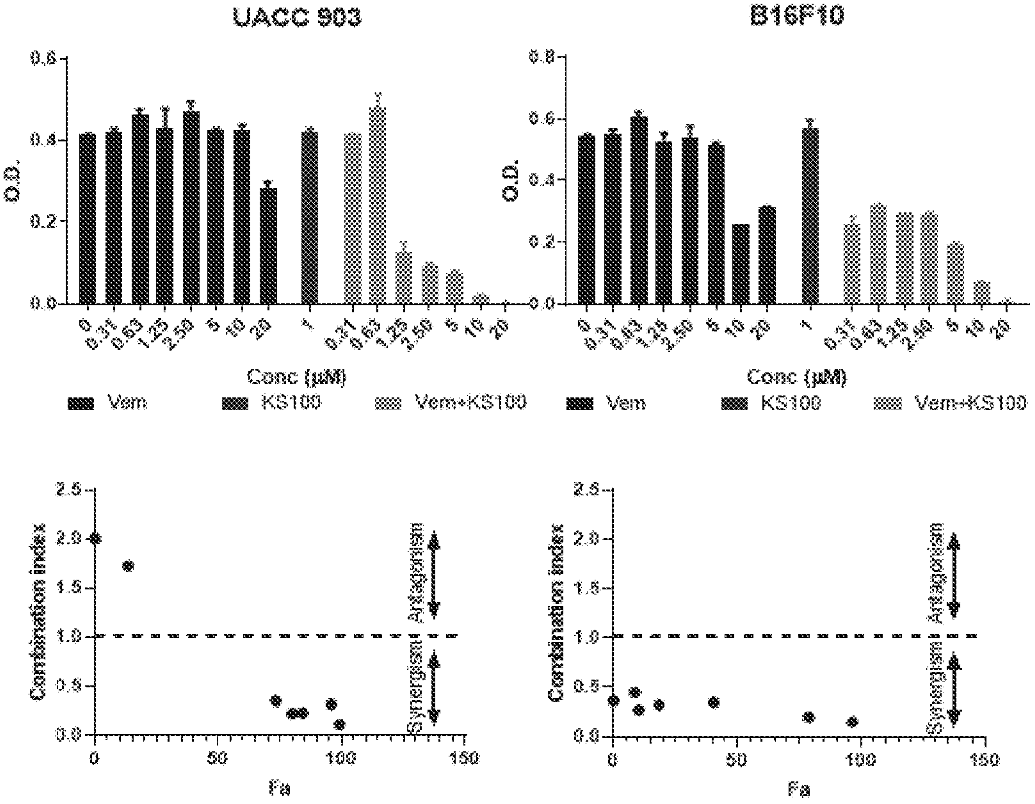
FIG. 21A. Combo of Vemurafenib+KS100 is more effective. KS100 synergistic with Vemurafenib in vitro-MTS assay.

Briefly, 5,000 cells per well were plated in a 96-well plate and incubated overnight at 37° C. in a 5% $CO_2$ atmosphere. Cells were treated with agents at various concentrations and incubated for 72 hours. 20 μL of MTS reagent was then added into each well and formation of tetrazolium was measured by absorbance after 1 hour at 492 nm. $IC_{50}$ values or % cells for each experimental group were measured in three independent experiments. Combination indices were calculated to identify synergy using Calcusyn software. (FIG. 21A)

AldeRed ALDH Detection Assay

Figure 21B:
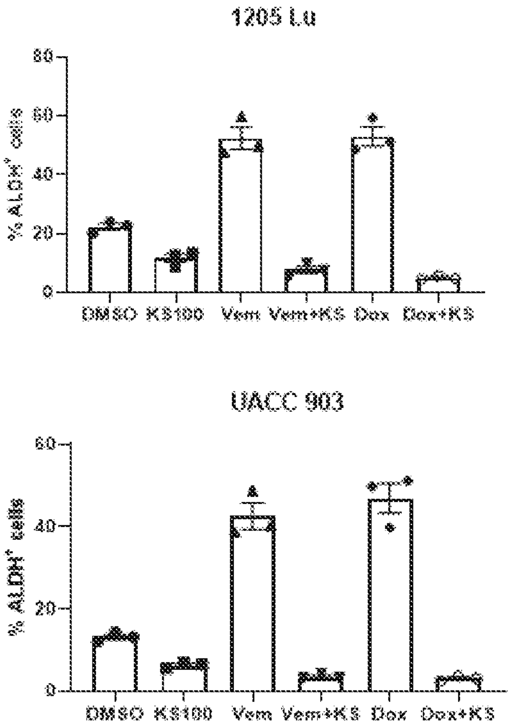
FIG. 21B. KS synergistic with Vemurafenib or doxorubicin in vitro ALDH activity assay.

The AldeRed ALDH detection assay (Millipore) was used to distinguish ALDH+ cells from the ALDH− cells. Briefly, cells were incubated with 5 μM of ALDH inhibitor, 10 μM of Vemurafenib or DMSO or combination for 24 hours. Cells were washed with PBS and stained with AldeRed reagent (AldeRed 588-A) for 1 hour as per the manufacturer's instructions. Cells were acquired by BD Fortessa flow cytometer and gated for ALDH+ cells using DEAB as a negative control. (FIG. 21B)

Tumor Efficacy and Toxicity Assessment

Figure 22:
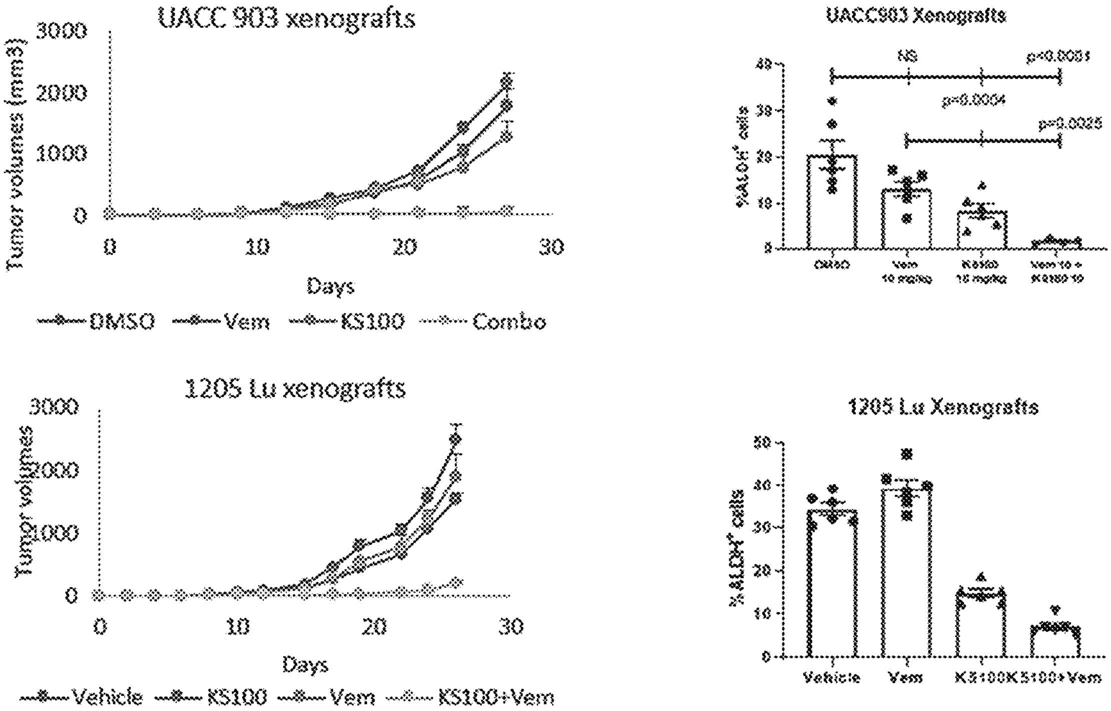
FIG. 22. KS100 synergistic with Vemurafenib in-vivo along with corresponding reduction in ALDH activities FIG. 23A. KS100 effective in inhibiting resistance disease in SM1 models. KS100 inhibits in-vivo Vemurafenib resistance with corresponding reduction in ALDH activity.
Figure 23A:
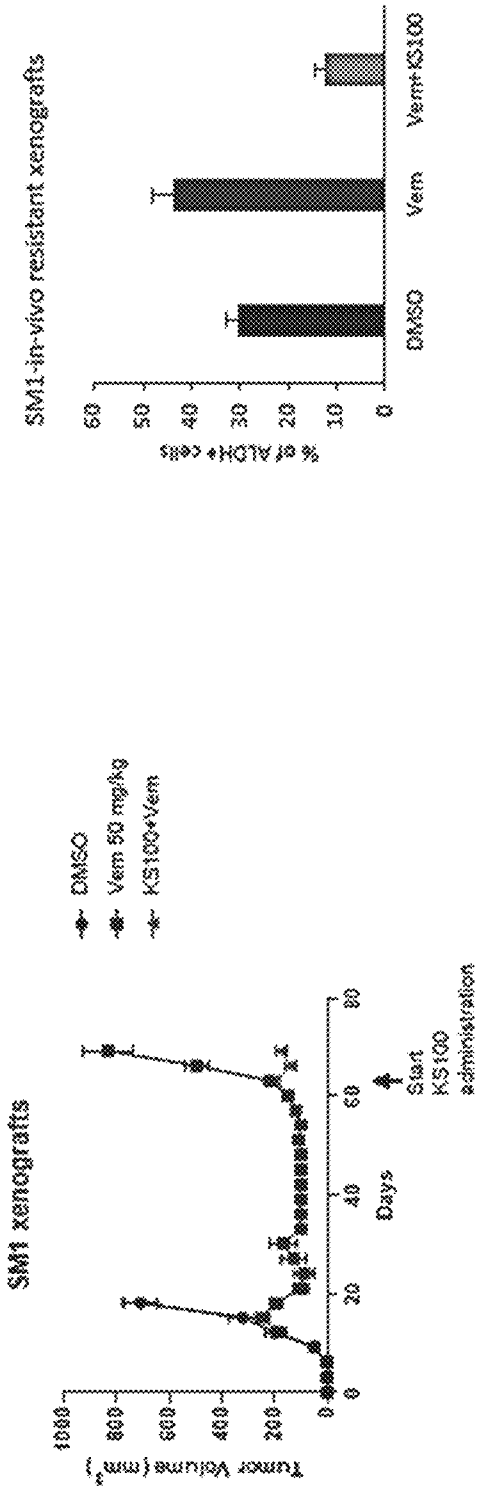
FIG. 23B. KS100 inhibits in-vitro resistant SM-1VR with corresponding reduction in ALDH activity.
Figure 23B:
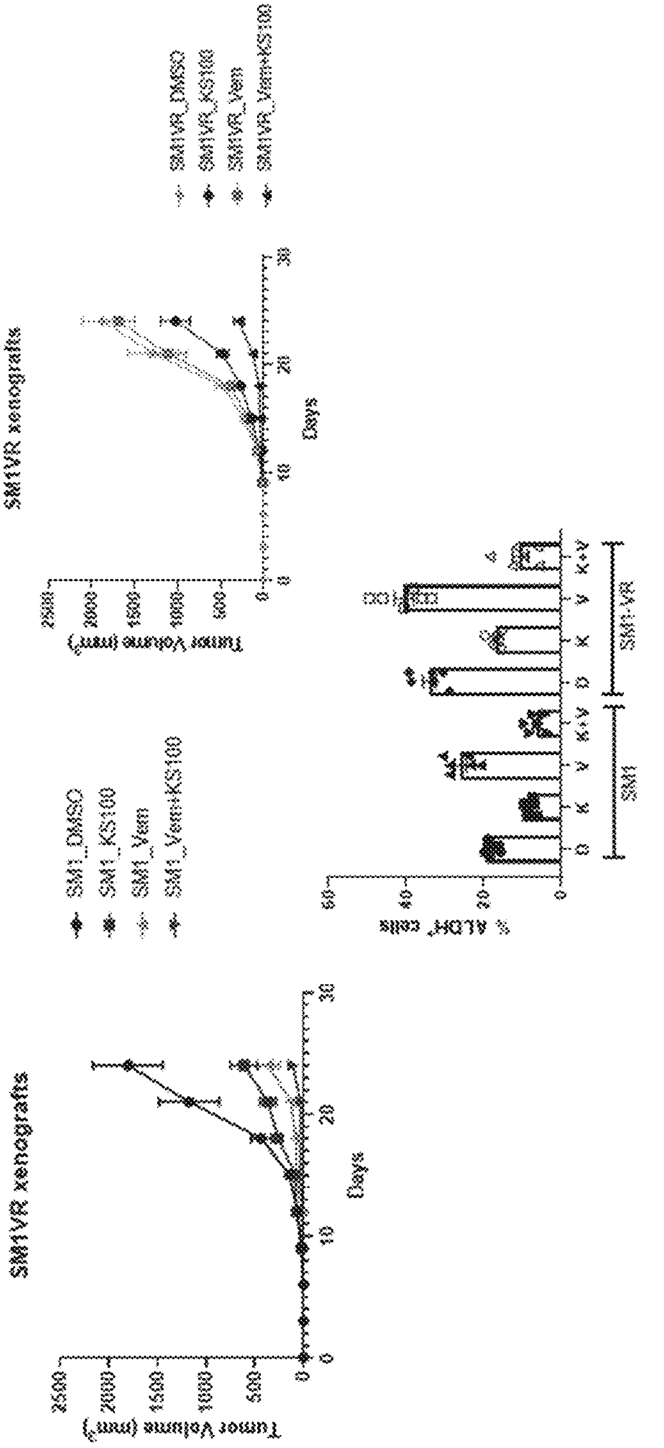

Efficacy and toxicity studies were performed in nude mice. Briefly, 1 million cells were injected in both flanks of 4-6 week old female nude Balb/c mice (Envigo). After a week, when the tumors were vascularized, animals were either treated with NanoKS100, Vemurafenib, or combination or empty liposomes at indicated doses. Tumor volumes, animal weight and behavior were monitored continuously every other day. Animals were sacrificed after tumor volumes in the empty liposome groups exceeded 1,500 $mm^3$ and tumors were subsequently collected. SM-1VR cells, were generated in-vitro by continuous culturing of SM-1 cells in presence of $IC_{50}$ concentration of Vemurafenib. At the end of experiment, single cell suspension of tumors were made to evaluate for ALDH activity as described above. (FIGS. 22 and 23A-23B)

In Vitro Evaluation of Calreticulin Expression

Figure 24:
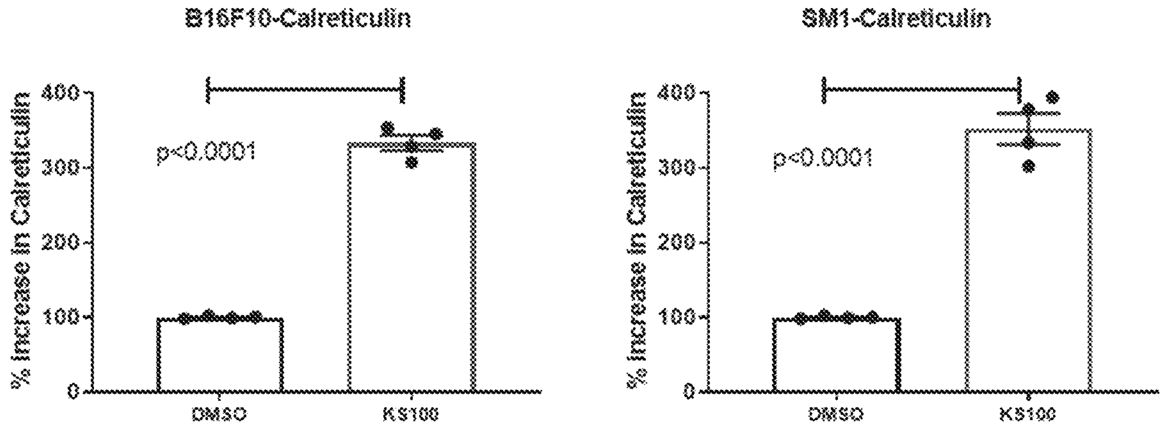
FIG. 24. KS100 induces calreticulin expression to increase immunologic cell death.

B16.F10 or SM1 melanoma cells were seeded at 1.5-2.0×$10^5$ cells per well in 24-well plates in RPMI-1640 medium containing standard supplements and 10% FBS and incubated overnight at 37° C., 5% $CO_2$. Compounds solubilized in DMSO were added at the indicated concentrations and incubated for a further 24 hours at 37° C., 5% $CO_2$. Control wells were treated with similar dilutions of vehicle. Cells were trypsinized and washed with FACS buffer (2% FBS+0.1% $NaN_3$ in PBS) and seeded at 1-2×$10^5$ per well in 96-well round-bottom plates. Cells were stained with rabbit anti-calreticulin polyclonal antibody (1:100, Abcam ab2907) in FACS buffer for 30 minutes at 4° C. Following two washes, cells were labeled with goat anti-rabbit Alexa Fluor 488 (1:500, Thermo Fisher A11070) in FACS buffer for 30 minutes at 4° C. Cells were washed twice and labeled with 7-aminoactinomysin D (7AAD; 0.25 g, BD Pharmingen 51-68981E) in order to exclude non-viable cells. All samples were immediately run on a BD LSR Fortessa flow cytometer and the data analyzed using FlowJo software. (FIG. 24)

Treatment of Mice and In Vivo Tumor Growth Analysis

Figure 25:
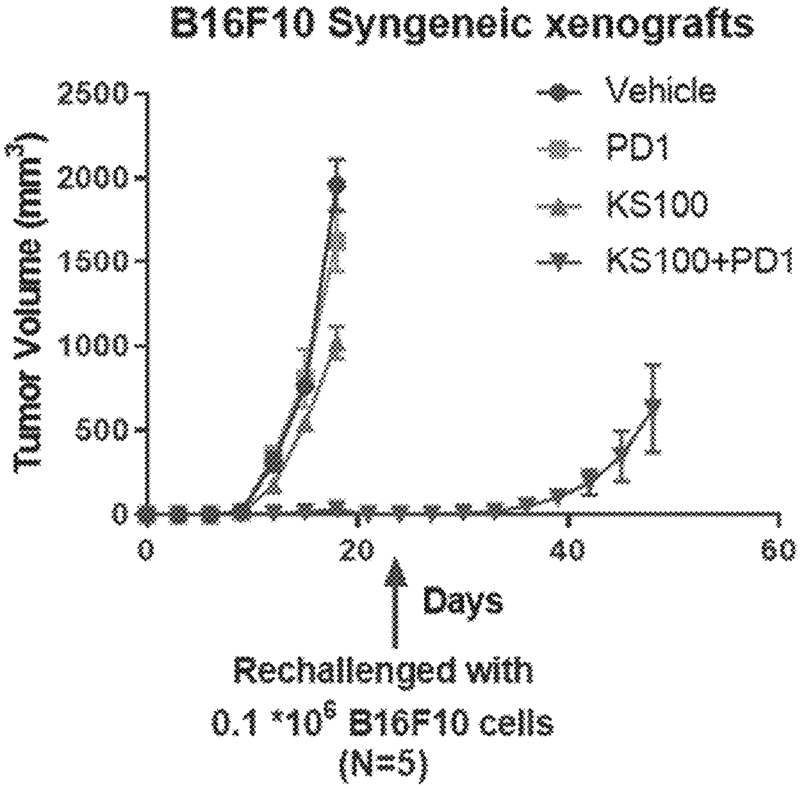
FIG. 25. KS100+anti-PD1 is effective in inhibiting B16F10 tumor volumes.

C57BL/6J mice were purchased from The Jackson Laboratory at 6-8 weeks of age, maintained in a HEPA-filtered ventilated rack system and used within 2 weeks of receipt. Mice were housed 5 or less per cage, fed and watered ad libitum, and maintained in a 12-hour light/dark cycle. Groups of mice were inoculated with 1×$10^5$ freshly cultured B16.F10 tumor cells subcutaneously in the left flank. Mice were monitored for the development of tumors and when palpable were randomized into groups. Mice received αPD-1 (clone RMP1-14; BioXCell or Leinco Technologies, Inc.) or control rat IgG (Sigma) at 200 ug/day intraperitoneally in a volume of 200 ul PBS twice per week. Mice received daily i.v. treatment of NanoKS100 liposomes at 120 mg/kg or combination of both or vehicle till the end of the experiment. Vehicle for in vivo delivery of the compounds consisted of empty liposomes in PBS. Tumors volumes and animal weights were monitored every other day. Mice were euthanized when the tumor volume exceeded 1500 mm3, developed ascites or necrosis or when mice became lethargic. (FIG. 25)

Immune Cell Analysis

Figure 26:
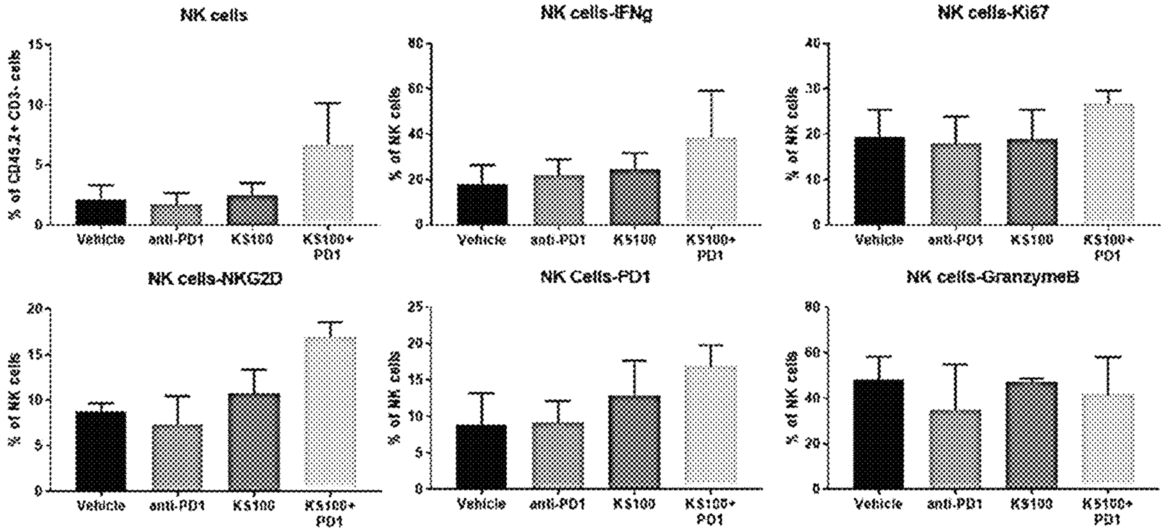
FIG. 26. KS100+PD1 is effective in inducing NK cell number and function.
Figure 27:
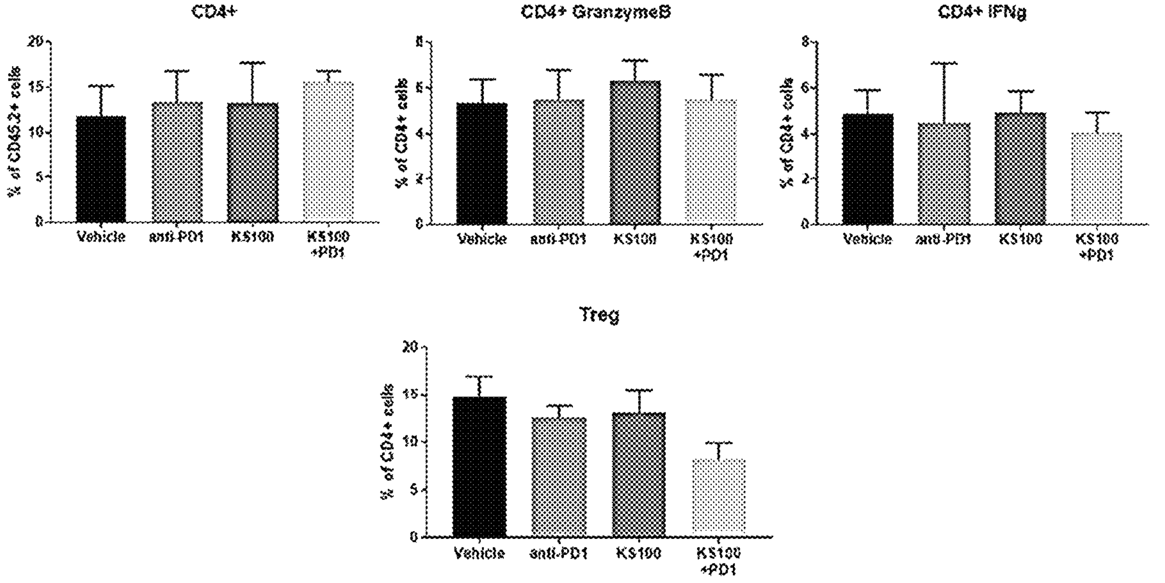
FIG. 27. KS100+PD1 is effective in reducing Tregs cells.
Figure 28:
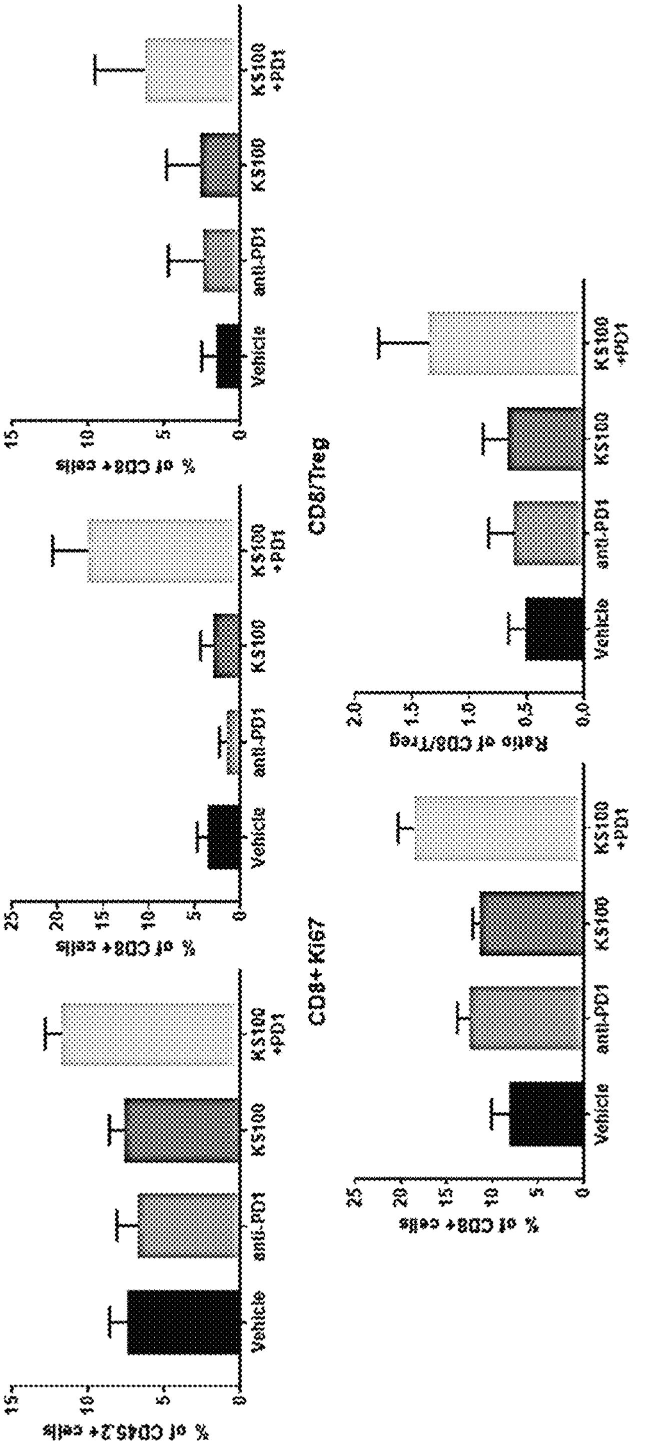
FIG. 28. KS100+PD1 is effective in inducing CD8+ T-cell number and function.

The spleens and tumors from B16.$F_{10}$ treated mice were dissected into RPMI supplemented with 10% FBS and maintained on ice. Tumors were dissociated by digesting with Colagenase-IV. Tumors and spleens were passed through a wire mesh to form a single cell suspension. Aliquots of ~2×$10^6$ cells were stained with commercially available antibodies prior to analysis on an LSR Fortessa flow cytometer (BD Biosciences) in the Penn State Cancer Institute Flow Cytometry Shared Resource. Samples were stained with fixable viability stain (FVS-AF700) prior to analysis to eliminate dead cells. Data were analyzed using FlowJo software (v10.4, FlowJo, LLC). Antibodies used include: CD45.2-BV480 (clone 104), CD4-BB700 (clone RM4-5), CD8-BV786 (clone 53-9.7), NK1.1-FITC (clone PK136), CD3-PE (clone 145-2C11), CD11c-APC-Cy7 (clone HL3), and CD11b-APC (clone M1/70), F4/80-PerCP-Cy5.5 (clone T45-2342), Ly6C-BV786 (clone AL-21), Ly6G-VF450 (clone1A8), NKG2D-BV711 (clone CX5), CD25-PE-texas Red (PC61), PD1-PE/Dazzle (RMP1-30), FoxP3-APC (MF23). Antibodies were purchased from BD Biosciences, BioLegend, eBioscience or Tonbo Biosciences. Live cells were gated on the CD45.2+/FVS− population. (FIGS. 26-28)

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

What is claimed is:

1. A method of treating cancer in a subject, comprising: administering a therapeutically effective amount of a checkpoint inhibitor or a BRAF inhibitor and a composition comprising a compound of Formula I

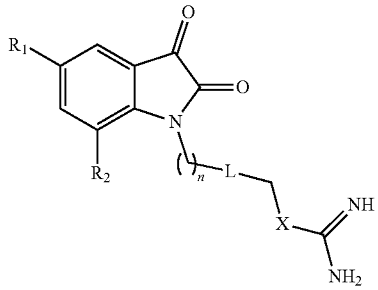

I wherein,

X is S or Se;

L is a $C_1$-$C_8$ alkyl, $C_2$-$C_8$ alkenyl, $C_2$-$C_8$ alkynyl, $C_5$-$C_6$ cycloalkyl, $C_5$-$C_6$ heterocycloalkyl, or phenyl, any of which is optionally substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$;

n is 0, 1, 2, or 3;

$R_1$ and $R_2$ are each independently chosen from H, F, Cl, Br, I, $NO_2$, OH, $C_1$-$C_6$ alkyl, $C_1$-$C_6$ alkoxyl, or $C_1$-$C_6$ haloalkyl, or a pharmaceutically acceptable salt thereof.

2. The method of claim 1, wherein L is a $C_1$-$C_8$ alkyl, $C_2$-$C_8$ alkenyl, $C_2$-$C_8$ alkynyl, or $C_5$-$C_6$ cycloalkyl, any of which are optionally substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$.

3. The method of claim 1, wherein L is a $C_5$-$C_6$ heterocycloalkyl optionally substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$.

4. The method of claim 1, wherein L is a phenyl optionally substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$.

5. The method of claim 1, wherein L is a heteroaryl optionally substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$.

6. The method of claim 1, wherein at least one of $R_1$ and $R_2$ is a halogen.

7. The method of claim 1, wherein at least one of $R_1$ and $R_2$ is H.

8. The method of claim 1, wherein the compound is KS100 free base (FB): 2-[4-(5, 7-Dibromo-2, 3-dioxo-2, 3-dihydroindol-1-ylmethyl)benzyl]isothiourea.

9. The method of claim 1, wherein compound is selected from the group consisting of: KS104 (3a): 2-[4-(2,3-Dioxo-2,3-dihydroindol-1-ylmethyl)benzyl]isothiourea hydrobromide; KS104FB: 2-[4-(2,3-Dioxo-2,3-dihydroindol-1-ylmethyl)benzyl]isothiourea; KS108 (3b):2-[4-(5-Bromo-2,3-dioxo-2,3-dihydroindol-1-ylmethyl)benzyl]isothiourea hydrobromide; KS100 FB: 2-[4-(5-Bromo-2,3-dioxo-2,3-dihydroindol-1-ylmethyl)benzyl]isothiourea; KS110 (3c): 2-[4-(7-Bromo-2,3-dioxo-2,3-dihydroindol-1-ylmethyl) benzyl]isothiourea hydrobromide; KS110 FB: 2-[4-(7-Bromo-2,3-dioxo-2,3-dihydroindol-1-ylmethyl)benzyl]isothiourea; KS112 (3d): 2-[4-(5-Chloro-2,3-dioxo-2,3-dihydroindol-1-ylmethyl)benzyl]isothiourea hydrobromide; KS112 FB: 2-[4-(5-Chloro-2,3-dioxo-2,3-dihydroindol-1-ylmethyl)benzyl]isothiourea; KS114 (3e): 2-[4-(7-Chloro-2, 3-dioxo-2,3-dihydroindol-1-ylmethyl)benzyl]isothiourea hydrobromide; KS114 FB: 2-[4-(7-Chloro-2,3-dioxo-2,3-dihydroindol-1-ylmethyl)benzyl]isothiourea; KS116 (3f): 2-[4-(5-Fluoro-2,3-dioxo-2,3-dihydroindol-1-ylmethyl)benzyl]isothiourea hydrobromide; KS116 FB: 2-[4-(5-Fluoro-2,3-dioxo-2,3-dihydroindol-1-ylmethyl)benzyl]isothiourea; KS118 (3g): 2-[4-(7-Fluoro-2,3-dioxo-2,3-dihydroindol-1-ylmethyl)benzyl]isothiourea hydrobromide; KS118 FB: 2-[4-(7-Fluoro-2,3-dioxo-2,3-dihydroindol-1-ylmethyl)benzyl]isothiourea; KS106 (3h): 2-[4-(2,3-Dioxo-5-trifluoromethyl-2,3-dihydroindol-1-ylmethyl)benzyl]isothiourea hydrobromide; KS106 FB: 2-[4-(2,3-Dioxo-5-trifluoromethyl-2,3-dihydroindol-1-ylmethyl)benzyl]isothiourea; KS122 (3i): 2-[4-(2,3-Dioxo-7-trifluoromethyl-2,3-dihydroindol-1-ylmethyl)benzyl]isothiourea hydrobromide; KS122 FB: 2-[4-(2,3-Dioxo-7-trifluoromethyl-2,3-dihydroindol-1-ylmethyl)benzyl]isothiourea; KS100 (3j): 2-[4-(5, 7-Dibromo-2, 3-dioxo-2, 3-dihydroindol-1-ylmethyl)benzyl]isothiourea hydrobromide; KS100 FB: 2-[4-(5, 7-Dibromo-2, 3-dioxo-2, 3-dihydroindol-1-ylmethyl)benzyl]isothiourea; KS102 (3k): 2-[4-(5,7-Dichloro-2,3-dioxo-2,3-dihydroindol-1-ylmethyl)benzyl]isothiourea hydrobromide; KS102 FB: 2-[4-(5, 7-Dichloro-2,3-dioxo-2,3-dihydroindol-1-ylmethyl)benzyl] isothiourea; KS120 (3l): 2-[4-(7-Bromo-5-fluoro-2,3-dioxo-2,3-dihydroindol-1-ylmethyl)benzyl]isothiourea hydrobromide; KS120 FB: 2-[4-(7-Bromo-5-fluoro-2,3-dioxo-2,3-dihydroindol-1-ylmethyl)benzyl]isothiourea; KS105 (4a): 2-[4-(2,3-Dioxo-2,3-dihydroindol-1-ylmethyl) benzyl]isoselenourea hydrobromide; KS105 FB: 2-[4-(2,3-Dioxo-2,3-dihydroindol-1-ylmethyl)benzyl]isoselenourea; KS109 (4b): 2-[4-(5-Bromo-2,3-dioxo-2,3-dihydroindol-1-ylmethyl)benzyl]isoselenourea hydrobromide; KS109 FB: 2-[4-(5-Bromo-2,3-dioxo-2,3-dihydroindol-1-ylmethyl) benzyl]isoselenourea; KS111 (4c): 2-[4-(7-Bromo-2,3-dioxo-2,3-dihydroindol-1-ylmethyl)benzyl]isoselenourea hydrobromide; KS111 FB: 2-[4-(7-Bromo-2,3-dioxo-2,3-dihydroindol-1-ylmethyl)benzyl]isoselenourea; KS113 (4d): 2-[4-(5-Chloro-2,3-dioxo-2,3-dihydroindol-1-ylmethyl) benzyl]isoselenourea hydrobromide; KS113 FB: 2-[4-(5-Chloro-2,3-dioxo-2,3-dihydroindol-1-ylmethyl)benzyl] isoselenourea; KS115 (4e): 2-[4-(7-Chloro-2,3-dioxo-2,3-dihydroindol-1-ylmethyl)benzyl]isoselenourea hydrobromide; KS115 FB: 2-[4-(7-Chloro-2,3-dioxo-2,3-dihydroindol-1-ylmethyl)benzyl]isoselenourea; KS117 (4f): 2-[4-(5-Fluoro-2,3-dioxo-2,3-dihydroindol-1-ylmethyl)benzyl]isoselenourea hydrobromide; KS117 FB: 2-[4-(5-Fluoro-2,3-dioxo-2,3-dihydroindol-1-ylmethyl)benzyl] isoselenourea; KS119 (4g): 2-[4-(7-Fluoro-2,3-dioxo-2,3-dihydroindol-1-ylmethyl)benzyl]isoselenourea hydrobromide; KS119 FB: 2-[4-(7-Fluoro-2,3-dioxo-2,3-dihydroindol-1-ylmethyl)benzyl]isoselenourea; KS107 (4h): 2-[4-(2,3-Dioxo-5-trifluoromethyl-2,3-dihydroindol-1-ylmethyl)benzyl]isoselenourea hydrobromide; KS107 FB: 2-[4-(2,3-Dioxo-5-trifluoromethyl-2,3-dihydroindol-1-ylmethyl) benzyl]isoselenourea; KS123 (4i): 2-[4-(2,3-Dioxo-7-trifluoromethyl-2,3-dihydroindol-1-ylmethyl)benzyl] isoselenourea hydrobromide; KS123 FB: 2-[4-(2,3-Dioxo-7-trifluoromethyl-2,3-dihydroindol-1-ylmethyl)benzyl] isoselenourea; KS101 (4j): 2-[4-(5, 7-Dibromo-2, 3-dioxo-2, 3-dihydroindol-1-ylmethyl)benzyl]isoselenourea hydrobromide; KS101 FB: 2-[4-(5, 7-Dibromo-2, 3-dioxo-2, 3-dihydroindol-1-ylmethyl)benzyl]isoselenourea; KS103 (4k): 2-[4-(5, 7-Dichloro-2, 3-dioxo-2, 3-dihydroindol-1-ylmethyl)benzyl]isoselenourea hydrobromide; KS103 FB: 2-[4-(5, 7-Dichloro-2, 3-dioxo-2, 3-dihydroindol-1-ylmethyl)benzyl]isoselenourea; KS121 (4l): 2-[4-(7-Bromo-5-fluoro-2,3-dioxo-2,3-dihydroindol-1-ylmethyl)benzyl]

isoselenourea hydrobromide; and KS121 FB: 2-[4-(7-Bromo-5-fluoro-2,3-dioxo-2,3-dihydroindol-1-ylmethyl) benzyl]isoselenourea.

10. The method of claim 1, wherein the compound is KS100 ((3j): 2-[4-(5, 7-Dibromo-2, 3-dioxo-2, 3-dihydroindol-1-ylmethyl)benzyl]isothiourea hydrobromide).

11. The method of claim 1, wherein the composition further comprises a pharmaceutically acceptable carrier and wherein the pharmaceutically acceptable carrier comprises liposomes.

12. The method of claim 1, wherein the checkpoint inhibitor is a PD-1 inhibitor, PD-L1 inhibitor, or CTLA4 inhibitor.

13. The method of claim 12, wherein the checkpoint inhibitor is chosen from anti-PD-1, nivolumab, pembrolizumab, cemiplimab, ipilimumab, atezolizumab, avelumab, durvalumab, or combinations thereof.

14. The method of claim 1, wherein the BRAF inhibitor is sorafenib, vemurafenib, dabrafenib, encorafenib, or combinations thereof.

15. The method of claim 1, wherein the cancer is a cancer characterized by overexpression of one or more aldehyde dehydrogenases selected from ALDH1A1, ALDH1A2, ALDH1A3, ALDH1L1, ALDH2, ALDH3A1, ALDH5A1, ALDH18A1, or a combination of any two or more thereof.

16. The method of claim 1, wherein the cancer is selected from the group consisting of: melanoma, liver cancer, prostate cancer, breast cancer, brain cancer, stomach cancer, pancreas cancer, blood cell cancer, uterine cancer, cervical cancer, ovarian cancer, lung cancer, colon cancer, connective tissue cancer (sarcomas), soft tissue cancer, and head and neck squamous cell carcinoma.

17. A composition comprising a checkpoint inhibitor or a BRAF inhibitor and a composition comprising a compound of Formula I

I

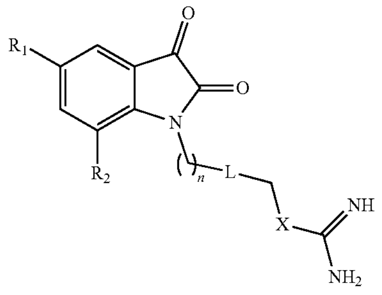

wherein,

X is S or Se;

L is a $C_1$-$C_8$ alkyl, $C_2$-$C_8$ alkenyl, $C_2$-$C_8$ alkynyl, $C_5$-$C_6$ cycloalkyl, $C_5$-$C_6$ heterocycloalkyl, or phenyl, any of which is optionally substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$;

n is 0, 1, 2, or 3;

$R_1$ and $R_2$ are each independently chosen from H, F, Cl, Br, I, $NO_2$, OH, $C_1$-$C_6$ alkyl, $C_1$-$C_6$ alkoxyl, or $C_1$-$C_6$ haloalkyl, or a pharmaceutically acceptable salt thereof.

18. The composition of claim 17, wherein L is a $C_1$-$C_8$ alkyl, $C_2$-$C_8$ alkenyl, $C_2$-$C_8$ alkynyl, or $C_5$-$C_6$ cycloalkyl, any of which are optionally substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$.

19. The composition of claim 17, wherein L is a $C_5$-$C_6$ heterocycloalkyl optionally substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$.

20. The composition of claim 17, wherein L is a phenyl optionally substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$.

21. The composition of claim 17, wherein L is a heteroaryl optionally substituted with $C_1$-$C_6$ alkyl, $C_1$-$C_6$ alkoxy, $C_2$-$C_6$ alkenyl, $C_2$-$C_6$ alkynyl, $C_1$-$C_6$ haloalkyl, $NH_2$, $CO_2H$, $CO_2C_1$-$C_6$ alkyl, halide, OH, or $NO_2$.

22. The composition of claim 17, wherein at least one of $R_1$ and $R_2$ is a halogen.

23. The composition of claim 17, wherein at least one of $R_1$ and $R_2$ is H.

24. The composition of claim 17, wherein the compound is KS100 free base (FB): 2-[4-(5, 7-Dibromo-2, 3-dioxo-2, 3-dihydroindol-1-ylmethyl)benzyl]isothiourea.

25. The composition of claim 17, wherein compound is selected from the group consisting of: KS104 (3a): 2-[4-(2, 3-Dioxo-2,3-dihydroindol-1-ylmethyl)benzyl]isothiourea hydrobromide; KS104FB: 2-[4-(2,3-Dioxo-2,3-dihydroindol-1-ylmethyl)benzyl]isothiourea; KS108 (3b):2-[4-(5-Bromo-2,3-dioxo-2,3-dihydroindol-1-ylmethyl)benzyl]isothiourea hydrobromide; KS100 FB: 2-[4-(5-Bromo-2,3-dioxo-2,3-dihydroindol-1-ylmethyl)benzyl]isothiourea; KS110 (3c): 2-[4-(7-Bromo-2,3-dioxo-2,3-dihydroindol-1-ylmethyl)benzyl]isothiourea hydrobromide; KS110 FB: 2-[4-(7-Bromo-2,3-dioxo-2,3-dihydroindol-1-ylmethyl) benzyl]isothiourea; KS112 (3d): 2-[4-(5-Chloro-2,3-dioxo-2,3-dihydroindol-1-ylmethyl)benzyl]isothiourea hydrobromide; KS112 FB: 2-[4-(5-Chloro-2,3-dioxo-2,3-dihydroindol-1-ylmethyl)benzyl]isothiourea; KS114 (3e): 2-[4-(7-Chloro-2,3-dioxo-2,3-dihydroindol-1-ylmethyl) benzyl]isothiourea hydrobromide; KS114 FB: 2-[4-(7-Chloro-2,3-dioxo-2,3-dihydroindol-1-ylmethyl)benzyl]isothiourea; KS116 (3f): 2-[4-(5-Fluoro-2,3-dioxo-2,3-dihydroindol-1-ylmethyl)benzyl]isothiourea hydrobromide; KS116 FB: 2-[4-(5-Fluoro-2,3-dioxo-2,3-dihydroindol-1-ylmethyl)benzyl]isothiourea; KS118 (3g): 2-[4-(7-Fluoro-2, 3-dioxo-2,3-dihydroindol-1-ylmethyl)benzyl]isothiourea hydrobromide; KS118 FB: 2-[4-(7-Fluoro-2,3-dioxo-2,3-dihydroindol-1-ylmethyl)benzyl]isothiourea; KS106 (3h): 2-[4-(2,3-Dioxo-5-trifluoromethyl-2,3-dihydroindol-1-ylmethyl)benzyl]isothiourea hydrobromide; KS106 FB: 2-[4-(2, 3-Dioxo-5-trifluoromethyl-2,3-dihydroindol-1-ylmethyl) benzyl]isothiourea; KS122 (3i): 2-[4-(2,3-Dioxo-7-trifluoromethyl-2,3-dihydroindol-1-ylmethyl)benzyl] isothiourea hydrobromide; KS122 FB: 2-[4-(2,3-Dioxo-7-trifluoromethyl-2,3-dihydroindol-1-ylmethyl)benzyl] isothiourea; KS100 (3j): 2-[4-(5, 7-Dibromo-2, 3-dioxo-2, 3-dihydroindol-1-ylmethyl)benzyl]isothiourea hydrobromide; KS100 FB: 2-[4-(5, 7-Dibromo-2, 3-dioxo-2, 3-dihydroindol-1-ylmethyl)benzyl]isothiourea; KS102 (3k): 2-[4-(5,7-Dichloro-2,3-dioxo-2,3-dihydroindol-1-ylmethyl) benzyl]isothiourea hydrobromide; KS102 FB: 2-[4-(5,7-Dichloro-2,3-dioxo-2,3-dihydroindol-1-ylmethyl)benzyl] isothiourea; KS120 (3l): 2-[4-(7-Bromo-5-fluoro-2,3-dioxo-2,3-dihydroindol-1-ylmethyl)benzyl]isothiourea hydrobromide; KS120 FB: 2-[4-(7-Bromo-5-fluoro-2,3-dioxo-2,3-dihydroindol-1-ylmethyl)benzyl]isothiourea; KS105 (4a): 2-[4-(2,3-Dioxo-2,3-dihydroindol-1-ylmethyl) benzyl]isoselenourea hydrobromide; KS105 FB: 2-[4-(2,3-Dioxo-2,3-dihydroindol-1-ylmethyl)benzyl]isoselenourea; KS109 (4b): 2-[4-(5-Bromo-2,3-dioxo-2,3-dihydroindol-1-ylmethyl)benzyl]isoselenourea hydrobromide; KS109 FB:

2-[4-(5-Bromo-2,3-dioxo-2,3-dihydroindol-1-ylmethyl) benzyl]isoselenourea; KS111 (4c): 2-[4-(7-Bromo-2,3-dioxo-2,3-dihydroindol-1-ylmethyl)benzyl]isoselenourea hydrobromide; KS111 FB: 2-[4-(7-Bromo-2,3-dioxo-2,3-dihydroindol-1-ylmethyl)benzyl]isoselenourea; KS113 (4d): 2-[4-(5-Chloro-2,3-dioxo-2,3-dihydroindol-1-ylmethyl) benzyl]isoselenourea hydrobromide; KS113 FB: 2-[4-(5-Chloro-2,3-dioxo-2,3-dihydroindol-1-ylmethyl)benzyl] isoselenourea; KS115 (4e): 2-[4-(7-Chloro-2,3-dioxo-2,3-dihydroindol-1-ylmethyl)benzyl]isoselenourea hydrobromide; KS115 FB: 2-[4-(7-Chloro-2,3-dioxo-2,3-dihydroindol-1-ylmethyl)benzyl]isoselenourea; KS117 (4f): 2-[4-(5-Fluoro-2,3-dioxo-2,3-dihydroindol-1-ylmethyl)benzyl]isoselenourea hydrobromide; KS117 FB: 2-[4-(5-Fluoro-2,3-dioxo-2,3-dihydroindol-1-ylmethyl)benzyl] isoselenourea; KS119 (4g): 2-[4-(7-Fluoro-2,3-dioxo-2,3-dihydroindol-1-ylmethyl)benzyl]isoselenourea hydrobromide; KS119 FB: 2-[4-(7-Fluoro-2,3-dioxo-2,3-dihydroindol-1-ylmethyl)benzyl]isoselenourea; KS107 (4h): 2-[4-(2,3-Dioxo-5-trifluoromethyl-2,3-dihydroindol-1-ylmethyl)benzyl]isoselenourea hydrobromide; KS107 FB: 2-[4-(2,3-Dioxo-5-trifluoromethyl-2,3-dihydroindol-1-ylmethyl) benzyl]isoselenourea; KS123 (4i): 2-[4-(2,3-Dioxo-7-trifluoromethyl-2,3-dihydroindol-1-ylmethyl)benzyl] isoselenourea hydrobromide; KS123 FB: 2-[4-(2,3-Dioxo-7-trifluoromethyl-2,3-dihydroindol-1-ylmethyl)benzyl] isoselenourea; KS101 (4j): 2-[4-(5, 7-Dibromo-2, 3-dioxo-2, 3-dihydroindol-1-ylmethyl)benzyl]isoselenourea hydrobromide; KS101 FB: 2-[4-(5, 7-Dibromo-2, 3-dioxo-2, 3-dihydroindol-1-ylmethyl)benzyl]isoselenourea; KS103 (4k): 2-[4-(5, 7-Dichloro-2, 3-dioxo-2, 3-dihydroindol-1-ylmethyl)benzyl]isoselenourea hydrobromide; KS103 FB: 2-[4-(5, 7-Dichloro-2, 3-dioxo-2, 3-dihydroindol-1-ylmethyl)benzyl]isoselenourea; KS121 (4l): 2-[4-(7-Bromo-5-fluoro-2,3-dioxo-2,3-dihydroindol-1-ylmethyl)benzyl] isoselenourea hydrobromide; and KS121 FB: 2-[4-(7-Bromo-5-fluoro-2,3-dioxo-2,3-dihydroindol-1-ylmethyl) benzyl]isoselenourea.

26. The composition of claim 17, wherein the compound is KS100 ((3j): 2-[4-(5, 7-Dibromo-2, 3-dioxo-2, 3-dihydroindol-1-ylmethyl)benzyl]isothiourea hydrobromide).

27. The composition of claim 17, wherein the composition further comprises a pharmaceutically acceptable carrier and wherein the pharmaceutically acceptable carrier comprises liposomes.

28. The composition of claim 17, wherein the checkpoint inhibitor is a PD-1 inhibitor, PD-L1 inhibitor, or CTLA4 inhibitor.

29. The composition of claim 28, wherein the checkpoint inhibitor is chosen from anti-PD-1, nivolumab, pembrolizumab, cemiplimab, ipilimumab, atezolizumab, avelumab, durvalumab, or combinations thereof.

30. The composition of claim 17, wherein the BRAF inhibitor is sorafenib, vemurafenib, dabrafenib, encorafenib, or combinations thereof.

* * * * *